United States Patent
Wang et al.

(10) Patent No.: US 11,534,122 B2
(45) Date of Patent: Dec. 27, 2022

(54) STATIONARY SOURCE COMPUTED TOMOGRAPHY AND CT-MRI SYSTEMS

(71) Applicants: Ge Wang, Blacksburg, VA (US); Guohua Cao, Chapel Hill, NC (US)

(72) Inventors: Ge Wang, Blacksburg, VA (US); Guohua Cao, Chapel Hill, NC (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 1489 days.

(21) Appl. No.: 14/429,835

(22) PCT Filed: Sep. 20, 2013

(86) PCT No.: PCT/US2013/061049
§ 371 (c)(1),
(2) Date: Mar. 20, 2015

(87) PCT Pub. No.: WO2014/047518
PCT Pub. Date: Mar. 27, 2014

(65) Prior Publication Data
US 2015/0230766 A1   Aug. 20, 2015

Related U.S. Application Data

(60) Provisional application No. 61/768,192, filed on Feb. 22, 2013, provisional application No. 61/703,562, filed on Sep. 20, 2012.

(51) Int. Cl.
*A61B 6/00* (2006.01)
*A61B 6/03* (2006.01)
(Continued)

(52) U.S. Cl.
CPC .......... *A61B 6/4417* (2013.01); *A61B 5/0035* (2013.01); *A61B 5/0059* (2013.01);
(Continued)

(58) Field of Classification Search
CPC ..... A61B 6/4417; A61B 6/037; A61B 6/4014; A61B 6/032; A61B 6/583; A61B 6/508;
(Continued)

(56) References Cited

U.S. PATENT DOCUMENTS 4,547,892 A * 10/1985 Richey ................... A61B 6/032
378/8
7,266,179 B2   9/2007 Deuringer et al.
(Continued)

FOREIGN PATENT DOCUMENTS

WO   1997036190 A1   10/1997
WO   2002031857 A1   4/2002
(Continued)

OTHER PUBLICATIONS

Cao, G., et al. A dynamic micro-CT scanner with a stationary mouse bed using a compact carbon nanotube field emission x-ray tube, in SPIE—Med. Imaging 2009. 2009.
(Continued)

*Primary Examiner* — Sean D Mattson
(74) *Attorney, Agent, or Firm* — New River Valley IP Law, PC; Michele L. Mayberry

(57) ABSTRACT

The present invention provides stationary CT architecture for imaging at a faster temporal resolution and lower radiation dose. In embodiments, the architecture features stationary distributed x-ray sources and rotating x-ray detectors. Provided is a stationary source computed tomography (CT) architecture comprising: a detector disposed on a rotatable gantry; an x-ray source disposed on a fixed ring; wherein the detector is disposed on the gantry in a manner such that the detector is capable of rotating around a subject and of receiving a signal from the x-ray source. Embodiments of the invention include a CT-MRI scanner comprising the stationary CT architecture.

23 Claims, 29 Drawing Sheets

(51) Int. Cl.
*A61B 5/055* (2006.01)
*A61B 5/00* (2006.01)
*A61B 8/13* (2006.01)
*G01R 33/48* (2006.01)

(52) U.S. Cl.
CPC .............. *A61B 5/055* (2013.01); *A61B 6/032* (2013.01); *A61B 6/035* (2013.01); *A61B 6/037* (2013.01); *A61B 6/4007* (2013.01); *A61B 6/4014* (2013.01); *A61B 6/4078* (2013.01); *A61B 6/4233* (2013.01); *A61B 6/4429* (2013.01); *A61B 6/503* (2013.01); *A61B 6/508* (2013.01); *A61B 8/13* (2013.01); *G01R 33/4812* (2013.01); *A61B 6/583* (2013.01)

(58) Field of Classification Search
CPC ..... A61B 6/035; A61B 6/4007; A61B 6/4078; A61B 6/4233; A61B 6/4429; A61B 6/503; A61B 5/0059; A61B 5/055; A61B 5/0035; A61B 8/13; G01R 33/4812
See application file for complete search history.

(56) References Cited

U.S. PATENT DOCUMENTS

| | | | |
|---|---|---|---|
| 7,697,685 B1 | 4/2010 | Feng | |
| 8,121,249 B2 | 2/2012 | Wang et al. | |
| 8,483,351 B2 | 7/2013 | Wang et al. | |
| 2003/0072407 A1 | 4/2003 | Mihara et al. | |
| 2003/0128801 A1* | 7/2003 | Eisenberg | A61B 6/032 378/19 |
| 2007/0081703 A1* | 4/2007 | Johnson | A61B 6/465 382/128 |
| 2009/0124892 A1* | 5/2009 | Bruder | A61B 6/589 600/425 |
| 2009/0213983 A1* | 8/2009 | Vaquero Lopez | A61B 6/5235 378/4 |
| 2010/0310037 A1 | 12/2010 | Wang et al. | |
| 2010/0322498 A1* | 12/2010 | Wieczorek | A61B 6/032 382/131 |
| 2011/0105880 A1 | 5/2011 | Yu et al. | |
| 2011/0142316 A1 | 6/2011 | Wang et al. | |
| 2011/0282181 A1 | 11/2011 | Wang et al. | |
| 2012/0039434 A1 | 2/2012 | Wang et al. | |
| 2012/0257710 A1 | 10/2012 | Funk | |
| 2012/0265050 A1 | 10/2012 | Wang | |
| 2013/0237818 A1* | 9/2013 | Herrmann | A61B 6/032 600/436 |

FOREIGN PATENT DOCUMENTS

| | | |
|---|---|---|
| WO | 2008027706 A2 | 3/2008 |
| WO | 2009115982 A1 | 9/2009 |
| WO | 2010141839 A2 | 12/2010 |

OTHER PUBLICATIONS

Co-Pending Application No. PCT/US2013/061049, International Preliminary Report on Patentability dated Apr. 2, 2015, 12 pages.

Co-Pending Application No. PCT/US2013/061049, International Search Report and Written Opinion dated Dec. 26, 2013, 8 pages.
Flohr, T.G.; C. H. McCollough, H. Bruder, M. Petersilka, K. Gruber, C. Süβ, M. Grasruck, K. Stierstorfer, B. Krauss, and R. Raupach, "First performance evaluation of a dual-source CT (DSCT) system," European Radiology, vol. 16, pp. 256-268, 2006.
Guang Yang, et al. Stationary digital breast tomosynthesis system with a multi-beam field emission x-ray source array. in SPIE proceeding on Medical Imaging. 2008.
Han, W.M.; H.Y. Yu, and G. Wang, A total variation minimization theorem for compressed sensing based tomography. International Journal of Biomedical Imaging, 2009, Article ID:125871, 3 pages.
Wang Ge ; Yu Hengyong. Can interior tomography outperform lambda tomography? PNAS (Jun. 1, 2010), vol. 107, Issue 22, pp. E92-E93.
Wang, G., H. Yu, and B. De Man, An Outlook on X-ray CT Research and Development (invited paper). Medical Physics, 2008. 35(3): p. 1051-1064.
Wang, G., H. Yu, and Y. Ye, A scheme for multisource interior tomography. Med. Phys., 2009. 36(8): p. 3575-3581.
Ye et al., A General Local Reconstruction approach Based on a Truncated Hilbert Transform, Jun. 18, 2007, International Journal of Biomedical Imaging, Article ID 63634, 8 pages.
Ye YB, Yu HY, Wang G. Exact interior reconstruction with cone-beam CT. International Journal of Biomedical Imaging 2007; 2007:5. 13 pages. Article ID: 10693.
Ye, Y., Yu H.Y., and Wang G., Exact Interior Reconstruction from truncated limited-angle projection data,. International Journal of Biomedical Imaging, 2008: Article ID: 427989, 6 Pages.
Yu, H., et al. Compressive sampling based interior reconstruction for dynamic carbon nanotube micro-CT, Journal of X-ray Science and Technology, 17(4):295-303, 2009.
Yu, H., J. Yang, et al. (2009). "Supplemental analysis on compressed sensing based interior tomography." Phys Med Biol 54(18): N425-N432.
Yu, H.Y.; J.S. Yang, M. Jiang and G. Wang, Interior SPECT-exact and stable ROI reconstruction from uniformly attenuated local projections. Communications in Numerical Methods in Engineering, 2009. 25(6): p. 693-710.
Achenbach, S., et al., Contrast-enhanced coronary artery visualization by dual-source computed tomography—Initial experience. European Journal of Radiology, 2006. 57(3): p. 331-335 (re-submission).
Berrington de Gonzalez, A. and S. Darby, Risk of cancer from diagnostic X-rays: estimates for the UK and 14 other countries. Lancet, 2004. 363(9406): p. 345-351.
Chen, G.H., J. Tang, and S. Leng, Prior image constrained compressed sensing (PICCS): A method to accurately reconstruct dynamic CT images from highly undersampled projection data sets. Medical Physics, 2008. 35(2): p. 660-663.
Kachelriess, M., M. Knaup, and W.A. Kalender, Multithreaded cardiac CT. Medical Physics, 2006. 33(7): p. 2435-2447.
Scheffel, H., et al., Accuracy of dual-source CT coronary angiography: first experience in a high pre-test probability population without heart rate control. European Radiology, 2006. 16(12): p. 2739-2747.
Zhang, J., et al., Stationary scanning x-ray source based on carbon nanotube field emitters. Applied Physics Letters, 2005. 86(18).

* cited by examiner

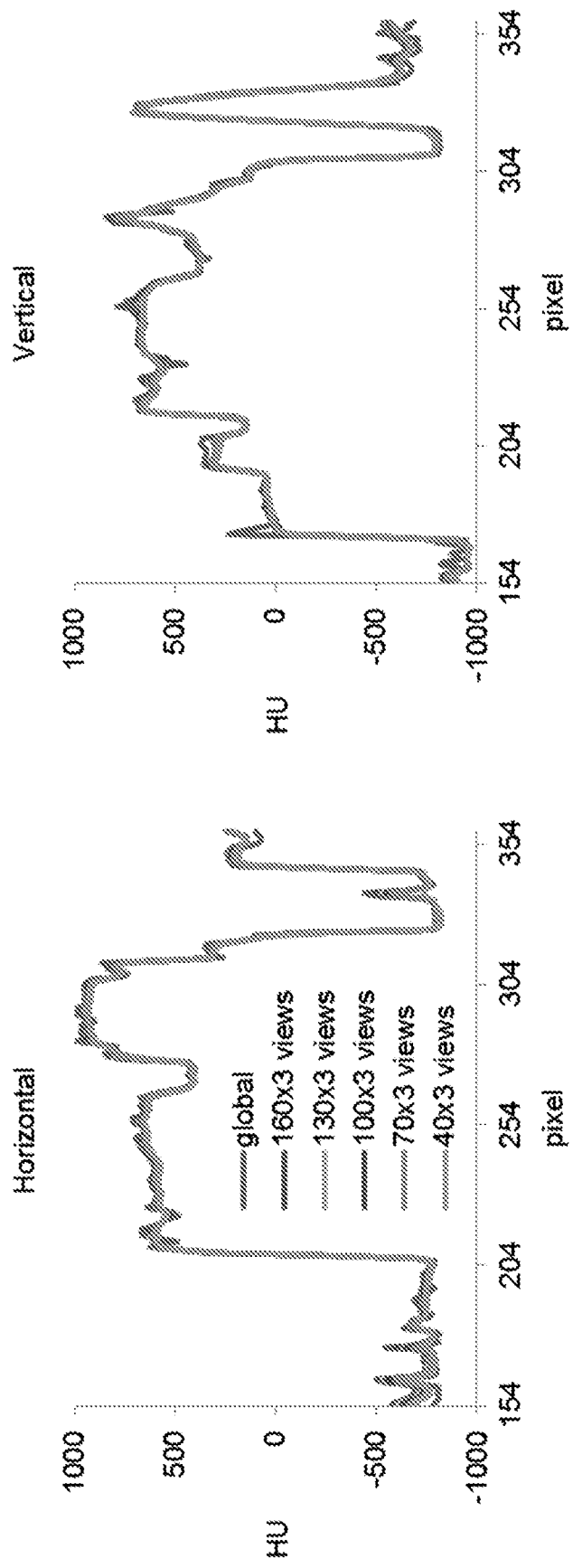

FIG. 19C

Section I: FOV 20, 3 sources, regular scatter + cross scatter

| Source/Recon Mode/FOV | Primary+Regular+Cross+Noise [0, 0.047] | Primary+Noise [0, 0.047] | Image Difference (scatter artifact) Display [0, 0.0047] |
|---|---|---|---|
| 3/full/20 | | | |
| 3/short/20 | | | |
| 3/half/20 | | | |

STATIONARY SOURCE COMPUTED TOMOGRAPHY AND CT-MRI SYSTEMS

CROSS-REFERENCE TO RELATED APPLICATIONS

This application is a National Stage application under 35 U.S.C. § 371 of International Application No. PCT/US13/61049, filed Sep. 20, 2013, which application relies on the disclosure of and claims priority to and the benefit of the filing date of U.S. Provisional Application No. 61/768,192, filed Feb. 22, 2013, and U.S. Provisional Application No. 61/703,562, filed Sep. 20, 2012, the disclosure of each of which is hereby incorporated by reference herein in their entireties.

STATEMENT OF GOVERNMENT INTEREST

This invention was made with government support under grant R01 EB011785 awarded by the National Institutes of Health, National Institute of Biomedical Imaging and Bioengineering. The government has certain rights in the invention.

BACKGROUND OF THE INVENTION

Field of the Invention

The present invention relates to computed tomography. More particularly, the present invention relates to a computed tomography architecture comprising stationary X-ray sources, and omni-tomography, including for examples, CT-MRI, based on such stationary CT architecture.

Description of Related Art

Early screening, disease staging, therapeutic assessment, interventional guidance, and other aspects of "personalized medicine" are associated with multimodality imaging and targeted agents. See Cherry S R: Multimodality imaging: Beyond PET/CT and SPECT/CT. Seminars in Nuclear Medicine 39:348-353, 2009; Patton J A, Townsend D W, Hutton B F: Hybrid imaging technology: From dreams and vision to clinical devices. Seminars in Nuclear Medicine 39:247-263, 2009. PET/CT and SPECT/CT and MRI/PET are powerful examples showing synergies, in particular for oncology and cardiology. Today, there are no longer any PET scanners alone. All of them are coupled with CT scanners. In 2009, Dr. Cherry raised a question that could still represent the thought processes of experts in the field: "Is the fusion of PET and SPECT with CT the ultimate answer in multimodality imaging, or is it just the first example of a more general trend towards harnessing the complementary nature of the different modalities on integrated imaging platforms?" The present inventors recently published an article that lays the foundations to integrate multiple major tomographic scanners into a single gantry. Wang G, Zhang J, Gao H, Weir V, Yu H Y, Cong W X, Xu X C, Shen H O, Bennett J, Furth M, Wang Y, Vannier M W: Towards omni-tomography—Grand fusion of multiple modalities for simultaneous interior tomography. PLoS ONE 7(6): e39700. doi:10.1371/journal.pone.0039700. This new thinking suggests the next stage of multimodality fusion for biomedical imaging and image-guided intervention.

Omni-tomography will be desirable for its comprehensiveness, spatiotemporal synchrony, and compactness. First of all, it is designed to collect complementary tomographic datasets simultaneously, revealing spatiotemporal links that are critical for physiological, pathological and pharmaceutical studies. Also, it has the potential to improve some major types of image-guided interventions; for example, MRI and CT guided interventions. Economically, it could be a cost-effective option relative to a full-fledged imaging center in terms of equipment space, scan time, and patient throughput, and staffing.

The enabling technology for omni-tomography is "interior tomography." See Ye Y B, Yu H Y, Wei Y C, Wang G: General local reconstruction approach based on truncated Hilbert transform; International Journal of Biomedical Imaging, ID63634, 2007; Yu H, Wang G: Compressive sensing based interior tomography. Physics in Medicine and Biology, 54:2791-2805, 2009. Traditionally, computed tomography (CT) theory targets theoretically exact image reconstruction of a cross-section or a volume as a whole assuming projections are measured without any truncation. On the other hand, many important problems are localized, or at least often observed within a relatively small region of interest (ROI). The conventional wisdom is that an internal ROI cannot be exactly reconstructed only from truncated projection data measured through the ROI. When a traditional CT algorithm is applied to truncated projections after some artificial data extrapolation, artifacts are generated overlapping features in the ROI. In 2007, the present inventors proved that the interior problem can be exactly and stably solved if a sub-region in an ROI is known. This may be termed "interior tomography" to indicate the theoretically exact nature of such an ROI reconstruction. Similar results were also independently reported by others. However, precise prior knowledge of a sub-region can be often unavailable. For example, blood density can no longer be assumed as a constant when contrast injection is involved. Hence, we were motivated to relax the requirement of prior knowledge. For that purpose, the present inventors analytically and experimentally showed that the interior problem indeed permits a unique and stable solution if the ROI is piecewise polynomial, which is a quite general image model. Other instructive references relating to imaging modalities and tomography methods employed by them and developed by one or more of the inventors include for example U.S. Pat. Nos. 8,121,249 and 8,483,351 as well as U.S. Patent Application Publication Nos. 2010/0310037, 2011/0105880, 2011/0142316, 2011/0282181, 2012/0039434, and 2012/0265050, which references are incorporated by reference herein in their entireties.

As shown in FIG. 1, conventional CT allows exact reconstruction of an object from a half scan. It was considered impossible to uniquely reconstruct an ROI from truncated local data, which is known as the interior problem. The present inventors proved in 2007 that the interior problem can be exactly and stably solved assuming a known sub-region. The present inventors showed in 2009 that for a piecewise polynomial ROI the interior problem can be uniquely solved, which was finally shown in 2012 to be stable as well.

In addition, the present inventors recently elevated interior tomography from its origin in CT to a general tomographic principle, and its validity was established for other tomographic modalities including SPECT, MRI, phase-contrast tomography, among others. As a result, relevant tomographic scanners can be made slimmer or more compact, and integrated for a comprehensive and simultaneous data acquisition from a region of interest (ROI). Both preclinical and clinical studies depend on in vivo tomography, often requiring separate evaluations by different imaging modalities.

Over the past decade, two approaches have been used for multimodality fusion: Software based registration of images acquired separately, and hybrid scanners such as PET-CT, PET-MRI, and SPECT-CT among others. While there are intrinsic limitations with both approaches, the seamless fusion of multiple imaging modalities has been challenging due to the physical (especially spatial) conflicts of these scanners. To overcome this obstacle, omni-tomography is now introduced as an out-of-box imaging scheme, with interior tomography as the enabling technology.

Omni-tomography has potential applications as a screening device for cardiac and stroke applications when CT-MRI is combined. Also an interior CT-MRI scanner can target the heart for registered functions and structures, delivery of drugs or stem cells, and guidance of complicated procedures like heart valve replacement. A unified interior CT-MRI reconstruction strategy has been shown in the aforementioned omni-tomography paper. This unification has the potential to greatly reduce radiation dose when MRI-aided interior CT is implemented. On the other hand, CT-aided MRI can provide high resolution details. Omni-tomography is an emerging frontier. Many other research and commercial uses are possible.

The need for omni-tomography for cardiovascular disease (CVD) screening is underscored by World Health Organization (WHO) estimates that there will be about 20 million deaths from CVD in 2015, accounting for 30 percent of all deaths worldwide. See WHO. *Preventing Chronic Diseases: A Vital Investment.* 2005 [cited 2012 Apr. 25]. An effective diagnosis of CVD may be achieved through cardiac computed tomography (CT). Cardiac CT has been employed to help detect or evaluate coronary heart disease, valvular heart disease, pericardial diseases, congenital heart disease, and pulmonary vein disease. See Desai, M. Y., *Cardiac Ct Beyond Coronary Angiography: Current and Emerging Non-Coronary Cardiac Applications.* Heart, 2011. 97(5): p. 417-424. Cardiac CT provides a noninvasive method for the clinicians and the scientists to obtain the detailed anatomical structure of the beating heart, evaluate functional cardiac disorder, and even diagnose the possible cardiac infarction or plaque in its early stage. In comparison with other typical techniques such as Echocardiography, SPECT, and Cardiac MRI, Cardiac CT, with its high spatial resolution, is often preferred in evaluating the suspected coronary anomalies. See Atalay, M. K., Cardiac Magnetic Resonance Imaging and Computed Tomography—State of the Art. US Radiology, 2011. 1(1): p. 34-39. The utilization of Cardiac CT is expected to rise with growth rate >10% per year and thus the collective X-ray exposure to the population will be further increased. See Brenner, D. J. and E. J. Hall, Computed Tomography—an Increasing Source of Radiation Exposure. N Engl J Med, 2007. 357(22): p. 2277-2284. Thus, the development of Cardiac CT with lower radiation exposure and higher efficiency is urgent and significant for the public health.

Since the heart is the fastest moving organ within the human body and CT scans involve ionization radiations, much of the CT developments are directed at improving temporal resolution and reducing radiation dose. A CT scan with faster temporal resolution can better 'freeze' heart motion, and hence providing sharper images and fewer artifacts. As the advances in CT technologies have spurred growth in the volume of cardiac CT procedures, the cancer risk to patients is a growing public concern. See Douglas, P. S., J. J. Carr, M. D. Cerqueira, J. E. Cummings, T. C. Gerber, D. Mukherjee, and A. J. Taylor, *Developing an Action Plan for Patient Radiation Safety in Adult Cardiovascular Medicine: Proceedings from the Duke University Clinical Research Institute/American College of Cardiology Foundation/American Heart Association Think Tank Held on Feb. 28, 2011.* J Am Coll Cardiol, 2012. Given the prevalence and mortality of CVD and the wide use of CT for cardiac screening and diagnosis, major research efforts are needed for improving cardiac CT with faster temporal resolution and lower radiation dose.

Since its introduction in 1973, CT has undergone extensive developments and its performance has been improved rapidly. See Hounsfield, G. N., *Computerized Transverse Axial Scanning (Tomography).* 1. *Description of System.* Br J Radiol, 1973. 46(552): p. 1016-1022. One noticeable improvement is that the temporal resolution has been improved from 5 min to sub-second. See Kalender, W., *Computed Tomography: Fundamentals, System Technology, Image Quality, Applications.* 2nd ed. 2005, Erlangen: Publicis Corporate Publishing. The fastest temporal resolution is provided by the second-generation dual-source CT (DSCT), which gives a temporal resolution up to 75 ms (Definition Flash, Siemens). See Lell, M., M. Marwan, T. Schepis, T. Pflederer, K. Anders, T. Flohr, T. Allmendinger, W. Kalender, D. Ertel, C. Thierfelder, A. Kuettner, D. Ropers, W. G. Daniel, and S. Achenbach, *Prospectively Ecg-Triggered High-Pitch Spiral Acquisition for Coronary Ct Angiography Using Dual Source Ct: Technique and Initial Experience.* Eur Radiol, 2009. 19(11): p. 2576-2583; Flohr, T. G., S. A. Leng, L. F. Yu, T. Allmendinger, H. Bruder, M. Petersilka, C. D. Eusemann, K. Stierstorfer, B. Schmidt, and C. H. McCollough, *Dual-Source Spiral Ct with Pitch up to 3.2 and 75 Ms Temporal Resolution: Image Reconstruction and Assessment of Image Quality.* Medical Physics, 2009. 36(12): p. 5641-5653. This temporal resolution is achieved by arranging two x-ray tubes and two detectors on a single gantry with a rotation time of 270 ms. While well received, this temporal resolution works best only when image acquisition is ECG-gated to the relatively quiet diastolic phase. See Achenbach, S., D. Ropers, A. Kuettner, T. Flohr, B. Ohnesorge, H. Bruder, H. Theessen, M. Karakaya, W. G. Daniel, W. Bautz, W. A. Kalender, and K. Anders, *Contrast-Enhanced Coronary Artery Visualization by Dual-Source Computed Tomography—Initial Experience.* European Journal Of Radiology, 2006. 57(3): p. 331-335; Flohr, T. G., C. H. McCollough, H. Bruder, M. Petersilka, K. Gruber, C. Suss, M. Grasruck, K. Stierstorfer, B. Krauss, R. Raupach, A. N. Primak, A. Kuttner, S. Achenbach, C. Becker, A. Kopp, and B. M. Ohnesorge, *First Performance Evaluation of a Dual-Source Ct (Dsct) System.* European Radiology, 2006. 16(2): p. 256-268; Johnson, T. R. C., K. Nikolaou, B. J. Wintersperger, A. W. Leber, F. von Ziegler, C. Rist, S. Buhmann, A. Knez, M. F. Reiser, and C. R. Becker, *Dual-Source Ct Cardiac Imaging: Initial Experience.* European Radiology, 2006. 16(7): p. 1409-1415; Kachelriess, M., M. Knaup, and W. A. Kalender, *Multithreaded Cardiac Ct.* Medical Physics, 2006. 33(7): p. 2435-2447; Scheffel, H., H. Alkadhi, A. Plass, R. Vachenauer, L. Desbiolles, O. Gaemperli, T. Schepis, T. Frauenfelder, T. Schertler, L. Husmann, J. Grunenfelder, M. Genoni, P. A. Kaufmann, B. Marincek, and S. Leschka, *Accuracy of Dual-Source Ct Coronary Angiography: First Experience in a High Pre-Test Probability Population without Heart Rate Control.* European Radiology, 2006. 16(12): p. 2739-2747. To image various cardiac phases and CT patients with irregular heart rates (e.g. arrhythmia), a temporal resolution down to 50 ms is needed. See Leschka, S., S. Wildermuth, T. Boehm, L. Desbiolles, L. Husmann, A. Plass, P. Koepfli, T. Schepis, B. Marincek, P. A. Kaufmann, and H. Alkadhi, *Noninvasive Coronary*

*Angiography with 64-Section Ct: Effect of Average Heart Rate and Heart Rate Variability on Image Quality.* Radiology, 2006. 241(2): p. 378-385; Mahesh, M. and D. D. Cody, *Physics of Cardiac Imaging with Multiple-Row Detector Ct.* RadioGraphics, 2007. 27: p. 1495-1509.

There are two strategies to obtain faster temporal resolution: faster gantry rotation and multiple x-ray sources. However, increasing the temporal resolution via an even faster gantry rotation speed appears to be beyond today's mechanical limits. At a gantry rotation speed of about 300 ms, the gravitational force (i.e. g-force) on the gantry can reach 30 g, which is approximately 10 times higher than that experienced during the space shuttle take-off. See Kalender, W., *Computed Tomography: Fundamentals, System Technology, Image Quality, Applications.* 2nd ed. 2005, Erlangen: Publicis Corporate Publishing; Schardt, P., J. Deuringer, Jr., Freudenberger, E. Hell, W. Knupfer, D. Mattern, and M. Schild, *New X-Ray Tube Performance in Computed Tomography by Introducing the Rotating Envelope Tube Technology.* Medical Physics, 2004. 31(9): p. 2699. An innovative alternative is the electron beam CT (EBCT), which can achieve a temporal resolution of about 30 ms by sweeping an electron beam across a stationary anode ring that encloses the patient. See M. J. Lipton, C. B. Higgins, D. Farmer, and D. P. Boyd, *Cardiac Imaging with a High-Speed Cine-Ct Scanner: Preliminary Results.* Radiology, 1984. 152(3): p. 579-582. Compared to a rotating-gantry CT, the EBCT allows the source-point to be swept with far greater speed. The multi-source strategy is well known to improve the temporal resolution of CT scanners. However, as demonstrated by the dynamic spatial reconstructor (DSR) in the 1980s and depending on the actual geometry used, the number of sources was limited by the proximity of adjacent x-ray sources to prevent adjacent beams from overlapping. See Ritman, E. L., J. H. Kinsey, R. A. Robb, B. K. Gilbert, L. D. Harris, and E. H. Wood, *3-Dimensional Imaging of Heart, Lungs, and Circulation.* Science, 1980. 210(4467): p. 273-280; Ritman, E. L., L. D. Harris, J. H. Kinsey, and R. A. Robb, *Computed Tomographic Imaging of the Heart: The Dynamic Spatial Reconstructor.* Radiol. Clin. North. Am., 1980. 18(3): p. 547-555; Ritman, E. L., R. A. Robb, and L. D. Harris, *Imaging Physiological Functions: Experience with the Dsr*1985: philadelphia: praeger. Additionally, International Patent Application Publication No. WO 2008/027706 provides an example of efforts toward addressing some of these issues.

For the radiation dose, clinical practice requires adhering to the principle of keeping radiation doses as low as reasonably achievable (ALARA). The dose issue is especially critical for CT perfusion imaging, in which a high radiation dose (~10 mSv) is accumulated from multiple CT acquisitions. See Marcus, R. P., K. Nikolaou, D. Theisen, M. F. Reiser, and F. Bamberg, *Myocardial Perfusion Imaging by Computed Tomography: Today and Tomorrow.* Int J Clin Pract Suppl, 2011(173): p. 14-22. The dose issue will become even more prominent if one wants to improve the spatial resolution, because to double the spatial resolution in all 3 spatial directions without affecting the contrast-to-noise ratio (CNR), one has to increase the radiation dose by a factor of 24 (i.e. 16-fold increase). See Flohr, T. G., R. Raupach, and H. Bruder, *Cardiac Ct: How Much Can Temporal Resolution, Spatial Resolution, and Volume Coverage Be Improved?* J Cardiovasc Comput Tomogr, 2009. 3(3): p. 143-152. Previously, a number of dose reduction techniques have been developed, but the success is far from sufficient. See van Gelder, R. E., H. W. Venema, J. Florie, C. Y. Nio, I. W. O. Serlie, M. P. Schutter, J. C. van Rijn, F. M. Vos, A. S. Glas, P. M. M. Bossuyt, J. F. W. Bartelsman, J. S. Lameris, and J. Stoker, *Ct Colonography: Feasibility of Substantial Dose Reduction—Comparison of Medium to Very Low Doses in Identical Patients.* Radiology, 2004. 232(2): p. 611-620; Yu, H., S. Zhao, E. A. Hoffman, and G. Wang, *Ultra-Low Dose Lung Ct Perfusion Regularized by a Previous Scan.* Academic Radiology, 2009. 16(3): p. 363-373; Tkaczyk, E., Y. Du, D. Walter, X. Wu, J. Li, and T. Toth. *Simulation of Ct Dose and Contrast-to-Noise as Function of Bowtie Shape. in SPIE Medical Imaging, Volume* 5368, P 403-410. 2004; Suess, C. and X. Y. Chen, *Dose Optimization in Pediatric Ct: Current Technology and Future Innovations.* Pediatric Radiology, 2002. 32(10): p. 729-734; La Riviere, P. J., *Penalized-Likelihood Sinogram Smoothing for Low-Dose Ct.* Medical Physics, 2005. 32(6): p. 1676-1683.

Recently, exciting progresses have been seen in the CT field. Among them, two innovations are particularly relevant to cardiac CT: compressive-sensing (CS) based interior tomography (see Yu, H. and G. Wang, *Compressed Sensing Based Interior Tomography.* Phys Med Biol, 2009. 54(9): p. 2791-2805) and distributed x-ray sources. See Frutschy, K., B. Neculaes, L. Inzinna, A. Caiafa, J. Reynolds, Y. Zou, X. Zhang, S. Gunturi, Y. Cao, B. Waters, D. Wagner, B. D. Man, D. McDevitt, R. Roffers, B. Lounsberry, and N. J. Pelc. High Power Distributed X-Ray Source. 2010. 7622. SPIE; Sprenger, F., X. Calderon, E. Gidcumb, J. Lu, X. Qian, D. Spronk, A. Tucker, G. Yang, and O. Zhou. *Stationary Digital Breast Tomosynthesis with Distributed Field Emission X-Ray Tube.* 2011. 7961. SPIE. The interior tomography solved the decades-long interior problem and allows precise reconstruction of a region-of-interest (ROI) from truncated projections. Yu, H. and G. Wang, *Compressed Sensing Based Interior Tomography.* Physics in Medicine and Biology, 2009. 54(9): p. 2791-2805; Yu, H., J. Yang, M. Jiang, and G. Wang, *Supplemental Analysis on Compressed Sensing Based Interior Tomography.* Phys Med Biol, 2009. 54(18): p. N425-N432. This is quite different from the conventional CT, in which detectors always cover the full transaxial extent of the object. The interior tomography offers opportunities to reduce detector size, suppress scattering artifacts, and lower radiation dose. Radiation doses could be further reduced when interior tomography is combined with the compressive-sensing framework. See Yu, H. and G. Wang, *Compressed Sensing Based Interior Tomography.* Phys Med Biol, 2009. 54(9): p. 2791-2805. The distributed x-ray sources produce x-ray radiations by extracting electron beams from an array of cathodes and sending each electron beam to a distinctive focal spot on the anode. The cathode can be made of either the dispenser cathode emitters (DCE's) (see Frutschy, K., B. Neculaes, L. Inzinna, A. Caiafa, J. Reynolds, Y. Zou, X. Zhang, S. Gunturi, Y. Cao, B. Waters, D. Wagner, B. D. Man, D. McDevitt, R. Roffers, B. Lounsberry, and N. J. Pelc. *High Power Distributed X-Ray Source.* 2010. 7622. SPIE), or the novel field emitters such as carbon nanotubes (CNT's). See Sprenger, F., X. Calderon, E. Gidcumb, J. Lu, X. Qian, D. Spronk, A. Tucker, G. Yang, and O. Zhou. *Stationary Digital Breast Tomosynthesis with Distributed Field Emission X-Ray Tube.* 2011. 7961. SPIE The electron beams (and hence the corresponding x-ray beams) can be electronically switched on and off by applying and removing the corresponding extraction voltages on the cathodes. By programming the extraction voltages, a scanning x-ray beam can be generated to illuminate the object from different viewing angles, therefore enabling tomographic imaging without mechanical motion. See Qian, X., A. Tucker, E. Gidcumb, J. Shan, G. Yang, X. Calderon-Colon, S. *Sultana*, J. P. Lu, O.

Zhou, D. Spronk, F. Sprenger, Y. H. Zhang, D. Kennedy, T. Farbizio, and Z. X. Jing, *High Resolution Stationary Digital Breast Tomosynthesis Using Distributed Carbon Nanotube X-Ray Source Array*. Medical Physics, 2012. 39(4): p. 2090-2099. The CNT-based distributed x-ray sources are especially appealing, because they utilize "cold" CNT cathodes that work at the room temperature and hence allow more compact packaging and faster and more flexible control of x-ray beams. See Zhang, J., G. Yang, Y. Z. Lee, S. Chang, J. P. Lu, and O. Zhou, *Multiplexing Radiography Using a Carbon Nanotube Based X-Ray Source*. Appl. Phys. Lett., 2006. 89: p. 064106.

Cardiovascular computed tomography (CVCT) has been successfully applied for the diagnosis of a series of heart diseases. However, the limitations of temporal and spatial resolution and radiation dose inhibit the utilization of CVCT for more clinical applications. The specific primary bottlenecks of the current CVCT include the difficulties of the synchronization with high or arrhythmic heart rates, the inability to measure blood flow, the detection of vulnerable plaques, the separation of calcium from iodine signals, the study of myocardial micro-vascular structure and perfusion, as well as the risk of ionizing radiation exposure. Further, current cardiac computed tomography (CT) is too slow for high or irregular heart rates, and its high radiation dose is a public concern. In the current CT architecture, x-ray tubes are mechanically spun around an object to collect projections, and wide x-ray beams are used to cover the entire transaxial extent of an object without truncation. This architecture represents the major hurdle for increasing the temporal resolution and reducing the radiation dose for cardiac CT. Thus, there is a need in the art for CVCT methods that overcome these limitations.

SUMMARY OF THE INVENTION

To this end, the inventors provide a stationary cardiac CT architecture that combines the latest developments in interior tomography and distributed x-ray source. The inventive stationary CT architecture provides imaging at a faster temporal resolution and lower radiation dose. In exemplary embodiments, the architecture features three stationary distributed x-ray sources and three rotating x-ray detectors. In some aspects, each of the three sources contains about 100 x-ray beams. The three detectors may have a narrow transaxial width, and acquire truncated projection data for a 200 mm region-of-interest in diameter. In synchrony with the rotating detectors, the three source arrays may be electronically activated to simulate the spinning of three conventional single-beam x-ray sources. Three source-detector chains can work in parallel to acquire three projections simultaneously and speed up temporal resolution. X-ray beams may be restricted to cover only the local region to reduce full-body radiation dose. The inventive architecture can enable ≤50 ms temporal resolution and greatly reduced radiation dose.

Further, the inventors provide a novel design of a CT-MRI system for Omni-tomography and a process to make this CT-MRI scanner based on the stationary CT architecture. In embodiments, the CT-MRI system for Omni-tomography provides for ease of integration and shielding without significant electromagnetic interference, based on a design of stationary x-ray sources and detectors in the CT subsystem. In some aspects, the omni-tomographic reconstruction may be made based on a dictionary/atlas framework. The novel CT-MRI scanners are useful for quantitative and interventional opportunities in cost-effective biomedical applications, such as early screening, disease staging, therapeutic assessment, interventional guidance, and other aspects of "personalized medicine".

According to embodiments, the MRI subsystem of the CT-MRI system comprises two permanent magnet heads at each magnetic pole. It is preferred that the MRI subsystem is operably configured for providing a magnetic field for a ROI of about 15-20 cm at a center point of the gantry, with a vertical gap between magnet poles in the range of about 30 70 cm and with magnet heads about 20-60 cm in width and about 40-120 cm in length. Smaller or larger ROIs can be targeted and the systems and devices operably configured appropriately. The MRI subsystem can provide a magnetic field for a ROI of about 0-50 cm, such as about 30-45 cm, or from about 1-5 cm, or further from about 3-10 cm. The magnet poles can be separated by a vertical distance of about 5-200 cm, depending on the overall size of the gantry and the expected size of the patient or subject.

Systems and devices of the invention can have solid or hollow magnet heads, with preferably hollow magnet heads.

The MRI subsystem in embodiments comprises permanent magnets for providing a homogeneous or inhomogeneous local magnetic field.

Embodiments of the stationary source CT architecture (either as a standalone unit, or as a subsystem of a CT-MRI system) may have some or all of the following features. The inventive CT architecture may use a commercial CT x-ray source or a carbon nanotube (CNT) CT x-ray source. Further the CNT CT x-ray source may be single-beam source or a multi-beam array. Alternatively, or in addition, the x-ray source may be a vacuum tube with a cathode for emitting electrons into the vacuum and an anode to collect the electrons, which establishes a flow of electrical current (beam) through the vacuum tube. A high voltage power source, such as 20 kV to 200 kV is in operable communication with the cathode and anode to accelerate the electrons. Electrons from the cathode collide with the anode material, such as tungsten, molybdenum, or copper, and accelerate other electrons within the anode material. Typically, about 1% of the energy generated is radiated perpendicular to the path of the electron beam as x-rays and the remaining energy is released as heat. In some circumstances, heat build up can melt the anode causing undesirable complications, so embodiments of the invention are operably configured to address this issue.

Still further, the inventive CT architecture may use robust Few-view Interior Tomography (FIT) methods as reconstruction algorithms. The reconstruction algorithms may include a dictionary-based sparsity constraint based in part on Equations C.2-1 and C.2-2 as described in the "Dictionary-based Sparse Representation" section of the Examples.

BRIEF DESCRIPTION OF THE DRAWINGS

The accompanying drawings illustrate certain aspects of embodiments of the present invention, and should not be used to limit or define the invention. Together with the written description the drawings explain certain principles of the invention.

FIGS. 7A and 7B are graphs of profiles along horizontal and vertical central lines for the images in FIGS. 6A-6E.

FIGS. 10A-B are schematic diagrams showing the ring-shaped design for omnitomography, wherein FIG. 11A shows a 3D rendering of the FIG. 10A shows an in-plane view and FIG. 10B shows a through-plane view. There are two static rings and one rotating ring for omnitomography. While the C-arm 1109 is a permanent magnet and the outer ring 1113 contains PET crystals, ring 1127 supports a CT tube 1134 (or x-ray tube), a CT detector 1146 (or x-ray detector) and a pair of single-photon emission computed tomography (SPECT) cameras 1158A and 1158B. The CT-SPECT ring 1127 is on a slip ring 1161 (like a large ball bearing) as the interface for power and data. The CT-SPECT ring 1127, the slip ring 1161, and the PET ring 1113 all go through the magnetic poles.

FIGS. 12A and 12B are images showing interior reconstruction of a sheep chest from a real dataset, wherein FIG. 12A shows conventional reconstruction from a complete dataset (white circle for the ROI), and FIG. 12B shows compressive sensing based interior reconstruction only from data through the ROI.

FIGS. 15A and 15B are graphs showing X-ray source simulation wherein FIG. 15A is a graph showing anode thermal dynamics simulated using ANSYS and FIG. 15B is a graph showing electron optics simulated using Opera.

FIGS. 16A-C are schematic diagrams showing simulations of STRICT from X-ray projection to image reconstruction using CATSIM and a numerical thorax phantom. Details: 12 cm ROI (circles), source array cover angle 72.68°, wherein FIG. 16A shows the global reconstruction with 720 projections and filtered back projection, FIG. 16B shows interior tomography with 66 beams per source array and the few-view interior reconstruction algorithm, and FIG. 16C shows interior tomography with 132 beams per source array and few-view interior reconstruction algorithm.

FIGS. 17A-C are images showing the simulation of the interior tomography based on STRICT architecture and clinical cardiac CT data: display window [−1000 HU, 1800 HU], white circle ROI, wherein FIG. 17A shows the benchmark global CT image (512×512), FIG. 17B shows the equivalent half scan image (205×205), and FIG. 17C shows the equivalent short scan image (205×205).

FIGS. 19A-G are images showing image artifacts induced by scatter (FIGS. 19A-D) and image artifacts induced by interior tomography (FIGS. 19E-G) of simulations of conventional scans and reduced FOV scans of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Stationary CT Architecture

Figure 1:
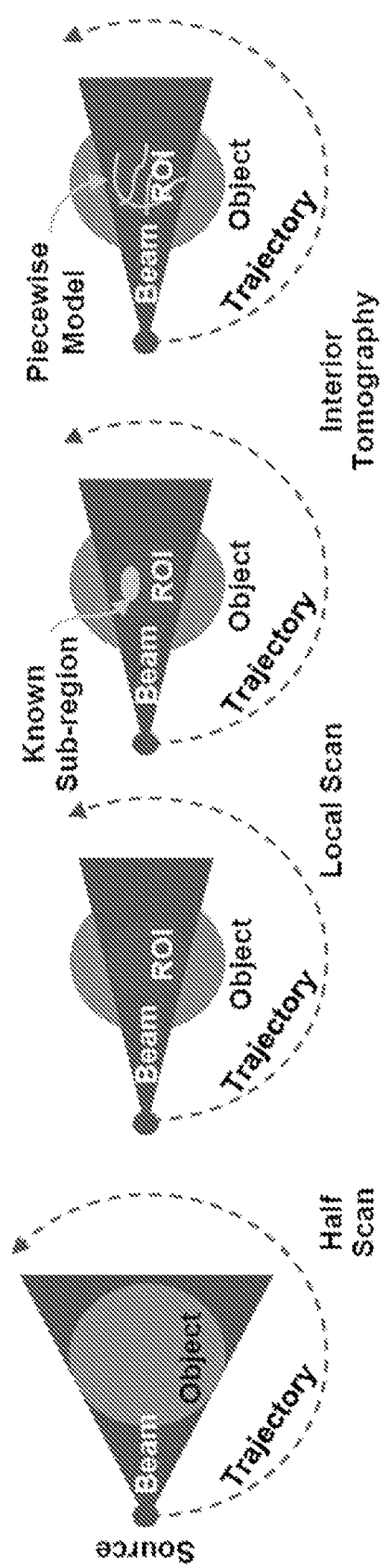
FIG. 1 is a schematic diagram showing trajectories for a half-scan, local scan, and interior tomography.
Figure 2:
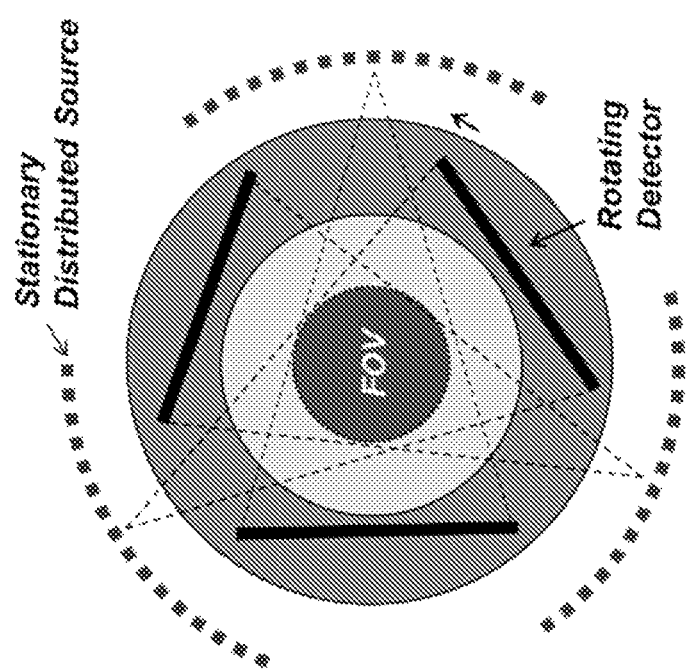
FIG. 2 is a schematic diagram showing an embodiment of the stationary cardiac CT architecture with three distributed x-ray sources and three rotating detectors.
Figure 14:
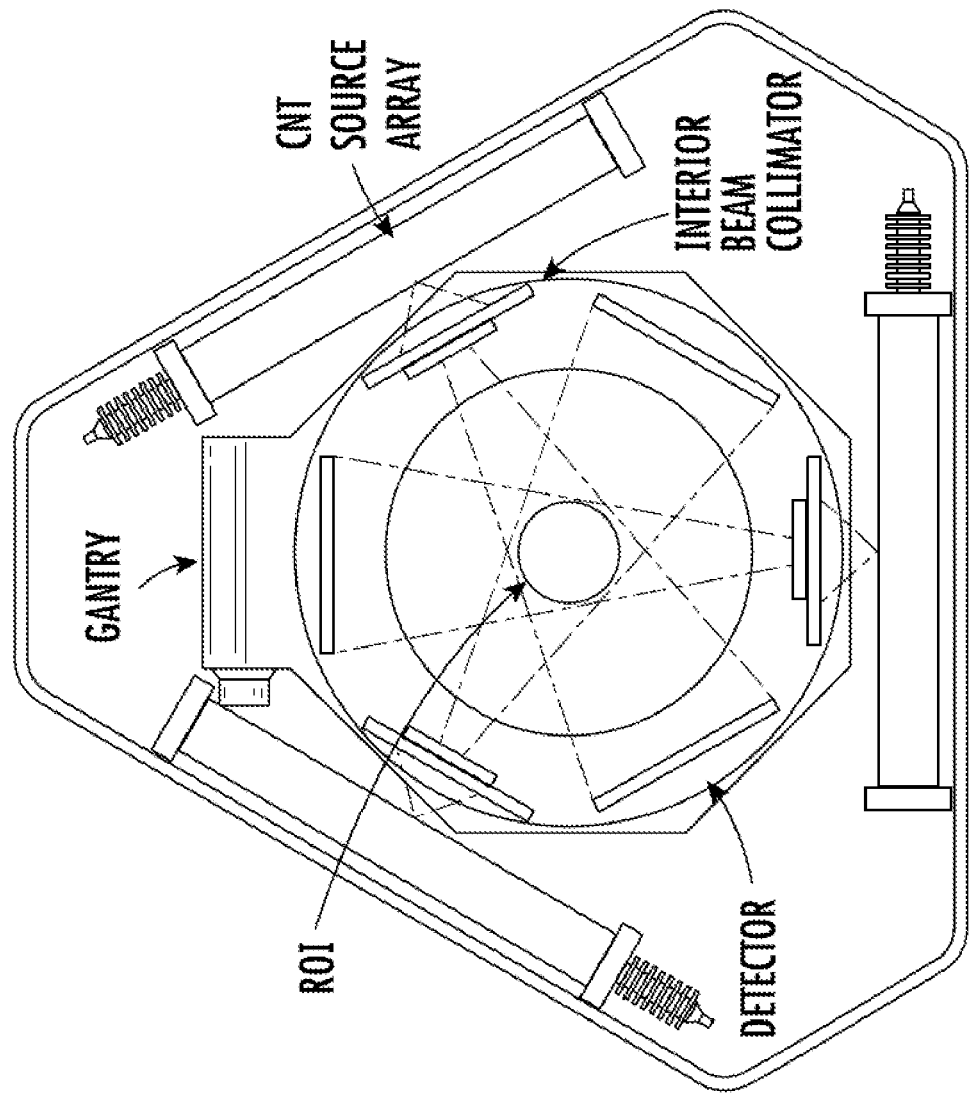
FIG. 14 is a schematic diagram showing Interior (Left) and global (Right) CT modes of an exemplary STRICT architecture.

One embodiment of an exemplary stationary cardiac CT architecture embodiment of the invention is illustrated in FIG. 2 (see also FIG. 14). The architecture has three stationary distributed x-ray sources and three rotating detectors. In embodiments, any number of arrays and detectors can be used as well as any number of x-ray sources incorporated into the arrays, such as from 1, 2, 3, 4, 5, 6, 7, 8, 9, 10, 11, 12, 13, 14, 15, 16, 17, 18, 19, or 20 arrays and/or detectors. Similarly, any number of x-ray sources can be present within an array, such as from 1 to 100, or from 2-90, or from 3-80, or from 5-70, or from 8 to 60, or from 10 to 50, such as from 15-40, or from 20-30, such as from 12-35, or from 18-45 and so on. Preferably, there are an equal number of arrays and corresponding detectors. The arrays can also be referred to generically as sources in the context of this disclosure. Even further, within this disclosure the architecture of embodiments of the invention can also be referred to generally as stationary-source rotating-detector CT (SSRDCT). It is important to note that in embodiments the x-ray sources can also be operably configured to rotate if desired. The three source-detector chains of this embodiment are identical and symmetrically positioned around the object, however, other configurations are also possible, such as using an array of one type of x-ray source with another array or other arrays comprising a different type of x-ray source, or using different types of x-ray sources within a particular array. The source-to-isocenter distance (SID) and the source-to-detector distance (SDD) may be similar to most commercial CT scanners. Exemplary geometrical parameters of the architecture are listed in Table 1. An exemplary field-of-view (FOV) is 200 mm, which is sufficient to cover the transaxial extent of typical human hearts, which is much less than the conventional 500 mm FOV. Indeed, using the invention, FOVs in the range of 10-300 mm, or from 20-250 mm, or from 40-220 mm, or from 50-180 mm, or from 60-150 mm, or from 80-120 mm, or from 90-110 mm can be used. This exemplary geometry allows for reuse, or use with slight modifications, the existing and mature CT technologies in detectors, gantry, slip rings, and so on. A reduced FOV results in less radiation exposure for the subject.

TABLE 1

Geometrical parameters of the cardiac CT architecture. Unit is mm.

| | |
|---|---|
| Number of Source-Detector Chains | 3 |
| Source to Isocenter Distance | 540 |
| Source to Detector Distance | 950 |
| Field of View | 200 |

In this embodiment, each distributed x-ray tube may have multiple x-ray sources that are equiangularly (relative to the isocenter) distributed in the shared vacuum envelope. During a CT scan, the x-ray sources within an x-ray tube may be sequentially turned on and off from one end to the other. Generally speaking, as the voltage is increased the x-ray can be generated, then the voltage decreased to a level that causes switching off of the x-ray source. X-ray sources within an array and from one array to the next can be switched on and off in any desired sequence to obtain a desired result, such as sequentially in a chasing pattern, or in a skipping pattern, or otherwise alternating from one x-ray source to another within an array or across multiple arrays within a system.

Thus, each x-ray source may give a pulsed radiation. Switching can be performed through programming the gate voltage on the corresponding cathode. See Frutschy, K., B. Neculaes, L. Inzinna, A. Caiafa, J. Reynolds, Y. Zou, X. Zhang, S. Gunturi, Y. Cao, B. Waters, D. Wagner, B. D. Man, D. McDevitt, R. Roffers, B. Lounsberry, and N. J. Pelc. *High Power Distributed X-Ray Source*. 2010. 7622. SPIE; Zhang, J., G. Yang, Y. Z. Lee, S. Chang, J. P. Lu, and O. Zhou, *Multiplexing Radiography Using a Carbon Nanotube Based X-Ray Source*. Appl. Phys. Lett., 2006. 89: p. 064106. In embodiments, the switching of the x-ray sources can be synchronous to the rotation of the opposing detectors, simulating the spinning of three traditional single-beam x-ray sources. Switching can also be timed in a manner to ensure no overheating/melting of the anode during use, such as using a timing sufficient to obtain an image on the detector then switching to the next x-ray source.

All x-ray beams may be collimated toward the 200 mm FOV, which in certain embodiments can be the heart region within human body. This will reduce radiation dose to regions outside the FOV. Compared to most commercial CT scanners in which a typical FOV size of 500 mm is used, the inventive architecture allows the detector size to be reduced by 60%. One way of collimating the x-ray beam is to provide structure mounted to the rotatable gantry at a desired distance between the detector and x-ray source with a window for the beam to pass through, which is sized and shaped to focus the beam to desired dimension(s), such as width, height, and/or cross-sectional area.

The small detector size of the inventive architecture allows three detectors and correspondingly three x-ray beams to be fitted, without overlapping, on a conventional CT gantry of about 1 m in diameter. Three projection images can be acquired from the three source-detector chains simultaneously.

Numerical Analyses

Scan Angle

Figure 3:
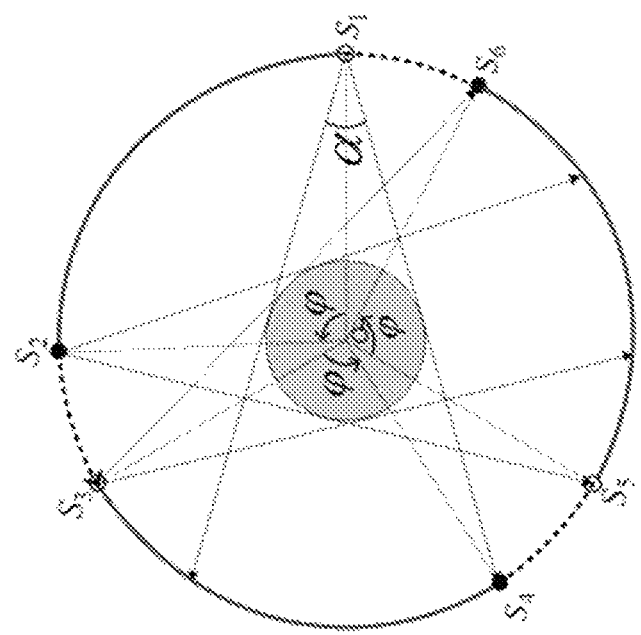
FIG. 3 is a schematic diagram showing the scan angles of the three source arrays. The three source arrays are arranged symmetrically around the same FOV, which is represented by the inner circular region.

As illustrated in the embodiment of FIG. 3, the three identical source arrays are symmetrically positioned around the FOV. The following analysis is instructive of the scan angle used in this embodiment of the invention. In order to have a complete projection data set for the FOV, the effective scan angle (indicated by $\angle S_1 O S_4$) should be $\pi + \alpha$ with $\alpha$ as the fan angle. Assuming each source array has a coverage angle $\varphi$, that is, $$\angle S_1 O S_2 = \angle S_3 O S_4 = \angle S_5 O S_6 = \varphi. \tag{1}$$

Then we have the angle $$\angle S_2 O S_3 = \angle S_4 O S_5 = \angle S_6 O S_1 = (2\pi - 3\varphi)/3 - \tag{2}$$

For a short scan (i.e. 180°+fan angle scan) from $S_1$ to $S_4$, the data from $S_2$ to $S_3$ is missing. However, this can be compensated by the opposing source array from $S_5$ to $S_6$. To meet this requirement, we have $$\begin{cases} \angle S_1 O S_4 = \pi + \alpha \\ \angle S_1 O S_4 = \angle S_1 O S_2 + \angle S_2 O S_3 + \angle S_3 O S_4 = \varphi + (2\pi - 3\varphi)/3 + \varphi \end{cases} \tag{3}$$

Immediately, we get $$\varphi = \pi/3 + \alpha - \tag{4}$$

Therefore, to satisfy the data requirement for a short scan, each source array should cover an angle of $\pi/3 + \alpha$. Correspondingly, for a short scan each detector should rotate an angle of $\pi/3 + \alpha$. From the geometry in Table 1, we can calculate the fan angle $\alpha$ to be 21°.

Temporal Resolution

Let us denote the gantry rotation time as $T_{rot}$. Based on the above analysis on the scan angle, we can easily derive that the temporal resolution for a short scan in the of the SSRDCT architecture is $(\pi/3 + \alpha)/2\pi * T_{rot}$. For the DSCT and the conventional the single-source CT (SSCT) architectures, the temporal resolutions for short scan are $(\pi/2 + \alpha)/2\pi * T_{rot}$, and $(\pi + \alpha)/2\pi * T_{rot}$, respectively. For half scan (i.e. 180° scan), the temporal resolution would be $T_{rot}/6$, $T_{rot}/4$, and $T_{rot}/2$ for SSRDCT, DSCT, and SSCT, respectively. The relative temporal resolutions for the three architectures are listed in Table 2. For all the three architectures, the gantry rotation time, $T_{rot}$, was assumed to be same, and the SID was taken as 540 mm. The present inventors noticed that, compared to the latest DSCT architecture, the temporal resolution in the SSRDCT architecture will be improved by more than ⅓, for both the short-scan and half-scan modes. If the gantry rotation time $T_{rot}$ is assumed as 270 ms, the temporal resolution in the SSRDCT architecture will be 61 ms for the short-scan mode and 45 ms for the half-scan mode.

TABLE 2

Comparison of temporal resolutions for the SSCT, DSCT, and STRICT architecture. The gantry rotation time was taken as the same, and the SID was 540 mm.

| Architecture | SSCT | DSCT | SSRDCT |
|---|---|---|---|
| Number of Source-Detector Chains | 1 | 2 | 3 |
| Field of View (mm) | 500 | 340[a] | 200 |
| Relative Temporal Resolution - Short Scan[b] | 1 | 0.54 | 0.35 |
| Relative Temporal Resolution - Half Scan[b] | 1 | 0.50 | 0.33 |

[a]The two detectors in DSCT have different sizes and the system FOV is limited by the smaller detector at 340 mm [7].
[b]Temporal resolutions are normalized to those in the traditional SSCT architecture.

Radiation Dose

At the same SID, the radiation dose at isocenter is proportional to the total exposure during a CT scan. For a same SID, constant x-ray flux can be assumed at the isocenter, given a particular x-ray source technology. Therefore, the radiation dose at isocenter is solely dependent on the total exposure time. For the SSCT architecture, the x-ray source is on continuously during the data acquisition for a single slice image, thus the total exposure time per CT scan equals to the corresponding temporal resolution. For the DSCT architecture, since the two sources are on continuously during the data acquisition, the total exposure time is two times of its temporal resolution. For the SSRDCT architecture, each x-ray source will give a single pulsed exposure, thus the total exposure time is the summation of x-ray exposure times from individual x-ray sources in the three source arrays. This total exposure time is not necessarily three times of its temporal resolution, because a 'dead time' (i.e. a time period without exposure) can be introduced between two consecutive pulsed exposures from two neighboring x-ray sources in a source array. The dead time will significantly reduce the total exposure time per CT scan in the SSRDCT architecture, potentially saving the radiation dose.

To reduce radiation exposure to patients, there have been many efforts in developing image reconstruction algorithms that operate with fewer projection views, less of a scanning arc or lower x-ray intensity per view. See Yu, H. and G. Wang, *Compressed Sensing Based Interior Tomography*. Phys Med Biol, 2009. 54(9): p. 2791-2805; Sidky, E. Y. and X. Pan, *Image Reconstruction in Circular Cone-Beam Computed Tomography by Constrained, Total-Variation Minimization*. Phys Med Biol, 2008. 53(17): p. 4777-4807; Chen, G. H., J. Tang, B. Nett, Z. H. Qi, S. A. Leng, and T. Szczykutowicz, *Prior Image Constrained Compressed Sensing (Piccs) and Applications in X-Ray Computed Tomography*. Current Medical Imaging Reviews, 2010. 6(2): p. 119-134. These algorithms are highly synergistic to the architecture of the invention. They would permit decent image quality to be obtained in the SSRDCT architecture with less x-ray sources in each source array, smaller coverage angle per array, and lower x-ray source power; all will result into a system that is more compact and at lower cost. In particular, lowering x-ray intensity per view will enable the stationary distributed x-ray sources to adopt the fixed-anode design, which will dramatically simplify the source design and reduce the demand on the amount of electron currents from the cathodes. In the following section, the present inventors investigate the performance of the architecture using a clinical cardiac CT dataset and the total variation minimization (TVM) with steepest descent search algorithm (TVM-SD). See Yu, H. and G. Wang, *A Soft-Threshold Filtering Approach for Reconstruction from a Limited Number of Projections*. Physics in Medicine and Biology, 2010. 55(13): p. 3905-3916; Liu, B., G. Wang, E. L. Ritman, G. Cao, J. Lu, O. Zhou, L. Zeng, and H. Yu, *Image Reconstruction from Limited Angle Projections Collected by Multisource Interior X-Ray Imaging Systems*. Physics in Medicine and Biology, 2011. 56(19): p. 6337-6357.

Figure 4B:
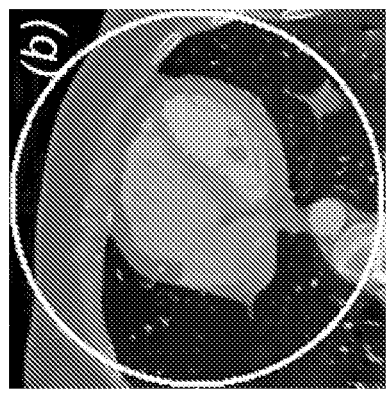
FIGS. 4A-4C are images showing reconstructed slice images using the TVM-SD algorithm with a display window [−1000 HU, 1800 HU] for the reconstructed global image from the full dataset (60 iterations) (FIG. 4A), and reconstructed ROI images for the short-scan mode (FIG. 4B)) and the half-scan mode (FIG. 4C) in the SSRDCTT architecture (both at 200 iterations).
Figure 4C:
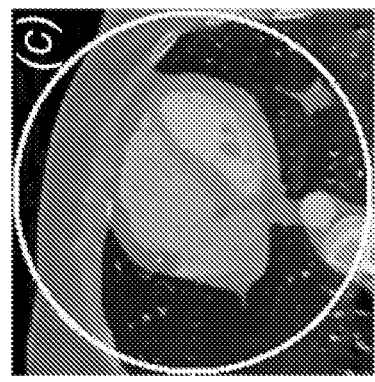
Figure 4A:
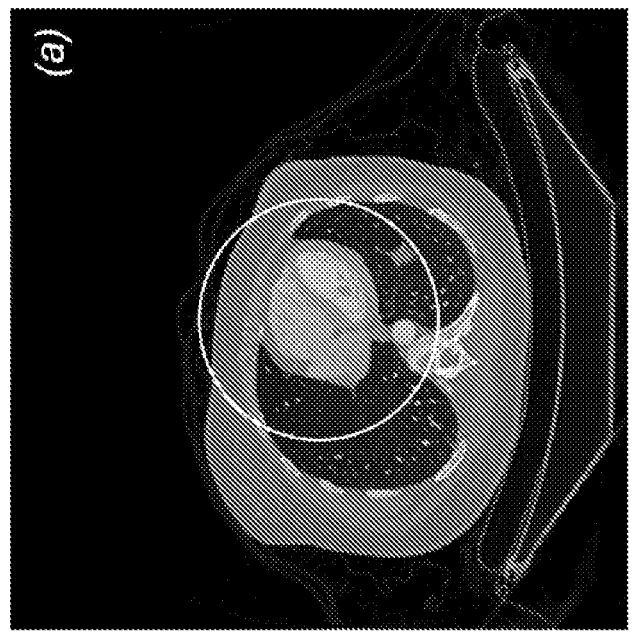

To verify the image quality of proposed cardiac CT architecture, the present inventors carried out simulation with clinical cardiac CT imaging data. The data were acquired on a commercial CT scanner (GE Discovery CT750 HD). The radius of the scanning trajectory is 538.5 mm. A total of 2200 projections were uniformly acquired over 360°. Each projection has 888 equiangular detector elements. Total variation minimization (TVM) with steepest descent search algorithm (TVM-SD) (see Yu, H. and G. Wang, *A Soft-Threshold Filtering Approach for Reconstruction from a Limited Number of Projections*. Physics in Medicine and Biology, 2010. 55(13): p. 3905-3916; Liu, B., G. Wang, E. L. Ritman, G. Cao, J. Lu, O. Zhou, L. Zeng, and H. Yu, *Image Reconstruction from Limited Angle Projections Collected by Multisource Interior X-Ray Imaging Systems*. Physics in Medicine and Biology, 2011. 56(19): p. 6337-6357) was used to reconstruct the global image (FIG. 4A). The global image serves as a benchmark to evaluate the image quality of the SSRDCT architecture. The global image has a size of 512×512 pixels and covers a FOV of 498.3×498.3 mm$^2$.

Figures 5A, 5B:
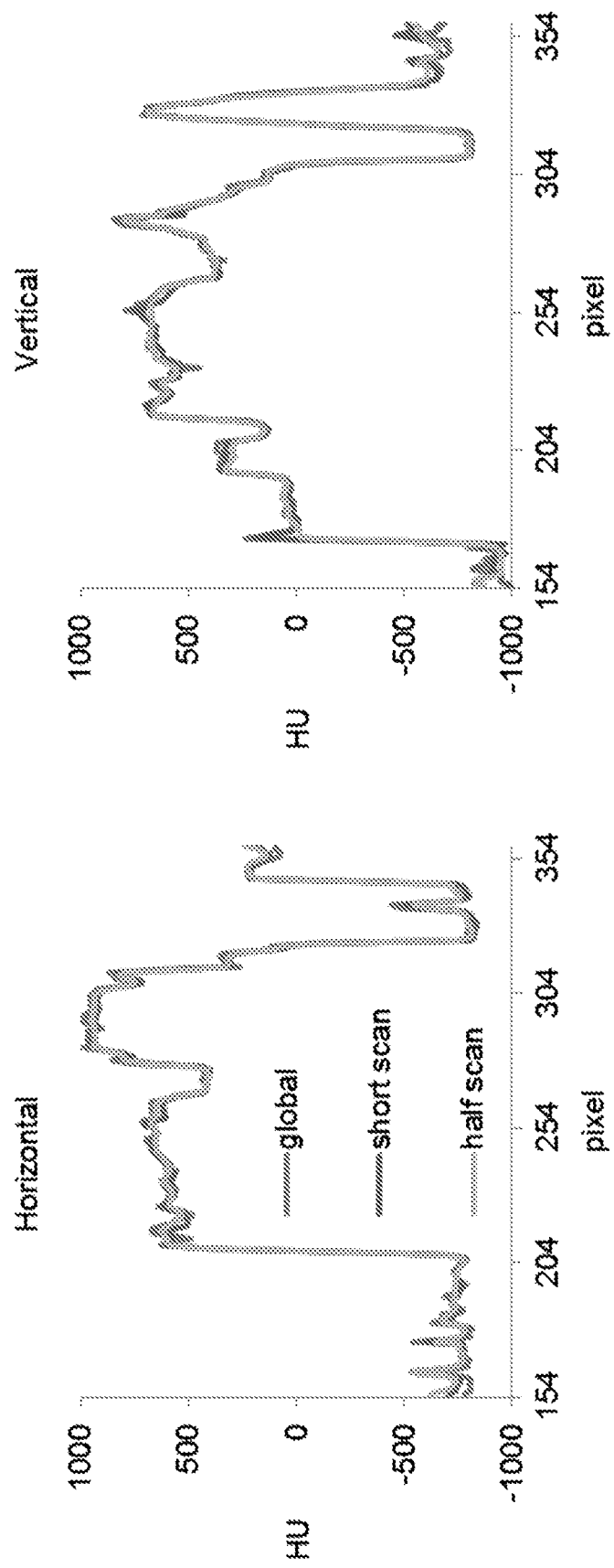
FIGS. 5A and 5B are graphs of representative line profiles of the images in FIGS. 3A-3C along the horizontal and vertical directions at the center.
Figure 6C:
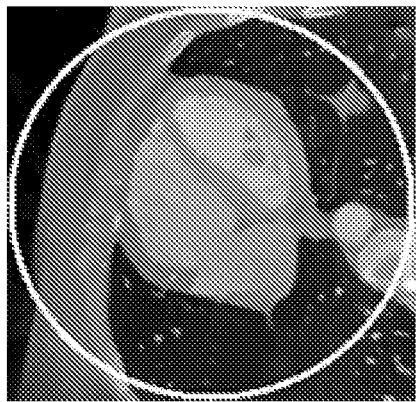
FIGS. 6A-6E show reconstructed ROI images for the half-scan mode with few views. Display window is [−1000 HU, 1800 HU]. Iteration numbers all 1000. From FIG. 6A to FIG. 6E, the total number of views are 160×3, 130×3, 100×3, 70×3, and 40×3, respectively.
Figure 6B:
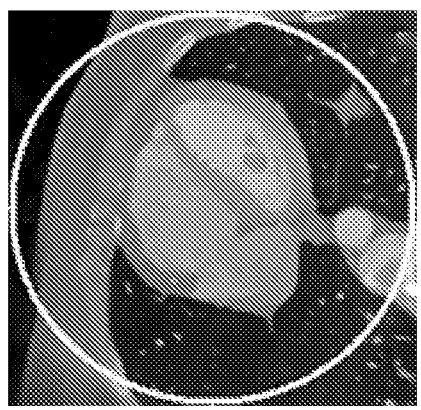
Figure 6A:
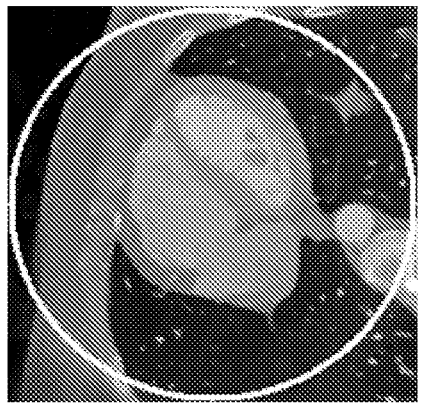
Figure 6E:
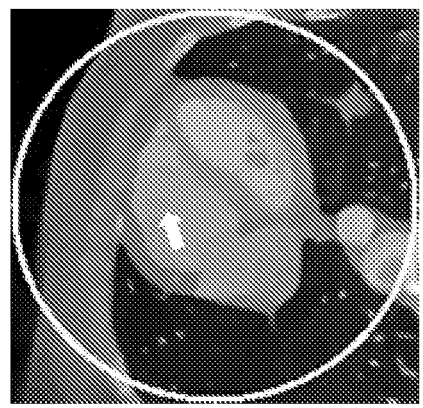
Figure 6D:
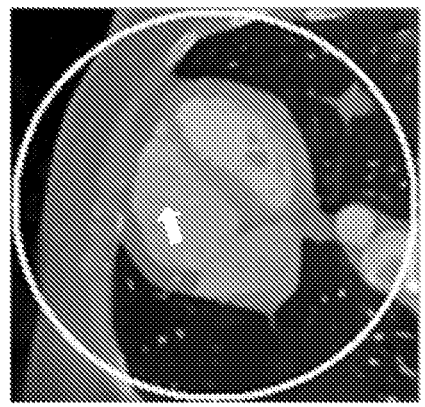

To simulate the interior-ROI-oriented data acquisition, each projection was truncated by discarding 270 detector elements from each of the two sides. This resulted in an interior ROI of 200 mm in diameter, with a corresponding fan angle at 21.4°. Therefore, for a short scan the cover angle of each source array should be 81.4°, and only the projections in [0, 81.4°], [120°, 201.4°], and [240°, 321.4°] angular ranges are needed in the SSRDCT architecture. Correspondingly, for a half scan only the projections in [0°, 60°], [120°, 180°], and [240°, 300°] angular ranges are needed. These selected projections were first truncated, and then reconstructed using the TVM-SD reconstruction algorithm. FIG. 4B and FIG. 4C show the reconstructed ROI images for the short-scan mode and the half-scan mode, respectively. FIGS. 5A and 5B show three representative line profiles along the horizontal and vertical central lines in the three images in FIGS. 4A-4C. The ROI images agree with the global image well.

TVM-SD algorithm is based on the CS theory. According to the CS theory, we can reconstruct high-quality images from limited number of projection views. Fewer views can lead to lower radiation dose. For the half-scan mode (i.e. 60° coverage angle per source array), we downsampled the projection data using the global benchmark image. The projections views for the x-ray sources in the three source arrays were equiangularly spaced in the [0, 60°], [120°, 180°] and [240°, 300°] angular ranges. The number of views per source array was set to be 160, 130, 100, 70 and 40, respectively. The corresponding reconstructed ROI images are shown in FIGS. 6A-6E. The intensity profiles along horizontal and vertical central lines are shown in FIGS. 7A and 7B, respectively. We can see that the reconstructed images from 160, 130 and 100 views per array are all qualitatively comparable with the benchmark global image, while the others lose some details as indicated by the arrows in FIGS. 6D and 6E.

Figure 8:
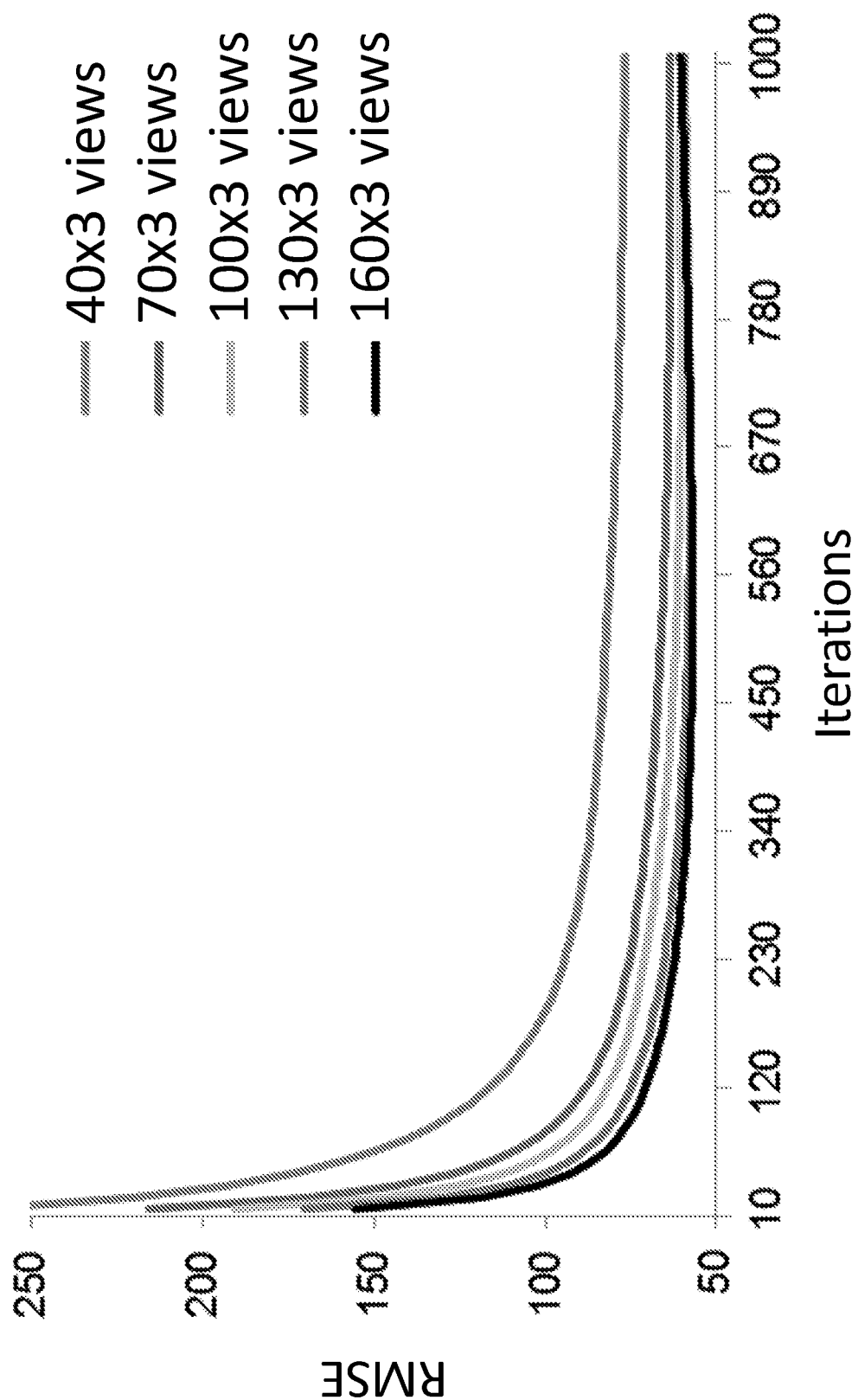
FIG. 8 is a graph plotting RMSEs vs. iterations for different numbers of views at the half-scan mode.

To quantify the quality of reconstructed images from the half-scan mode, we calculated the root-mean-square error (RMSE) in the ROI between the ROI images and the benchmark global image. The results are shown in FIG. 8. We can see that when iteration number reaches 1000, the RMSEs of 160×3, 130×3 and 100×3 views are significantly smaller than those of 70×3 and 40×3 views. Its implication for dose reduction is highly significant. If we use the result from the 100×3 views as a reference, this means that the radiation dose could be potentially reduced by a factor of 3.7.

Discussion and Conclusion

In this disclosure, the inventors present a new architecture for cardiac CT. The architecture is based on two latest advances in the CT field: the interior tomography (see Yu, H. and G. Wang, *Compressed Sensing Based Interior Tomography*. Phys Med Biol, 2009. 54(9): p. 2791-2805) and the distributed x-ray source. See Frutschy, K., B. Neculaes, L. Inzinna, A. Caiafa, J. Reynolds, Y. Zou, X. Zhang, S. Gunturi, Y. Cao, B. Waters, D. Wagner, B. D. Man, D. McDevitt, R. Roffers, B. Lounsberry, and N. J. Pelc. *High Power Distributed X-Ray Source*. 2010. 7622. SPIE; Sprenger, F., X. Calderon, E. Gidcumb, J. Lu, X. Qian, D. Spronk, A. Tucker, G. Yang, and O. Zhou. *Stationary Digital Breast Tomosynthesis with Distributed Field Emission X-Ray Tube*. 2011. 7961. SPIE. The feasibility of the architecture was explored via numerical analyses and carried out simulations using clinical cardiac CT data. The results indicate that the architecture has potential to perform cardiac CT with 50 ms temporal resolution and significantly reduced radiation dose.

The improvement in temporal resolution can be more easily appreciated when compared to the two previously tested approaches—DSR and EBCT. For the DSR, fast temporal resolution was obtained by increasing the number of source-detector chains. For the EBCT, it was achieved primarily through a stationary x-ray source. Firstly, the inventive architecture features three source-detector chains. The three source-detector chains are expected to boost the temporal resolution in a similar fashion to the DSR (see Ritman, E. L., J. H. Kinsey, R. A. Robb, B. K. Gilbert, L. D. Harris, and E. H. Wood, *3-Dimensional Imaging of Heart, Lungs, and Circulation*. Science, 1980. 210(4467): p. 273-280; Ritman, E. L., L. D. Harris, J. H. Kinsey, and R. A. Robb, *Computed Tomographic Imaging of the Heart: The Dynamic Spatial Reconstructor*. Radiol. Clin. North. Am., 1980. 18(3): p. 547-555; Ritman, E. L., R. A. Robb, and L. D. Harris, *Imaging Physiological Functions: Experience with the Dsr*1985: Philadelphia: Praeger), in that the temporal resolution will be speeded up by simultaneous data acquisition from the multiple source-detector chains. Secondly, the three sources in our architecture are stationary. The stationary sources will deliver the same benefit as that in the EBCT (see M. J. Lipton, C. B. Higgins, D. Farmer, and D. P. Boyd, *Cardiac Imaging with a High-Speed Cine-Ct Scanner: Preliminary Results*. Radiology, 1984. 152(3): p. 579-582), because the source-points can be swept electronically with far greater speed compared to being spun mechanically. Additionally, by removing the sources from the rotating gantry, the weight on the gantry will be reduced, which would allow a shorter gantry rotation time (i.e. Trot) and hence an even faster temporal resolution.

The reduction in radiation dose comes from the few-view interior-ROI orientated CT sampling and the CS-based reconstruction algorithm. The few-view interior-ROI orientated CT sampling is highly synergistic with and can be easily realized by the distributed sources in the proposed architecture. It allows not only a narrower beam but also a less angular sampling requirement. The smaller an ROI is, the narrower the beam will be, and the less radiation. Narrower beams also reduce photon scattering, which improves contrast. The fewer views a CT scan acquires, the fewer number of x-ray beam assemblies will be required in the three distributed x-ray sources, hence lower construction cost for the sources. The distributed x-ray sources allow switching instantaneously and precisely on and off the x-ray beams that correspond to the few views during a CT scan, thus eliminating unnecessary x-ray exposures at the other views and saving radiation dose. In comparison, the dose reduction benefit from the few-view CT sampling is hardly realized with the conventional x-ray sources in the current CT architectures, because the sources are on continuously during the data acquisition for a single slice image.

The inventive stationary CT architecture is expected to achieve the stated performance while avoiding some known drawbacks in the DSR and EBCT. The DSR had to employ a large gantry to mount multiple source-detector chains, primarily due to the bulky x-ray tubes and large detectors. Consequently, the DSR system came with large size and high cost, and only one such system was ever built. The EBCT has an anode ring that encloses the patient. To steer an electron beam to impede on such a large ring, the EBCT system also came with large size and high cost. In comparison, the inventive architecture can be realized on a conventional CT gantry, owing to the tightly integrated x-ray source arrays and the smaller detectors. The resulted system will be much more compact and is expected to have a size similar to the current CT scanners. Furthermore, the EBCT is also known for its other drawbacks caused by a stationary detector. A stationary detector requires an offset in the z-direction (between the source plane and the detector plane) to cover a typical scan angle of 220°, thus no anti-scatter collimator can be used. This drawback could be avoided in the inventive architecture, because the detectors are co-planar to the sources and rotate synchronously to the sweeping source-points driven by both the electronic switching and the local steering (i.e. steering the electron beam to impinge a short focal track on the fixed anode).

The inventive architecture, due to its small FOV (200 mm), is ideal for cardiac-region-specific diagnostic tasks such as identifying atherosclerotic plaques. The potential in faster temporal resolution and lower radiation dose is especially attractive for cardiac CT perfusion imaging.

In addition to the specific type in FIG. 2, the inventive architecture may have other variants. One embodiment uses a stationary ring source that covers a full circle. This will make a 360° full-scan possible, but will come with higher cost on the source and require each detector to rotate at least 120° and hence slower temporal resolution. Another embodiment uses linear source arrays instead of curved source arrays. This will lead to geometrical non-uniformity from view to view, but could lead to lower construction cost for the sources. The inventive CT architecture may use a commercial CT x-ray source or a carbon nanotube (CNT) CT x-ray source. Further the CNT CT x-ray source may be single-beam source or a multi-beam array. Still further, the inventive CT architecture may use robust Few-view Interior Tomography (FIT) methods as reconstruction algorithms. The reconstruction algorithms may include a dictionary-based sparsity constraint based in part on Equations C.2-1 and C.2-2 as described in the "Dictionary-based Sparse Representation" section of the Examples.

Omni Tomography System with a Stationary CT Subsystem

In consideration of a design for a CT-MRI scanner, a rotating x-ray source and detector can interfere with MRI imaging. To this end, another embodiment of the invention is an interior CT-MRI scanner that uses a stationary CT architecture in which multiple x-ray sources are placed around a patient, along with the corresponding detector pieces. All the x-ray beams focus on an ROI, representing a few-view imaging setup. Currently, for satisfactory image reconstruction, a large number of projections is needed, however, in the fused CT-MRI scanner the synergy between CT and MRI data can be utilized to reduce the number of x-ray projections greatly. If the CT subsystem is not moving, the electromagnetic shielding for the MRI subsystem can be simplified.

Figure 9:
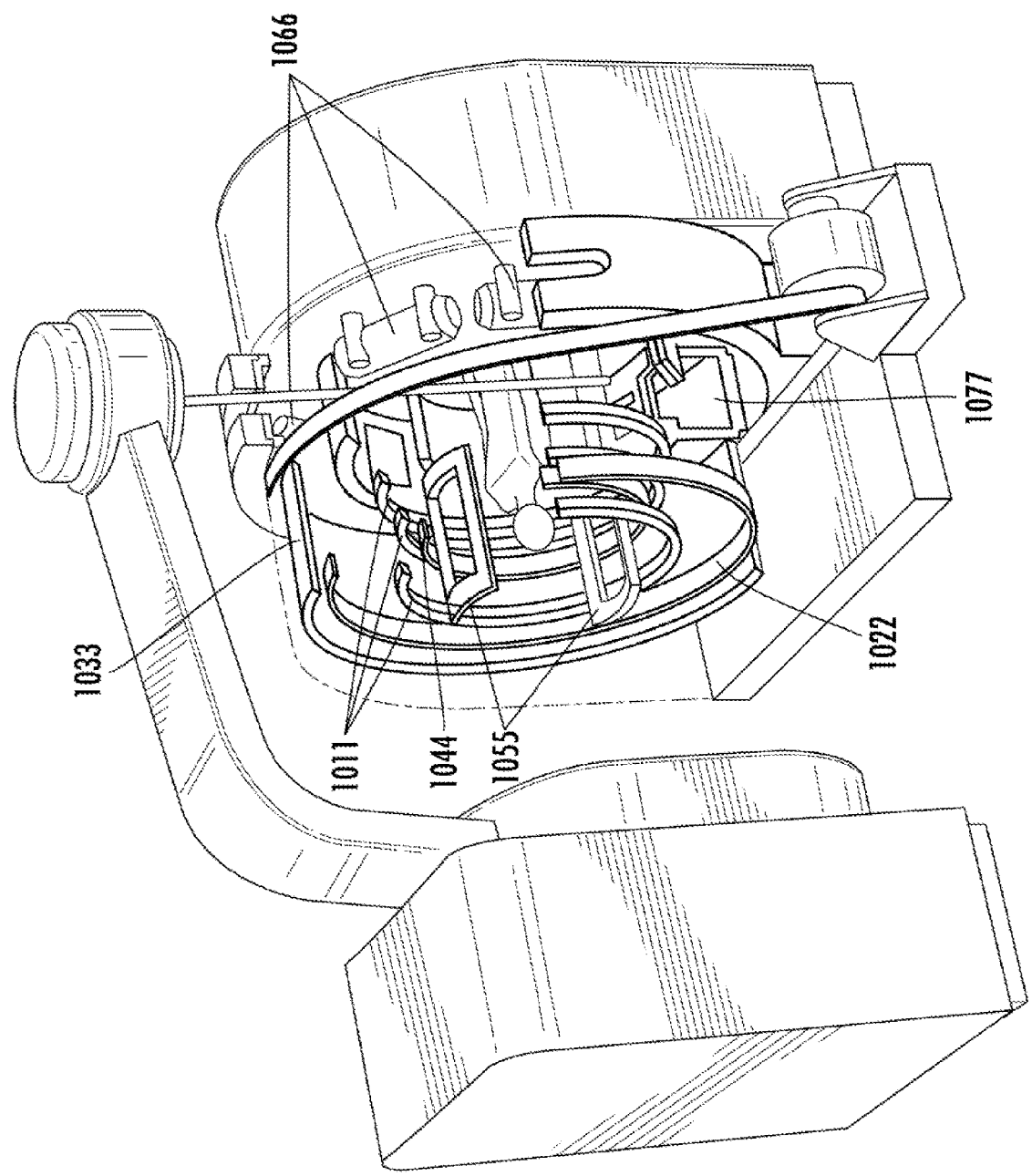
FIG. 9 is a schematic diagram showing a front right view of an embodiment of a synchronized computed tomography (CT) and MRI scanner. Shown are the coil blocks of the superconducting MRI magnet's primary layer 1011 and shielding layer 1022, a cryostat 1033 of the superconducting MRI magnet, longitudinal 1044 and transverse 1055 gradient coils, x-ray sources 1066, and x-ray detectors 1077. The coil blocks of the superconducting magnet provide a uniform static magnetic field over a small region of interest, while the gradient coils enable MRI spatial encoding. A multi-source interior tomography scheme is used for CT image reconstruction.

FIG. 9 is a schematic diagram showing a front right view of an embodiment for a synchronized computed tomography (CT) and MRI scanner. Shown are the coil blocks of the superconducting MRI magnet's primary layer 1011 and shielding layer 1022, a cryostat 1033 of the superconducting MRI magnet, longitudinal 1044 and transverse 1055 gradient coils, x-ray sources 1066, and x-ray detectors 1077. The coil blocks of the superconducting magnet provide a uniform static magnetic field over a small region of interest, while the gradient coils enable MRI spatial encoding. A multi-source interior tomography scheme is used for CT image reconstruction. This embodiment may be modified to include the stationary CT architecture of the invention at the position of the x-ray sources and x-ray detectors.

Figure 10A:
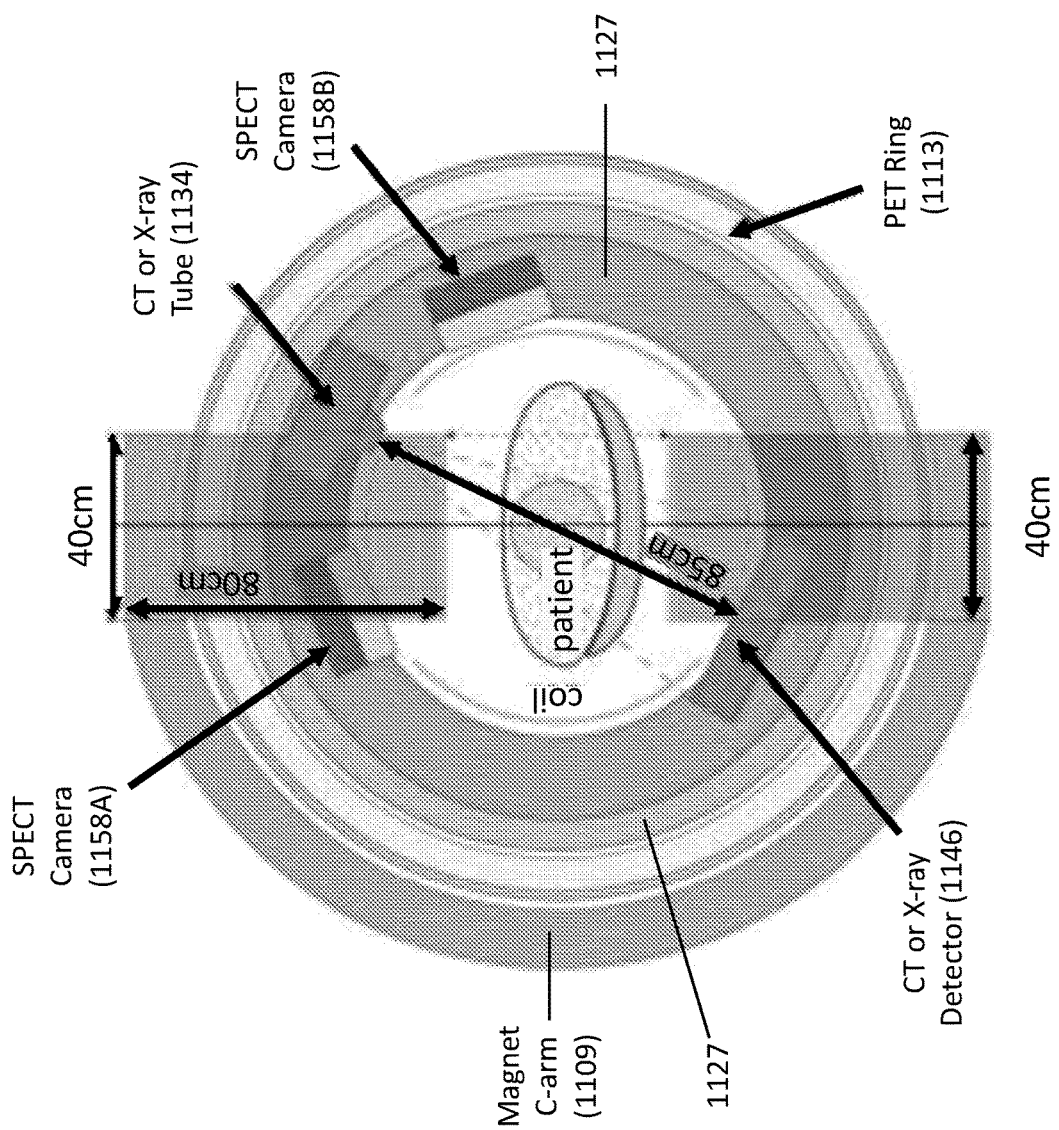
Figure 10B:
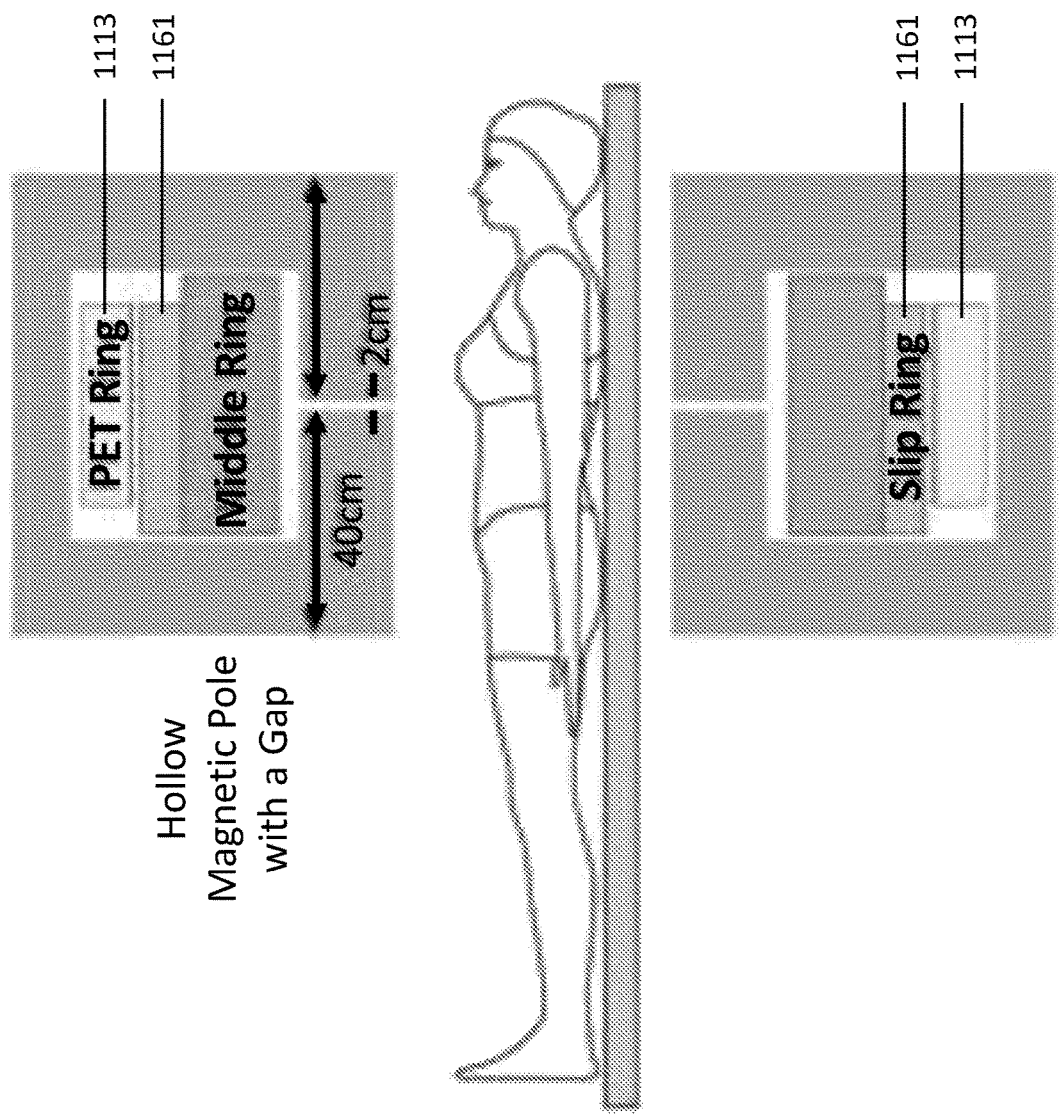

Further, the omni-tomography embodiments of the invention are not limited to a CT-MRI system, but may include other modalities, including one or more modalities chosen from PET, SPECT, Ultrasound and optical imaging subsystems. FIGS. 10A-B show an embodiment of the ring-shaped design for omnitomography using multiple modalities, wherein the top-level design, FIG. 11B shows a partial rendering, FIG. 11C FIG. 10A shows an in-plane view and FIG. 10B shows a through-plane view. There are two static rings and one rotating ring for omnitomography. While the C-arm 1109 is a permanent magnet and the outer ring 1113 contains PET crystals, ring 1127 supports a CT tube 1134 (or x-ray tube), a CT detector 1146 (or x-ray detector) and a pair of single-photon emission computed tomography (SPECT) cameras 1158A and 1158B. The CT-SPECT ring 1127 is on a slip ring 1161 (like a large ball bearing) as the interface for power and data. The CT-SPECT ring 1127, the slip ring 1161, and the PET ring 1113 all go through the magnetic poles. This embodiment may be modified to include stationary CT architecture of the invention.

All the major medical tomographic modalities are incorporated into three concentric rings: an inner ring as a permanent magnet; a middle ring containing the x-ray tube and detector array and a pair of SPECT detectors; and an outer ring for PET crystals and electronics (inner and outer rings are preferably static). The middle ring is designed to rotate and acquire data for both interior CT and interior SPECT. This rotating ring is embedded in a slip-ring (similar to a large diameter ball bearing) which supports the rotating ring and facilitates power/signal transmission. The rotating ring, the slip-ring, and the PET ring all go through the magnetic poles. The yoke for N and S poles of the magnet are configured similarly to a "C arm". The system is designed for human or animal subjects, and can be configured to accommodate a standard patient size (approximately 170 cm in height, 70 kg, with a chest size of 22 cm in AP direction and 35 cm in lateral direction).

The following disclosure discusses the MRI subsystem of the omni-tomography system of the invention. However, discussion of other subsystems and their integration in an omni-tomography system can be found in US Patent Application Publication No. 2012/0265050 A1, the disclosure of which is hereby incorporated by reference in its entirety.

MRI

In some embodiments, the MRI component of the interior CT-MRI scanner may be similar to that of a commercial open MRI. All the available techniques for open MRI can be potentially adapted for the stationary CT-MRI scanner. The MRI subsystem can consist of two permanent magnet heads at each magnetic pole. The vertical gap between the magnet poles can be about 50 cm and in this case was chosen based on a simulation to provide a sufficient magnetic field for a region of interest (ROI) of approximately 15 to 20 cm in the center of the gantry aperture. This ROI was also used to determine the width (40 cm) and length (2×40 cm) of the magnetic heads. This configuration leaves sufficient space for other modalities to probe the subject without being significantly blocked by the magnet. A deviation from the commercial open MRI design is that each magnet head is hollow and has a gap to let the middle ring modalities "look through" the magnet. Hence, the CT tube and detector, as well as the SPECT cameras, perform full-scans to the extent defined by the gap through the magnet, and cone-beam scans when the magnet is not in the radiation paths. This detailed design for the magnet permits a 2 cm clearance between the two magnet parts of each pole.

Vizimag software can be used to simulate the field strength of the magnetic field and realize a locally uniform field between the poles. In a simulation performed to determine optimum parameters for the MRI component of the omni-tomographic system, the desired magnetic field strength was set to 0.2 Tesla. The magnetic field may be adjusted by changing ferromagnetic materials and the dimensions of the magnetic blocks or using an alternative technology. The magnetic flux varies from 0.208 to 0.211 Tesla over as ROI of 20×20 $cm^2$ with its origin at the iso-center of the main imaging plane in the omni-tomographic imager. The field uniformity can be further improved with technical refinements. Further, one of skill in the art will know how to adjust the parameters to achieve a desired effect and indeed any of the MRI systems known in the art can be incorporated into the omni-tomography systems of the invention. Likewise, any of the technical specifications provided in references cited in this specification can be used to obtain an MRI modality compatible with the omni-tomography systems according to the invention.

The gradient coils used with current open MRI scanners can be modified for integration into the inventive CT-MRI scanner. Generally speaking, any gradient and RF coil settings for open MRI can be used in the inventive systems. See C H Moon, H. W. P., M H Cho and S Y Lee, Design of convex-surface gradient coils for a vertical-field open MRI system. Meas. Sci. Technol., 2000. 11(8): p. N89-N94; and While, P. T., L. K. Forbes, and S. Crozier, 3D gradient coil design for open MRI systems. Journal of Magnetic Resonance, 2010. 207(1): p. 124-133.

MRI shielding is preferred for the architecture, including: radio frequency interference shielding, electromagnetic interference shielding, electromagnetic pulse shielding, and so on. Highly conductive, non-woven electromagnetic shielding materials will be used for this purpose. These materials are usually made from a variety of fibers, such as carbon and nickel-coated carbon, which are flexible enough to accommodate complex contours and shapes. These techniques are well-developed or maturing, and should not pose significant difficulty in principle. See Laskaris, E. T., Open MRI magnet with superconductive shielding. 1995, General Electric Company: United States.

In other embodiments, the MRI sub-system uses a highly sophisticated superconducting electromagnet technology. The performance of the paired superconducting magnets is critical to image quality. The static field produced by the magnets in the field of view is relaxed to be much smaller than the counterpart for a conventional MRI scanner, and needs to be strong and nearly perfect (a few parts-per-million (ppm) variation) only throughout a cardiac ROI. This represents a major simplification relative to the requirements for a much larger conventional field of view. The design of the split architecture with a large central gap (more than 40 cm) is challenging, demanding the full consideration of the electromagnetic, mechanical and thermal properties of all the involved components.

In embodiments, the MRI subsystem includes a superconducting MRI magnet with a two-layer coil configuration. The first layer with a small radius (50 cm) provides a primary magnetic field in the field of view, while the second layer with a large radius (80 cm) is mainly for shielding the stray magnetic field within the domain of interest (8 m in length and 5 m in radius). The magnet design offers a 1.5 T field of view of an appropriate diameter (25 cm), which defines a spherical field of view. The field uniformity inside the spherical field of view is 1 ppm (peak-peak). This magnet design allows the integration of stationary CT in the gap between the pair of magnets, and allows the current 1.5 T MRI performance can be achieved. Temporal resolution can be initially set to 20-60 ms or less. In-plane spatial resolution can be specified at 1-2 mm, which is adequate for most cardiac function studies, although higher spatial resolution is possible when CT-based motion correction techniques are developed.

The inventive CT-MRI scanner is particularly useful for cardiac diagnostic and therapeutic applications. Diagnostic applications include the analysis of atherosclerotic plaques. With enhanced features and additional modalities, the scanner may be used to investigate many features of vulnerable plaques, including cap thickness, lipid-core size, stenosis, calcification, hemorrhage, elasticity, inflammation, endothelial status, oxidative stress, platelet aggregation, fibrin deposition, enzyme activity, microbial antigens, apoptosis, and angiogenesis. Further, non-cardiac diagnostic applications are possible, including imaging brain injuries and other brain traumas, and evaluating acute strokes in the emergency room, when time is critical. Cardiac therapeutic applications include the delivery of drugs or stem cells, or guidance of complicated procedures such as heart valve replacement. These are only examples of applications of the technology, with additional uses apparent to the skilled artisan.

Additional aspects of the design of the stationary CT architecture can be found in the foregoing Examples, which are intended to teach certain features of the invention and should not be construed as limiting the invention.

EXAMPLES

Cardiovascular computed tomography (CVCT) has been successfully applied for the diagnosis of a series of heart diseases. However, the limitations of temporal and spatial resolution and radiation dose inhibit the utilization of CVCT for more clinical applications. The specific primary bottlenecks of the current CVCT include the difficulties of the synchronization with high or arrhythmic heart rates, the inability to measure blood flow, the detection of vulnerable plaques, the separation of calcium from iodine signals, the study of myocardial micro-vascular structure and perfusion, as well as the risk of ionizing radiation exposure. The recent technical innovations in the fields of x-ray sources and reconstruction methods indicate the immense potential for CVCT advancement. An innovative cardiac CT architecture is provided to overcome these obstacles, which systematically integrates carbon nanotube (CNT) x-ray sources and interior tomography methods. This novel architecture can provide for unprecedented capability for in vivo tomographic, morphologic and physiologic measurement.

In developing and validating a STationary-source Rotatory-detector Interior CT (STRICT) architecture, several considerations can be taken into account, including: (1) CNT x-ray sources for CT of clinically relevant animal models and human patients; (2) few-view interior tomography methods addressing low-dose scanning and physiological signals; (3) an interior CVCT system prototype using stationary CNT arrays and rotating detectors; and (4) ex vivo pig heart preparations and pig models to create myocardial infarcts and re-perfusion injury, specify the position and size of various lesions, and image plaques and perfusion.

Taken together, the stationary source technology and interior reconstruction algorithm can promote the major changes from wide-detector-based architectures to local-scanning-oriented systems, from single x-ray sources to distributed x-ray sources, from conventional global reconstruction to contemporary interior reconstruction, and towards much-enhanced and newly enabled preclinical and clinical applications. The inventors' novel CVCT prototype is expected to contribute greatly to the preclinical and clinical research using ex vivo samples and in vivo human-sized animal models (pigs), which allow rapid translation for clinical healthcare. Compared with the state-of-the-art CT, such a CVCT prototype will not only achieve higher temporal resolution (<50 ms) and higher spatial resolution (~0.4 mm), but also enable the interior tomography with 20 cm ROI diameter (organ-targeted scanning), for human-sized animal models at lower radiation dose (sub-mSv).

The first-of-its-kind ultrafast cardiovascular CT (CVCT) prototype can be operably configured to double both acquisition speed and work at minimized (sub-mSv) radiation dose. The CVCT prototype can be applied in translational studies with human-sized animal models of human cardiovascular disease and intervention.

Design of a stationary-source CT system and its feasibility analysis.

Design of a STRICT system. First, the conceptual system architecture and the corresponding scan protocol can be developed based on the industrial standard. Second, the approaches of system simulation and evaluation should be developed with our expertise and the main-stream counterpart. The detailed specification of each module will be refined progressively throughout the whole project.

Optimization of the STRICT architecture. A test-bed with the commercial CT x-ray source can be constructed to simulate and evaluate the STRICT system architecture and scan protocol proposed in the conceptual design. It can also be used to establish a reference for characterizing the cutting-edge components (e.g. the CNT source array).

Development of reconstruction algorithms. To reduce radiation dose, robust Few-view Interior Tomography (FIT) methods can be developed with a dictionary-based sparsity constraint. The FIT methods can evolve from the state-of-the-art algorithms such as prior image constrained compressed sensing (PICCS) and cardiac motion compensation. The FIT algorithms can also be accelerated via high-performance computing to enable real-time image reconstruction.

Development and characterization of a CNT source with sweeping electron beam, such as an open-chamber single-beam CNT source. The CNT source technology has been successfully applied in preclinical and clinical studies where relatively low flux is sufficient. CNT x-ray sources of high flux sufficient for cardiac CT imaging can be developed based on clinical standard. The target maximum x-ray tube voltage is 120 kVp. The maximum anode current is 100 mA. To prevent local overheating at the focal spot, the high-current electron beam can be swept across a short (~10 mm) and distinctive focal track on the anode via electrostatic deflection.

The single-beam CNT prototype source can be characterized (e.g. voltage/current level, reliability, focal spot size, and lifetime). The CNT source can be integrated into the test-bed for performance assessment in the STRICT architecture.

Development and evaluation of a CNT source array in the STRICT architecture. Scaling up from single-beam source to multi-beam source array can be achieved by building a compact 33-beam linear CNT x-ray source array based on the design for the single-beam CNT source discussed above.

STRICT System integration and phantom characterization. The 33-beam CNT source array can be integrated into the test-bed for further performance conditioning and evaluation. Second, the CNT source array can be gradually upgraded with larger number of x-ray beams. Then, the 33-beam source can CT scan physical phantoms to assess image quality. Here phantoms can be rotated.

Translational studies in human-sized animals. Translational cardiac injury studies can be conducted with ex vivo heart preparations and pig models to create myocardial infarcts and re-perfusion injury (MI/RPI), to specify the position and size of various lesions, and to image plaques and perfusion. A full CT data acquisition can consist of three cardiac-gated scans, with the source array stepping through the three angular positions of the three stationary source arrays in the STRICT architecture.

CVCT prototype constructed according to embodiments of the invention can be designed such that they are capable of achieving one or more of the following performance criteria: ≤50 ms temporal resolution (doubling speed, at which no β blocker is required for most human scans, and for pig scans with/without β blockers); ~0.4 mm spatial resolution (doubling precision, for advanced analysis and modeling), 20 cm ROI diameter (focused scanning), 50 cm bore diameter (human-sized animals), and with sub-mSv dose.

Biomedical Background—Cardiac Computed Tomography (CT) provides a noninvasive method for the clinicians and the scientists to obtain the detailed anatomical structure of the beating heart, evaluate functional cardiac disorder, and even diagnose the possible cardiac infarction or plaque in its early stage. In comparison with other typical techniques such as Echocardiography, SPECT, and Cardiac MRI, Cardiac CT, with its high spatial resolution, is often preferred in evaluating the suspected coronary anomalies. See Atalay, M. K., Cardiac Magnetic Resonance Imaging and Computed Tomography—State of the Art. US Radiology, 2011. 1(1): p. 34-39. The world health organization predicts that Cardiovascular disease (CVD) will remain the leading cause of death with 20 million deaths in 2015, accounting for 30 percent of all deaths worldwide. See WHO. Preventing Chronic Diseases: A Vital Investment. 2005 [cited 2012 Apr. 25]. The utilization of Cardiac CT is expected to rise with growth rate >10% per year and thus the collective X-ray exposure to the population will be further increased. See Brenner, D. J. and E. J. Hall, Computed Tomography—an Increasing Source of Radiation Exposure. N Engl J Med, 2007. 357(22): p. 2277-2284. The development of Cardiac CT with lower radiation exposure and higher efficiency is urgent and significant for the public health.

On the other side, X-ray CT is increasingly utilized in the preclinical imaging to study the animal models of human diseases and intervention. The small animal models are largely used to link the genomic and epigenetic signatures with the phenotypic expression. The micro-imaging techniques have been extensively developed to study the small animal models. Compared to small-animal models, however, the human-sized animal models enable the scientists to do much more clinically relevant modeling. Therefore, there is currently more emphasis given to the development of the human-sized animal imaging techniques. Our team has extensive expertise and unique facilities for studying valuable translational animal models such as pigs, dogs, and non-human primates (macaques). This R01 will be focused on the development of innovative Cardiac CT and its application with the clinically translational models of the human-sized animals.

Technical Challenges—With the advancement of the clinical and non-clinical applications of CT, there are several well-recognized technical challenges. See Wang, G., H. Yu, and B. De Man, An Outlook on X-Ray Ct Research and Development (Invited Paper). Medical Physics, 2008. 35(3): p. 1051-1064. First, scanning speed has become a major limitation of CT in cardiac imaging, dynamic contrast enhanced studies, and image-guided interventions. For instance, the state-of-the-art dual-source CT scanner can only achieve the highest temporal resolution of ~80 ms with ECG gating for stable cardiac phases. See Achenbach, S., D. Ropers, A. Kuettner, T. Flohr, B. Ohnesorge, H. Bruder, H. Theessen, M. Karakaya, W. G. Daniel, W. Bautz, W. A. Kalender, and K. Anders, Contrast-Enhanced Coronary Artery Visualization by Dual-Source Computed Tomography—Initial Experience. European Journal Of Radiology, 2006. 57(3): p. 331-335; Flohr, T. G., C. H. McCollough, H. Bruder, M. Petersilka, K. Gruber, C. Suss, M. Grasruck, K. Stierstorfer, B. Krauss, R. Raupach, A. N. Primak, A. Kuttner, S. Achenbach, C. Becker, A. Kopp, and B. M. Ohnesorge, First Performance Evaluation of a Dual-Source Ct (Dsct) System. European Radiology, 2006. 16(2): p. 256-268; Johnson, T. R. C., K. Nikolaou, B. J. Wintersperger, A. W. Leber, F. von Ziegler, C. Rist, S. Buhmann, A. Knez, M. F. Reiser, and C. R. Becker, Dual-Source Ct Cardiac Imaging: Initial Experience. European Radiology, 2006. 16(7): p. 1409-1415; Kachelriess, M., M. Knaup, and W. A. Kalender, Multithreaded Cardiac Ct. Medical Physics, 2006 33(7): p. 2435-2447; Scheffel, H., H. Alkadhi, A. Plass, R. Vachenauer, L. Desbiolles, O. Gaemperli, T. Schepis, T. Frauenfelder, T. Schertler, L. Husmann, J. Grunenfelder, M. Genoni, P. A. Kaufmann, B. Marincek, and S. Leschka, Accuracy of Dual-Source Ct Coronary Angiography: First Experience in a High Pre-Test Probability Population without Heart Rate Control. European Radiology, 2006. 16(12): p. 2739-2747. However, the temporal resolution less than ~50 ms is generally considered to be necessary for the patients with high and arrhythmic heart rates. In the study of animal models, cardiac imaging may require much higher temporal resolution due to the faster heart rates. Second, the spatial resolution of CT also becomes a bottleneck in many applications. For example, the best spatial resolution of Cardiac CT is currently ~1 mm due to the motion blurring, which inhibits the precise distinguishing of the soft vascular plaque from the hard one. Third, the radiation exposure needs to be further reduced, especially in the case of pediatric CT. According to a British study, the radiation exposure of X-ray from medical use is suspected as the cause of ~700 cases of cancer per year in UK and >5600 cases per year in US. See Berrington de Gonzalez, A. and S. Darby, Risk of Cancer from Diagnostic X-Rays: Estimates for the Uk and 14 Other Countries. Lancet, 2004. 363(9406): p. 345-351. To reduce the risk of carcinogenesis, the "As Low As Reasonably Achievable" principle has been accepted, as is the more recent and well-known "Image Gently" campaign (www.imagegently.org).

Invention Significance—Current CT tubes are all single-point x-ray source; scanning x-ray radiation is emitted from only one focal spot. During cardiac CT image acquisition, the x-ray tube is typically mechanically rotated and subjected to a g-force of ~30 g (see Schardt, P., J. Deuringer, Jr., Freudenberger, E. Hell, W. Knüpfer, D. Mattern, and M. Schild, New X-Ray Tube Performance in Computed Tomography by Introducing the Rotating Envelope Tube Technology. Medical Physics, 2004. 31(9): p. 2699; Kalender, W., Computed Tomography: Fundamentals, System Technology, Image Quality, Applications. 2nd ed. 2005, Erlangen: Publicis Corporate Publishing); both lead to source complexity, electron beam focusing in particular. This rotating-source architecture represents the major hurdle for increasing the temporal resolution and reducing the radiation dose. A CT architecture employing stationary source can bypass this hurdle and achieve the electron-beam CT (EBCT)-like performance. On the other hand, current CT architectures have been equipped with the large detector array covering a full trans-axial extent of the patient, yet the local anatomical structures (such as the heart) are the only region of interest (ROI) in many clinical cases. The utilization of interior tomography eliminates the undesired radiation exposure and the necessity of using the large detector array.

Taken together, the stationary source technology and interior reconstruction algorithm can promote the major changes from wide-detector-based architectures to local-scanning-oriented systems, from single x-ray sources to distributed x-ray sources, from conventional global reconstruction to contemporary interior reconstruction, and towards much-enhanced and newly enabled preclinical and clinical applications.

Distributed CNT Sources—The development of CNT x-ray sources has become one innovative direction in the research of CT, since the traditional x-ray source techniques have reached the performance limits. CNT x-ray sources are "cold" electron sources in comparison with the conventional counterparts. See Zhou, O. and X. Calderon-Colon, Carbon Nanotube Based Field Emission X-Ray Technology, in Carbon Nanotube and Related Field Emitters: Fundamentals and Applications, Y. Saito, Editor 2010. In CNT sources, the x-ray tube current is generated by the bias voltage between a gate electrode and a CNT cathode. The x-ray radiation can also be programmed with an external trigger signal. Because of its smaller size, a densely distributed x-ray source array can be built by using multi-pixel CNT cathodes. See Zhang, J., G. Yang, Y. Cheng, B. Gao, Q. Qiu, Y. Z. Lee, J. P. Lu, and O. Zhou, A Stationary Scanning X-Ray Source Based on Carbon Nanotube Field Emitters. Appl. Phys. Lett., 2005. 86: p. 184104.

Figure 11:
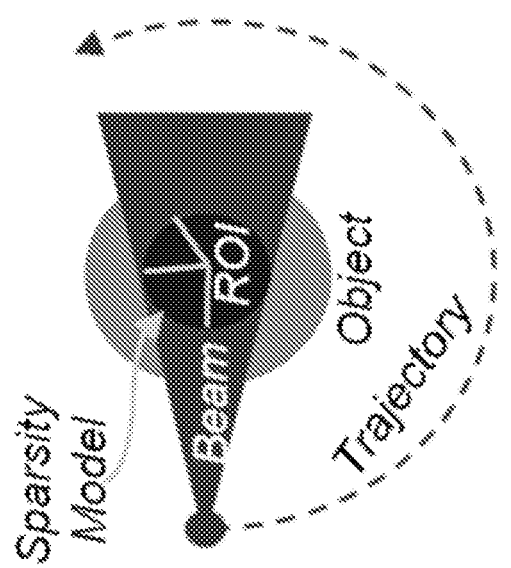
FIG. 11 is a diagram showing the Sparsity-based Interior tomography.
Figure 12B:
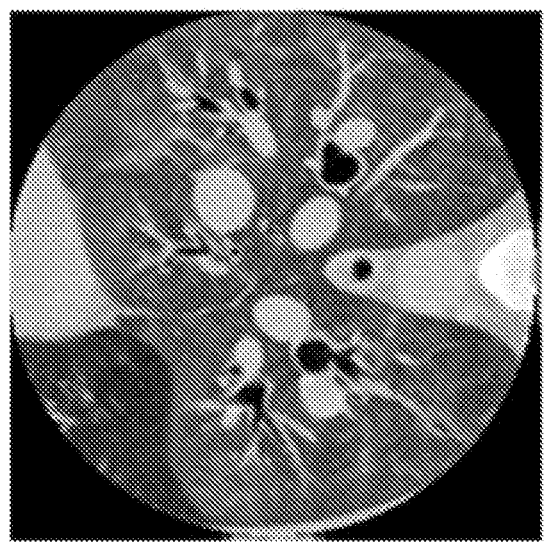
Figure 12A:
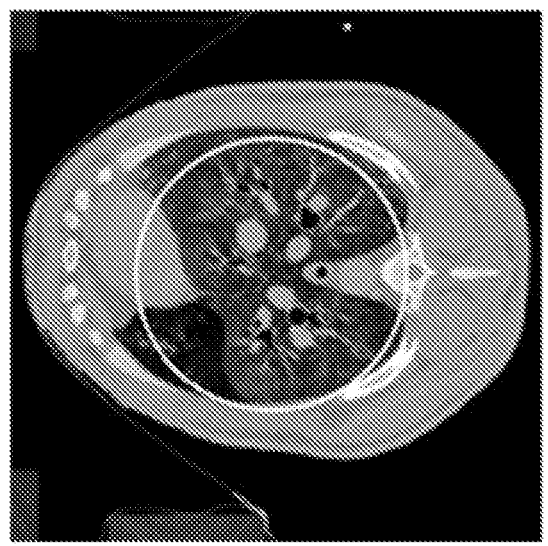

Interior Tomography—Although conventional CT aims at the reconstruction of the complete cross-section or the entire volume of the objects, the practical clinical applications frequently requires the investigation on a small ROI. The instant benefits of interior tomography include imaging the objects larger than the field of view (FOV), enhancing the scanning speed and the data transfer rate, and reducing the unnecessary radiation exposure to the region outside ROI. The challenges of the application of interior tomography derive from the fact that conventional CT methods cannot precisely reconstruct an interior region with the truncated projections only from the x-rays through the ROI. This fact also leads to the current commercial CT architecture with a long detector array intercepting a wide x-ray beam. Since 2007, interior tomography developments have been made (see Ye, Y., H. Yu, Y. Wei, and G. Wang, A General Local Reconstruction Approach Based on a Truncated Hilbert Transform. International Journal of Biomedical Imaging, 2007. 2007: p. Article ID: 63634, 63638 pages; Ye, Y., H. Yu, and G. Wang, Exact Interior Reconstruction with Cone-Beam Ct. International Journal of Biomedical Imaging, 2007. 2007: p. Article ID: 10693, 10695 pages; Ye, Y., H. Y. Yu, and G. Wang, Exact Interior Reconstruction from Truncated Limited-Angle Projection Data. International Journal of Biomedical Imaging, 2008. 2008: p. Article ID: 427989, 427986 Pages; Yu, H. and G. Wang, Compressed Sensing Based Interior Tomography. Phys Med Biol, 2009. 54(9): p. 2791-2805; Yu, H., J. Yang, M. Jiang, and G. Wang, Supplemental Analysis on Compressed Sensing Based Interior Tomography. Phys Med Biol, 2009. 54(18): p. N425-N432; Wang, G., Y. Ye, and H. Yu, Interior Tomography and Instant Tomography by Reconstruction from Truncated Limited-Angle Projection Data; U.S. Pat. No. 7,697,685, 2010; Yang, J. S., H. Y. Yu, M. Jiang, and G. Wang, High-Order Total Variation Minimization for Interior Tomography. Inverse Problems, 2010. 26(3): p. 29; Katsevich, G., A. Katsevich, and G. Wang, Stability of the Interior Problem with Polynomial Attenuation in a Region of Interest. Inverse Problems, 2012) toward precise reconstruction of an ROI with purely local projections (FIG. 11). This work developing the reconstruction algorithms for interior tomography has produced convincing results with the real animal CT data (FIGS. 12A and 12B). Moreover, the interior tomography approach has been extended for electron-beam tomography (see Wang, G. and H. Yu, Can Interior Tomography Outperform Lambda Tomography? Proc Natl Acad Sci USA, 2010. 107(22): p. E92-93, author reply E94-95), SPECT (see Yu, H. Y., J. S. Yang, M. Jiang, and G. Wang, Interior Spect-Exact and Stable Roi Reconstruction from Uniformly Attenuated Local Projections. Communications in Numerical Methods in Engineering, 2009.25(6): p. 693-710), MRI (see Wang, G., J. Zhang, H. Gao, V. Weir, H. Y. Yu, W. X. Cong, X. C. Xu, H. O. Shen, J. Bennett, M. Furth, Y. Wang, and M. W. Vannier, Towards Omni-Tomography. Plos One, 2012), and phase-contrast tomography (see Cong, W. X., J. S. Yang, and G. Wang, Differential Phase-Contrast Interior Tomography. Phys. Med. Biol., 2012). Because of the benefits from interior tomography, various data acquisition moduli can be made more compact and integrated for omni-tomography (see Wang, G., J. Zhang, H. Gao, V. Weir, H. Y. Yu, W. X. Cong, X. C. Xu, H. O. Shen, J. Bennett, M. Furth, Y. Wang, and M. W. Vannier, Towards Omni-Tomography. Plos One, 2012).

Innovative CT Architecture—An innovative CT architecture combined with the interior tomography is provided to overcome major limitations of temporal resolution and radiation dose. The scanning speed of ~3 revolutions per second has now reached the mechanical upper limit of the gantry. The multi-source strategy is the well-known solution to improve the CT data acquisition speed. Nonetheless, the implementation of multiple x-ray sources in the conventional CT architecture is inhibited by the limited gantry space and the bulky imaging chain. See Zhao, J., M. Jiang, T. G. Zhuang, and G. Wang, Minimum Detection Window and Inter-Helix Pi-Line with Triple-Source Helical Cone-Beam Scanning. Journal Of X-Ray Science And Technology, 2006. 14(2): p. 95-107. Interior tomography uses a smaller detector size, and allows more imaging chains in the gantry space for accelerated data acquisition. See Wang, G., H. Yu, and Y. Ye, A Scheme for Multi-Source Interior Tomography. Med Phys, 2009. 36(8):p. 3575-3581. Combined with the CNT x-ray sources, multiple x-ray source arrays can now be installed in a CT architecture (FIG. 2). In the framework of Interior tomography, the detectors of smaller size will be used and more imaging chains can be installed within the gantry space for accelerated data acquisition. Specifically, this new architecture is characteristic of the stationary CNT x-ray sources and the rotatory detectors. The workload of the gantry is drastically reduced due to the light weight of the semiconductor-technology based detectors. Hence, the rotation speed of the gantry can be further increased. The temporal resolution is estimated to be <50 ms, which is >33% faster than that of the dual-source CT. The simulation of this architecture within the framework of interior tomography has demonstrated convincing results (see FIGS. 16A-C and FIG. 17A-C).

Translational Animal Models—It is well accepted that mice, rats, and other small animal (rabbit, guinea pig) models of cardiac and lung diseases are subject to large translational gaps. See Walters, E. M., Y. Agca, V. Ganjam, and T. Evans, Animal Models Got You Puzzled?: Think Pig. Animal Models: Their Value in Predicting Drug Efficacy and Toxicity, 2011. 1245: p. 63-64. Houser, S. R., K. B. Margulies, A. M. Murphy, F. G. Spinale, G. S. Francis, S. D. Prabhu, H. A. Rockman, D. A. Kass, J. D. Molkentin, M. A. Sussman, and W. Koch, Animal Models of Heart Failure: A Scientific Statement from the American Heart Association. Circulation Research, 2012: p. published online May 17. In virtually all of these small animal models, induced diseases are studied, since there is a low incidence of clinically relevant, spontaneous diseases. Furthermore, the size of small animals is prohibitive in terms of evaluating interventional procedures. The inventors have appreciated these problems and developed expertise in medium-sized translational animal models of cardiac and pulmonary diseases and have also performed cardiac intervention studies of myocardial infarction/reperfusion injury in pigs, and are actively developing cardiac transplantation technology. Animals of sufficient size can be used to translate medically-relevant problems from humans to animals and back to humans, speeding-up discovery, research, development, and applications.

Design of the stationary-source CT system and its feasibility analysis. CNT Source—A multi-beam distributed x-ray source based on CNT cathodes was developed. The source consists of 25 individually programmable x-ray beams and was integrated into a stationary digital breast tomosynthesis system. See Yang, G., R. Rajaram, G. Cao, S. Sultana, Z. Liu, D. Lalush, J. Lu, and O. Zhou, Stationary Digital Breast Tomosynthesis System with a Multi-Beam Field Emission X-Ray Source Array, in Medical Imaging 2008: Physics of Medical Imaging, J. Hsieh and E. Samei, Editors. 2008. p. 69131A. With the anodes at a positive continuous high voltage (30 kV), each x-ray beam can be turned on and off by programming the corresponding cathode. This switching capability was realized using the n-type MOSFET. By connecting the drain terminal of the MOSFET to the CNT cathode and the source terminal of the MOSFET to the electrical ground respectively, the CNT cathode and the corresponding x-ray beam can be controlled by a transistor-transistor logic (TTL) signal to the gate terminal of the MOSFET. By putting a variable resistor in series to each CNT cathode and applying a common extraction voltage on the all gate electrodes, the level of electron current from individual CNT cathode can be adjusted. Hence, both the current and duration of each beam can be varied. That is, the radiation dose from each x-ray beam can be programmed in terms of either beam current or exposure time. This capability allows higher imaging performance and dose efficiency. An electronic scanning x-ray beam has been demonstrated from the distributed source array with a corresponding TTL pulse sequence to the gate terminals of the MOSFETs used to control the CNT cathodes. See Yang, G., R. Rajaram, G. Cao, S. Sultana, Z. Liu, D. Lalush, J. Lu, and O. Zhou, Stationary Digital Breast Tomosynthesis System with a Multi-Beam Field Emission X-Ray Source Array, in Medical Imaging 2008: Physics of Medical Imaging, J. Hsieh and E. Samei, Editors. 2008. p. 69131A. The scanning x-ray beam can be used to not only improve thermal dissipation but also reduce motion blurring.

Interior Tomography—Over the past years, the inventors have systematically investigated precise knowledge-based interior tomography (see Ye, Y., H. Yu, Y. Wei, and G. Wang, A General Local Reconstruction Approach Based on a Truncated Hilbert Transform. International Journal of Biomedical Imaging, 2007. 2007: p. Article ID: 63634,63638 pages; Ye, Y., H. Yu, and G. Wang, Exact Interior Reconstruction with Cone-Beam Ct. International Journal of Biomedical Imaging, 2007. 2007: p. Article ID: 10693, 10695 pages; Ye, Y., H. Y. Yu, and G. Wang, Exact Interior Reconstruction from Truncated Limited-Angle Projection Data. International Journal of Biomedical Imaging, 2008. 2008: p. Article ID: 427989, 427986 Pages; Yu, H. Y., J. S. Yang, M. Jiang, and G. Wang, Interior Spect-Exact and Stable Roi Reconstruction from Uniformly Attenuated Local Projections. Communications in Numerical Methods in Engineering, 2009. 25(6): p. 693-710; Yu, H., Y. Ye, and G. Wang, Local Reconstruction Using the Truncated Hilbert Transform Via Singular Value Decomposition. Journal of X-Ray Science and Technology, 2008. 16(4): p. 243-25) and sparsity-based interior tomography (see Yu, H. and G. Wang, Compressed Sensing Based Interior Tomography. Phys Med Biol, 2009. 54(9):2791-2805; Yu, H., J. Yang, M. Jiang, and G. Wang, Supplemental Analysis on Compressed Sensing Based Interior Tomography. Phys Med Biol, 2009. 54(18): p. N425-N432; Yang, J. S., H. Y. Yu, M. Jiang, and G. Wang, High-Order Total Variation Minimization for Interior Tomography. Inverse Problems, 2010. 26(3): p. 29; Katsevich, G., A. Katsevich, and G. Wang, Stability of the Interior Problem with Polynomial Attenuation in a Region of Interest. Inverse Problems, 2012; Han, W., H. Yu, and G. Wang, A Total Variation Minimization Theorem for Compressed Sensing Based Tomography. International Journal of Biomedical Imaging, 2009. 2009: p. Article ID:125871,125873 pages; Yang, J., H. Yu, M. Jiang, and G. Wang, High Order Total Variation Minimization for Interior Spect. Inverse Problems, 2012. 28(1): p. Article ID: 015001, 015024 pages) for x-ray CT.

Figure 13:
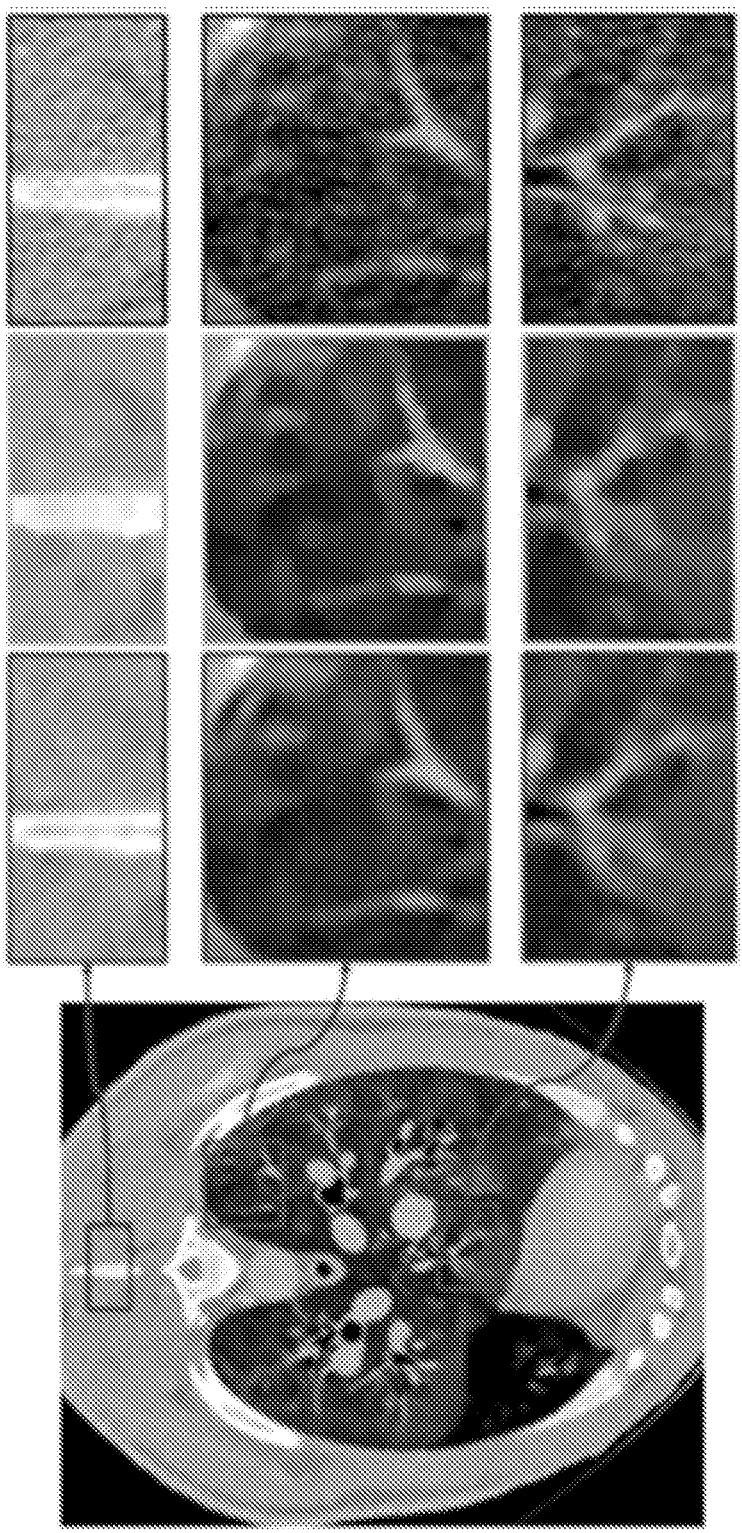
FIG. 13 is an image showing reconstructed images from a few-view low-dose sinogram collected in a sheep lung CT perfusion study (global, instead of interior, reconstruction). The images were reconstructed using the dictionary-learning-based SIR, total-variation-minimization-based SIR, and conventional filtered backprojection respectively. The 1st, 2nd, and 3rd rows are the corresponding magnifications of the three square regions from top to bottom. The dictionary-learning-based SIR and total-variation-minimization-based SIR images were reconstructed from only 290 views, while the filtered backprojection images were from 1160 views.

Practical algorithms have been developed for interior tomography (Ye, Y., H. Yu, Y. Wei, and G. Wang, A General Local Reconstruction Approach Based on a Truncated Hilbert Transform. International Journal of Biomedical Imaging, 2007. 2007: p. Article ID: 63634, 63638 pages; Yu, H. Y., J. S. Yang, M. Jiang, and G. Wang, Interior Spect-Exact and Stable Roi Reconstruction from Uniformly Attenuated Local Projections. Communications in Numerical Methods in Engineering, 2009. 25(6): p. 693-710; Wang, G., H. Yu, and Y. Ye, A Scheme for Multi-Source Interior Tomography. Med Phys, 2009. 36(8):p. 3575-3581; Yu, H., Y. Ye, and G. Wang, Local Reconstruction Using the Truncated Hilbert Transform Via Singular Value Decomposition. Journal of X-Ray Science and Technology, 2008. 16(4): p. 243-251) and compressive sensing (see Yu, H. and G. Wang, Compressed Sensing Based Interior Tomography. Phys Med Biol, 2009. 54(9): p. 2791-2805; Yang, J. S., H. Y. Yu, M. Jiang, and G. Wang, High-Order Total Variation Minimization for Interior Tomography. Inverse Problems, 2010. 26(3): p. 29; Yu, H., G. Cao, L. Burk, Y. Lee, J. Lu, P. Santago, O. Zhou, and G. Wang, Compressive Sampling Based Interior Tomography for Dynamic Carbon Nanotube Micro-Ct. Journal of X-Ray Science and Technology, 2009. 17(4): p. 295-303; Yu, H. and G. Wang, Sart-Type Image Reconstruction from a Limited Number of Projections with the Sparsity Constraint. International Journal of Biomedical Imaging, 2010. 2010: p. Article ID: 934847, 934849 pages; Yu, H. and G. Wang, A Soft-Threshold Filtering Approach for Reconstruction from a Limited Number of Projections. Phys Med Biol, 2010. 55(13): p. 3905-3916; Yu, H., C. Ji, and G. Wang, Sart-Type Image Reconstruction from Multi-Source Overlapped Projections. International Journal of Biomedical Imaging, 2010: p. Article ID:549537) with excellent preclinical and clinical image quality. Very recently, the inventors have incorporated a dictionary-learning-based sparse constraint into a statistical iterative reconstruction (SIR) framework. See Xu, Q., H. Yu, X. Mou, and G. Wang, Low-Dose X-Ray Ct Reconstruction Via Dictionary Learning. IEEE Trans Med Imaging, September 2012, 31(9), 1682-1697 (published online Apr. 20, 2012, doi: 10.1109/TMI.2012.2195669; Xu, Q., H. Yu, X. Mou, and G. Wang, Dictionary Learning Based Low-Dose X-Ray Ct Reconstruction, in Fully 3D 20112011. Preliminary results show that the dictionary-learning-based SIR approach clearly outperforms the total-variation-minimization-based SIR (FIG. 13). This dictionary-learning-based SIR approach can be expanded for few-view interior tomography (FIT) to provide algorithmic support for the exemplary CVCT system.

Design of a STRICT System. A STationary-source Rotatory-detector Interior CT (STRICT) architecture (FIG. 14 and Table 1) can be configured such that stationary linear CNT source arrays (or curved source arrays) are fixed around the patient. Each CNT x-ray source array contains ~33 CNT x-ray beams. Three detectors are mounted on a rotation gantry. To synchronize with rotating detectors, the three CNT arrays are electronically activated to approximate the spinning of three single-beam x-ray sources. For example, each CNT source array may cover an angular region up to ~80°. The temporal resolution is then determined by the scan time across this 80° angular region, and can be easily made ≤50 ms, which is >33% faster than the state of art dual source CT. Another advantage of this scheme is lower radiation dose. Within the framework of interior tomography, the x-ray beam is collimated towards the ROI. For few-view reconstruction, the total number of views is much smaller than that of traditional cardiac CT. For low-dose reconstruction such as MBIR (model-based iterative reconstruction), the photon flux can be only ~10% of the conventional counterpart. See Fleischmann, D. and F. E. Boas, Computed Tomography—Old Ideas and New Technology. Eur Radiol, 2011. 21(3): p. 510-517; Yu, Z., J. B. Thibault, C. A. Bouman, K. D. Sauer, and J. Hsieh, Fast Model-Based X-Ray Ct Reconstruction Using Spatially Nonhomogeneous Icd Optimization. IEEE Trans Image Process, 2011. 20(1): p. 161-175; Thibault, J. B., K. D. Sauer, C. A. Bouman, and J. Hsieh, A Three-Dimensional Statistical Approach to Improved Image Quality for Multislice Helical Ct. Med Phys, 2007. 34(11): p. 4526-4544. By estimation, the effective dose per scan should be sub-mSv.

TABLE 1

Specifications of a STRICT system.

| | |
|---|---|
| X-ray Sources | 3 CNT arrays |
| Beams per Array | ~33 |
| X-ray Detectors | 3 high-speed detectors |
| Detector Pitch | 0.3 mm |
| Integration Time | 0.24 ms |
| System | STRICT |
| Source-to-Isocenter | ~54 cm |
| Source-to-Detector | ~95 cm |
| Angular Coverage | 180°-240° |
| Spatial Resolution | 0.4 mm |
| Temporal resolution | <50 ms |
| CT dose | <1 mSv |

Figure 15A:
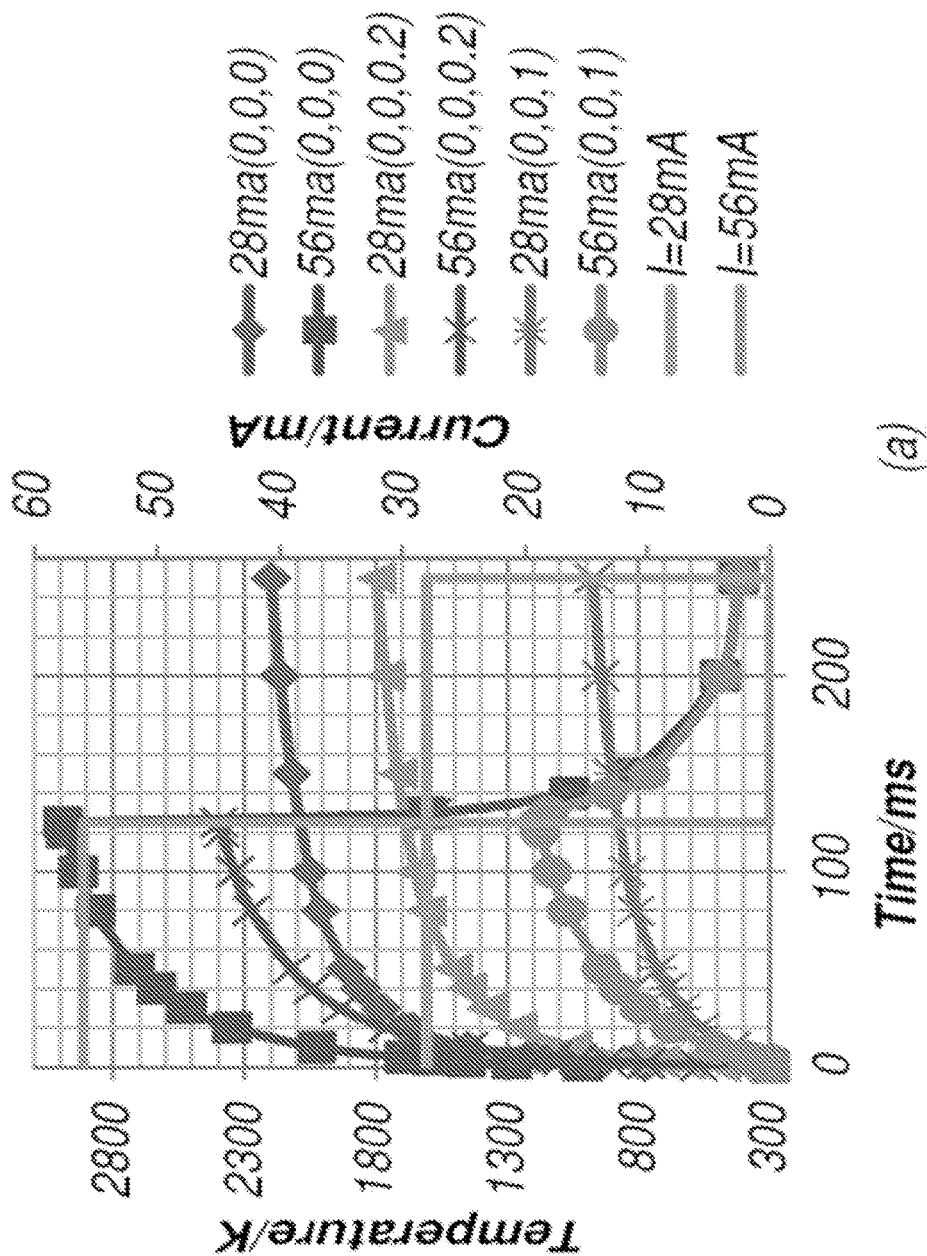
Figure 15B:
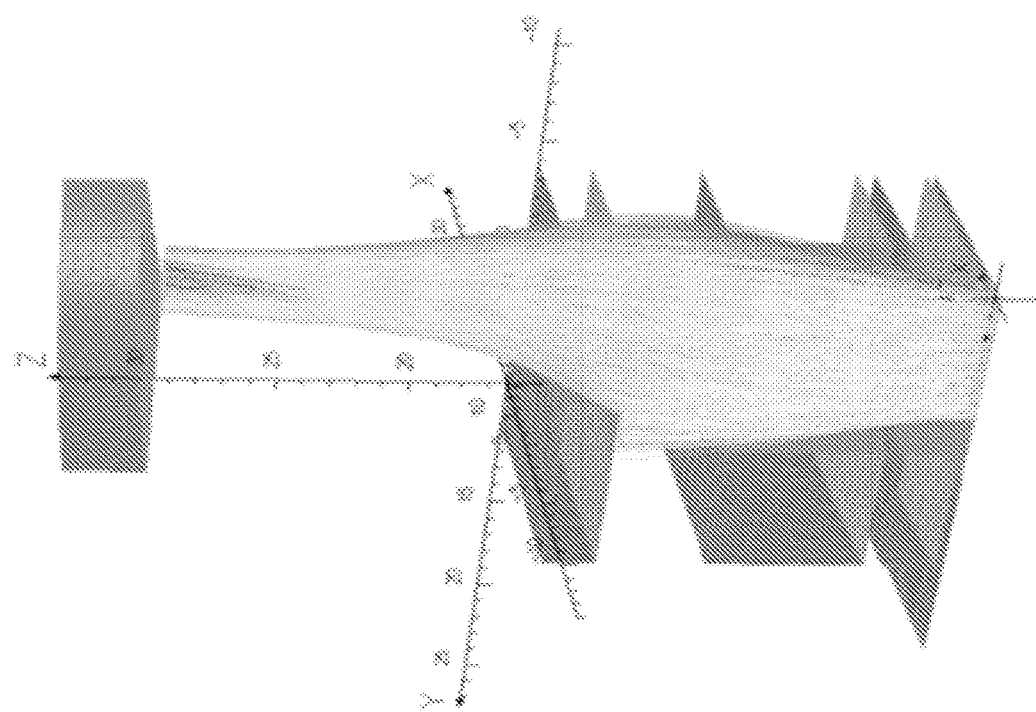

The major works include the following:

CNT Source Array. A multi-beam distributed CNT x-ray source array can be provided, such as incorporating the performance parameters of the CNT x-ray sources shown in Table 2. Each source array can have ~100 x-ray beams, which are arranged linearly or on a curve to cover an angular range of ~80°. The angular array can cover any range between 0-360°, such as using 2-6 arrays each with an angular range of between 60-120°. Three such x-ray source arrays can be used to enable the half-scan (180° plus the fan angle) without source rotation. A key performance parameter is the heat load that can be tolerated by the tungsten anode for a given set of anode voltage, tube current, focal spot size, and pulse duration. The simulation of heat load (FIGS. 15A and 15B) can be conducted using a commercial software package (ANSYS, USA). The electron optics can be designed for the required focal spot size and beam sweeping to avoid operational complications. Previously, an improved Enzel-type lens with active focusing electrodes was developed for a CNT micro-focus source to provide a factor of 5-10 focusing power. See Houser, S. R., K. B. Margulies, A. M. Murphy, F. G. Spinale, G. S. Francis, S. D. Prabhu, H. A. Rockman, D. A. Kass, J. D. Molkentin, M. A. Sussman, and W. Koch, Animal Models of Heart Failure: A Scientific Statement from the American Heart Association. Circulation Research, 2012: p. published online May 17. Two other focusing approaches have also been developed. The first one utilizes a single active-focusing electrode. See Yang, G., R. Rajaram, G. Cao, S. Sultana, Z. Liu, D. Lalush, J. Lu, and O. Zhou, Stationary Digital Breast Tomosynthesis System with a Multi-Beam Field Emission X-Ray Source Array, in Medical Imaging 2008: Physics of Medical Imaging, J. Hsieh and E. Samei, Editors. 2008. p. 69131A. The other one adopts the passive-focusing without active input voltage. See Yu, H., Y. Ye, and G. Wang, Local Reconstruction Using the Truncated Hilbert Transform Via Singular Value Decomposition. Journal of X-Ray Science and Technology, 2008. 16(4): p. 243-251. Computer-aided design (CAD) with a commercial software package (Opera, VectorFields, USA) can for example be conducted in the optimization of the focusing approaches and the design of x-ray source.

Interior Beam Collimation: At any moment, three x-ray beams from the three CNT source arrays can be caused to irradiate an ROI of 20 cm simultaneously. Three interior beam collimators can be mounted on the same gantry opposite the three detectors. The collimator will act to narrow the wide beams from the source arrays to irradiate the 20 cm ROI only. The rotation of the detectors and interior collimators can be synchronous to the sweeping speed of the focal spots within the source arrays. As a result, the detectors, interior collimators, and source points will be always aligned.

System CAD Design: A detailed electro-mechanical model can be built using SolidWorks and other tools in collaboration with Moog and Agile (see Letters of Support from Moog and Agile). The mechanical model can then be examined in SolidWorks Motion for mechanical interference, resonance, vibration, and load balance. Other novel candidates such as systems with stationary arc CNT source arrays, and a hybrid interior CT system that uses large conventional and small detectors simultaneously can be synergistically evaluated (see Tang, J., J. Hsieh, and G. H. Chen, Temporal Resolution Improvement in Cardiac Ct Using Piccs (Tri-Piccs): Performance Studies. Medical Physics, 2010. 37(8): p. 4377-4388) for more options/applications. The STRICT architecture will greatly simplify the design of the slip ring, and in some cases render the slip ring optional, because the x-ray sources and their HV driving units are removed from the gantry, which should simplify the mechanic works of the system.

Optimization of the STRICT Architecture.

Figure 16B:
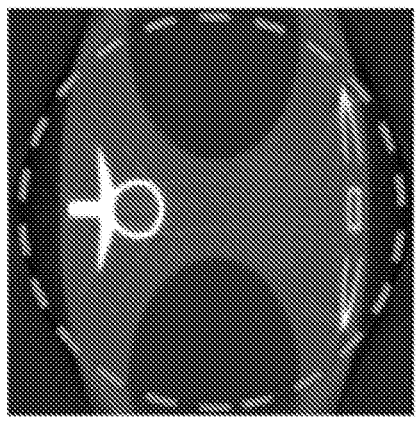
Figure 16C:
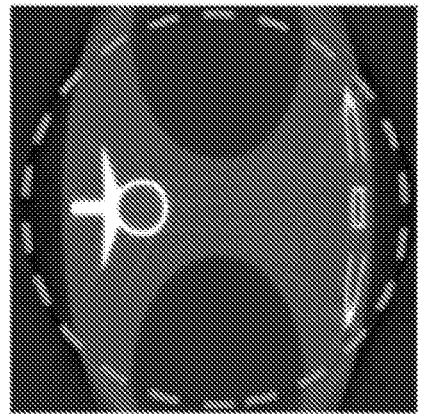
Figure 16A:
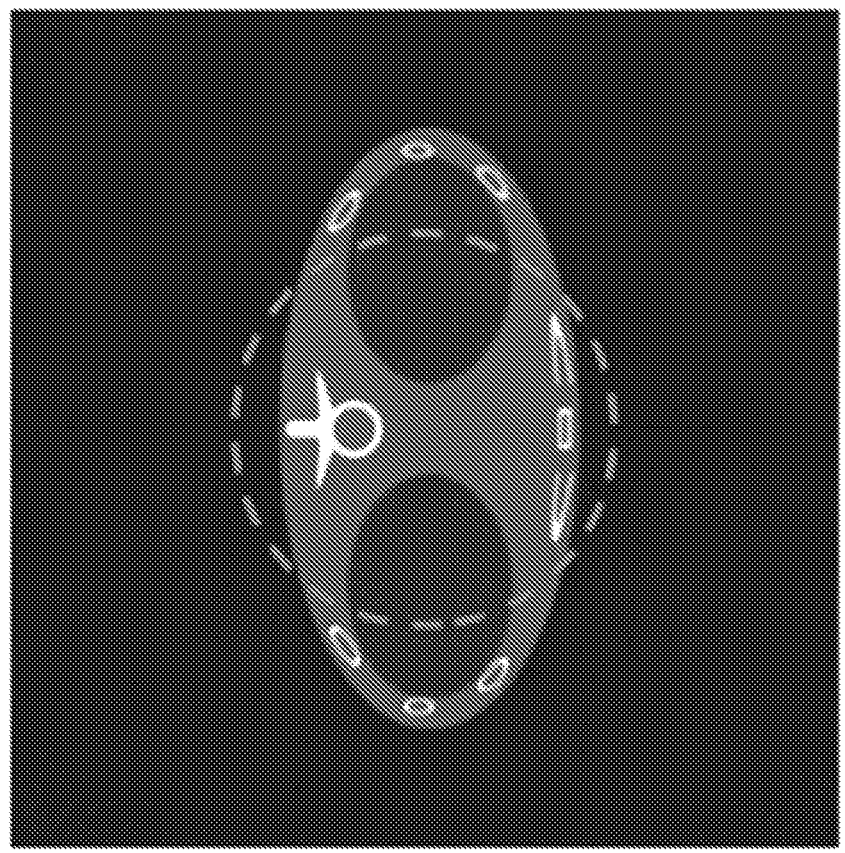
Figure 17B:
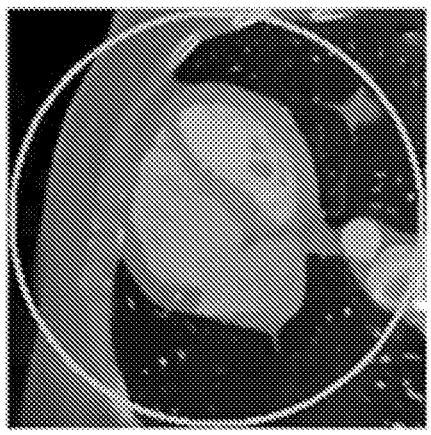
Figure 17C:
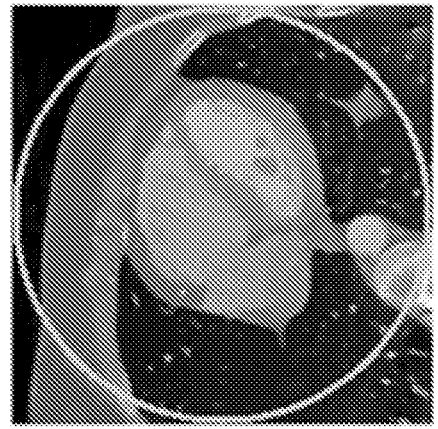
Figure 17A:

Numerical Simulation—The STRICT system performance can be simulated numerically before moving into physical testing. Preliminary simulation of the architecture has been carried out (FIGS. 16A-C). The simulation was conducted using CATSIM (the CT simulation environment from GE healthcare) and the image reconstruction was completed using OpenRecon (an in-house open source image reconstruction package). The simulation was also extended with the clinical cardiac CT data from a commercial CT scanner (GE Discovery CT750 HD) (FIGS. 17A-C). To approximate the stationary x-ray source arrays, the projections within certain angular ranges were extracted and used in reconstruction. In FIG. 17B, the projections in [0, 60°], [120°, 180°] and [240°, 300°] were used to simulate the half scan. In FIG. 20C, the projections in [0, 81.4°], [120°, 201.4°], and [240°, 321.4°] were used to simulate the short scan. As is shown in FIGS. 17A-C, the image quality is still maintained even with the interior ROI and the reduced number of projections. Meanwhile, the impact of the interior tomography on the spatial resolution was also investigated using the customized wire phantom. With 720 projections, the conventional CT architecture and the filtered back projection approaches can only achieve the spatial resolution of 6 lp/mm. In comparison, the STRICT architecture combined with the few-view interior reconstruction method can still maintain higher spatial resolution (see FIG. 18). These simulations demonstrate the potential of the STRICT system for clinical usage.

TABLE 2 the specifications of an examplary CNT x-ray source

| Anode Voltage | 120 kV |
|---|---|
| Focal Spot | Sweeping 0.5 × 5 mm$^2$ |
| Anode Current | ~100 mA |
| Pulse Width | ~200 µs |
| Anode | Tungsten |
| Anode Cooling | Active, e-beam sweeping |
| X-ray Window | 1 mm Al |

Test-bed Development—A CT test bed equipped with a CNT single-beam x-ray source, commercial micro-focus x-ray source, flat panel detector, spectral detector, and linear and rotation stages can be constructed. This test-bed can be used as a reference. It is capable of simulating—not only the conventional CT architecture but also the interior tomography. Currently, it is used to evaluate the prototype single-beam CNT source. The phantom is mounted on the rotatory stage. The x-ray source or source array (including collimation) can be fixed on the linear 2-axis stage. The flat panel x-ray detector is mounted on the second 2-axis linear stages. The linear stages and the rotatory stage are mounted on the optical table. The controlling software of this test bed has been developed using LabVIEW.

Architectural Optimization—A single-beam source prototype can be built and tested using a commercial CT tube, to evaluate and optimize the STRICT architecture. Based on the above-described design, the iterative approach can be employed to optimize the system performance. The optimization of distributed x-ray sources is an emphasis. Increasing the number of views can enhance image quality. With distributed CNT sources and given a total scan time, the more views, the more the source array will raise the cost, and reduce the exposure time for each view. Thus, the optimal tradeoff among the number of x-ray sources, image quality, and the cost needs to be addressed.

Development of Reconstruction Algorithms.

Robust Few-view Interior Tomography (FIT) methods can be developed with a dictionary-based sparsity constraint. The FIT methods can evolve from the state-of-the-art algorithms such as prior image constrained compressed sensing (PICCS) and cardiac motion compensation. The FIT algorithms can also be accelerated via high-performance computing to enable real-time image reconstruction.

Figure 18:
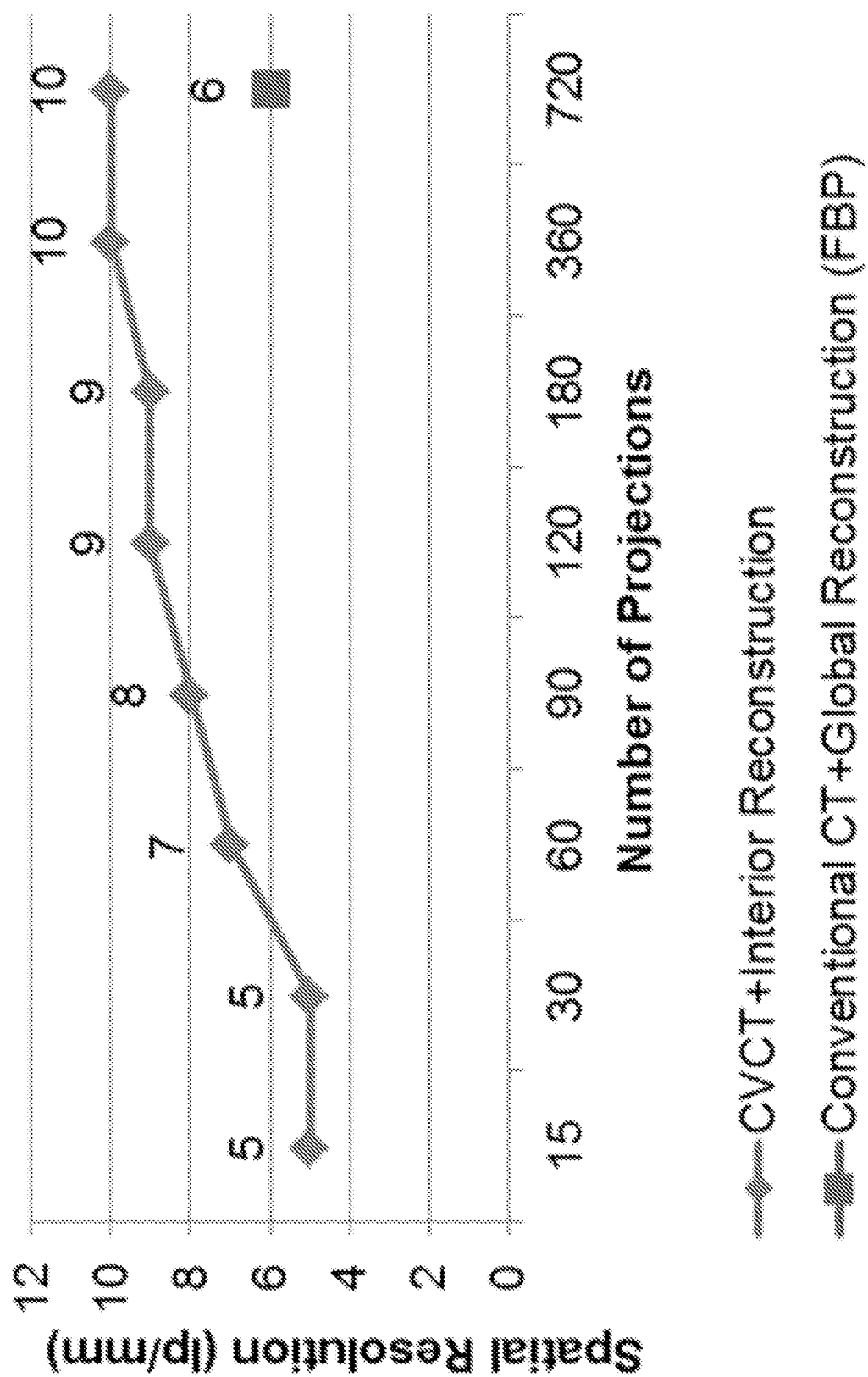
FIG. 18 is a graph showing spatial resolution measurement of STRICT architecture using experimental data collected in the PI's lab. Details: 20 μm wire phantom, commercial x-ray source, flat-panel detector; the number of beams in each source array was increased from 5 to 240. The conventional CT architecture and FBP can only achieve spatial resolution up to 6 lp/mm (square).

FIG. 18 is a graph showing spatial resolution measurement of STRICT architecture using experimental data. Details: 20 µm wire phantom, commercial x-ray source, flat-panel detector; the number of beams in each source array was increased from 5 to 240. The conventional CT architecture and FBP can only achieve spatial resolution up to 6 lp/mm (square).

Dictionary-based Sparse Representation—A dictionary is a matrix, $D \in \mathbb{R}^{N \times K}$ (N<K), and each column $\{d_k\}_{k=1}^{K}$ is called an atom. If an image patch $X_0 \in \mathbb{R}^{N \times 1}$ of $\sqrt{N} \times \sqrt{N}$ pixels can be approximated as a sparse linear combination of the atoms, the sparse representation (SR) $\alpha_0 \in \mathbb{R}^{K \times 1}$ must solve the following problem $$\min_{\alpha_0} \|X_0 - D\alpha_0\|_2^2 + v_0 \|\alpha_0\|_0, \quad \text{(C.2-1)}$$

where $\|\cdot\|_0$ is the $l_0$-norm, $\|\alpha_0\|_0 \ll N$, and $v_0$ is a weighting factor. The goal of dictionary learning (DL) is to seek a dictionary for each patch in a given training set to be sparsely represented by the atoms of this dictionary. For the given patch set $\{X_s\}_{s=1}^{S}$ and the corresponding SR vector $\alpha = \{\alpha_s\}_{s=1}^{S}$, we have $$\min_{D,\alpha} \Sigma_{s=1}^{S} (\|X_s - D\alpha_s\|_2^2 + v_s \|\alpha_s\|_0). \quad \text{(C.2-2)}$$

High-order Total Variation—In the continuous domain, it has been proven that an accurate solution to the interior problem is achievable via minimizing the TV or high order TV (HOT) of an reconstructed image F subject to the data fidelity constraint, assuming that the ROI is a piecewise constant or polynomial (See Ye, Y., H. Yu, Y. Wei, and G. Wang, A General Local Reconstruction Approach Based on a Truncated Hilbert Transform. International Journal of Biomedical Imaging, 2007. 2007: p. Article ID: 63634, 63638 pages.; Yu, H. and G. Wang, Compressed Sensing Based Interior Tomography. Phys Med Biol, 2009. 54(9):p. 2791-2805; Yu, H., J. Yang, M. Jiang, and G. Wang, Supplemental Analysis on Compressed Sensing Based Interior Tomography. Phys Med Biol, 2009. 54(18): p. N425-N432; Cao, G., L. M. Burk, Y. Z. Lee, X. Calderon-Colon, S. Sultana, J. Lu, and O. Zhou, Prospective-Gated Cardiac Micro-Ct Imaging of Free-Breathing Mice Using Carbon Nanotube Field Emission X-Ray. Medical Physics, 2010. 37(10): p. 5306-5312).

Statistical Reconstruction—Measured data from a monochromatic x-ray source can be modeled as a Poisson distribution, $y_i \sim \text{Poisson}\{\bar{y}_i\}$, $i=1, \ldots, I$, where $\bar{y}_i = b_i e^{-p_i}$ is the expected value of the measurement $y_i$, $b_i$ the blank scan factor, $p_i$ the linear integral of attenuation coefficients along the x-ray path, $p_i = \Sum_{j=1}^{J} g_{ij} f_j = [GF]_i$, where $G=\{g_{ij}\}$ is the system matrix, $F=(f_1, \ldots, f_J)^T$ the linear attenuation coefficient vector, I and J are the indices of projections and pixels respectively. The statistical reconstruction is equivalent to maximize the following objective function $$\Phi(F) = \Sum_{i=1}^{I}(y_i[GF]_i + b_i e^{-[GF]_i}) + R(F), \quad (C.2\text{-}3)$$

where R(F) is a regularization term expressing the a priori knowledge.

Alternating Minimization Scheme—With Eq. (C.2-2) for R(F) in Eq. (C.2-3) and by the 2nd order Taylor expansion of $y_i p_i + b_i e^{-p_i}$ at $\hat{p}_i = \ln(b_i/y_i)$, the objective functional in preliminary studies for global reconstruction were obtained (See Lauzier, P. T., J. Tang, and G. H. Chen, Time-Resolved Cardiac Interventional Cone-Beam Ct Reconstruction from Fully Truncated Projections Using the Prior Image Constrained Compressed Sensing (Piccs) Algorithm. Physics in Medicine and Biology, 2012. 57(9); Chen, G. H., P. Theriault-Lauzier, J. Tang, B. Nett, S. Leng, J. Zambelli, Z. H. Qi, N. Bevins, A. Raval, S. Reeder, and H. Rowley, Time-Resolved Interventional Cardiac C-Arm Cone-Beam Ct: An Application of the Piccs Algorithm. Ieee Transactions on Medical Imaging, 2012. 31(4): p. 907-923). In this project, we will combine the merits of DL and HOT to form a more general objective function for FIT reconstruction, and solve it using the alternating minimization algorithm (AMA). See Chen, G. H., J. Tang, B. Nett, Z. H. Qi, S. A. Leng, and T. Szczykutowicz, Prior Image Constrained Compressed Sensing (Piccs) and Applications in X-Ray Computed Tomography. Current Medical Imaging Reviews, 2010. 6(2): p. 119-134; Chen, G. H., J. Tang, and S. H. Leng, Prior Image Constrained Compressed Sensing (Piccs): A Method to Accurately Reconstruct Dynamic Ct Images from Highly Undersampled Projection Data Sets. Medical Physics, 2008. 35(2): p. 660-663. In the AMA framework, the split-Bregman approach and soft-threshold filtering technique (see Kobayashi, Y., O. Tanaka, N. Imai, E. Itou, M. Hiraoka, and K. Taguchi, Efficacy of Ecg-Gated Scanning and Ecg-Gated Reconstruction in Multislice Helical Ct with Half-Second Scanning for Improving Image Quality of the Heart and Lung Parenchyma: Evaluation Using a Cardiac Motion Phantom. Radiology, 2000. 217: p. 162-162) will update the reconstructed image F given a and D. Then, keeping the intermediate image unchanged, a and D will be estimated using the fast online algorithm (see Hiraoka, M., K. Taguchi, and H. Anno, Improvement of the Cardiac Volumetric Imaging Using the Modified High Temporal Reconstruction Algorithm with Multislice Helical Ct. Radiology, 1999. 213P: p. 401-402; Taguchi K, Segars W P, Fung G S K, and T. B M W, Toward Time Resolved 4d Cardiac Ct Imaging with Patient Dose Reduction: Estimating the Global Heart Motion, in SPIE Medical Imaging 2006: San Diego, Calif.) to train a dictionary from available patches.

The dictionary can be fixed to update the sparse representation using the orthogonal matching pursuit (OMP) algorithm. See Segars, W. P., M. Mahesh, T. J. Beck, E. C. Frey, and B. M. W. Tsui, Realistic Ct Simulation Using the 4d Xcat Phantom. Medical Physics, 2008. 35(8): p. 3800-3808. Frey, E. C., K. L. Gilland, and B. M. W. Tsui, Application of Task-Based Measures of Image Quality to Optimization and Evaluation of Three-Dimensional Reconstruction-Based Compensation Methods in Myocardial Perfusion Spect. IEEE TRANSACTIONS ON MEDICAL IMAGING, 2002. 21(9): p. 1040-1050. The ordered-subset (OS) approach (see Sankaran, S., E. C. Frey, K. L. Gilland, and B. M. W. Tsui, Optimum Compensation Method and Filter Cutoff Frequency in Myocardial Spect: A Human Observer Study. Journal Of Nuclear Medicine, 2002.43(3): p. 432-438; Bian, J., J. H. Siewerdsen, X. Han, E. Y. Sidky, J. L. Prince, C. A. Pelizzari, and X. Pan, Evaluation of Sparse-View Reconstruction from Flat-Panel-Detector Cone-Beam Ct. Phys Med Biol, 2010. 55(22): p. 6575-6599. Gifford, H. C., M. A. King, D. J. de Vries, and E. J. Soares, Channelized Hotelling and Human Observer Correlation for Lesion Detection in Hepatic Spect Imaging. Journal Of Nuclear Medicine, 2000. 41(3): p. 514-521) can be used to minimize the data fidelity term. The fast iterative soft-thresholding algorithm (FISTA) (see Gilland, K. L., B. M. W. Tsui, Y. J. Qi, and G. T. Gullberg, Comparison of Channelized Hotelling and Human Observers in Determining Optimum Os-Em Reconstruction Parameters for Myocardial Spect. IEEE Transactions On Nuclear Science, 2006. 53(3): p. 1200-1204) can accelerate the convergence of the reconstruction process. Based on the convergence results (see Gilland, K. L., B. M. W. Tsui, Y. J. Qi, and G. T. Gullberg, Comparison of Channelized Hotelling and Human Observers in Determining Optimum Os-Em Reconstruction Parameters for Myocardial Spect. IEEE Transactions On Nuclear Science, 2006. 53(3): p. 1200-1204; Oldan, J., S. Kulkarni, Y. X. Xing, P. Khurd, and G. Gindi, Channelized Hotelling and Human Observer Study of Optimal Smoothing in Spect Map Reconstruction. IEEE Transactions On Nuclear Science, 2004. 51(3): p. 733-741. Fryback, D. G. and J. R. Thornbury, The Efficacy of Diagnostic-Imaging. Medical Decision Making, 1991. 11(2): p. 88-94. Krupinski, E. A. and Y. L. Jiang, Anniversary Paper: Evaluation of Medical Imaging Systems. Medical Physics, 2008. 35(2): p. 645-659), the local and global convergence of the FIT approach with either global or adaptive dictionaries can be studied. See Lauzier, P. T., J. Tang, and G. H. Chen, Time-Resolved Cardiac Interventional Cone-Beam Ct Reconstruction from Fully Truncated Projections Using the Prior Image Constrained Compressed Sensing (Piccs) Algorithm. Physics in Medicine and Biology, 2012. 57(9).

Interestingly, interior tomography takes less data but more time than conventional tomography. Hence, high-performance computing techniques can be used to accelerate the interior CVCT reconstruction process. Preferably, a target reconstruction speed for a CVCT study on a single animal scan is in real-time with useable resolution or under 5 minutes for optimized quality.

Development and characterization of a CNT source with sweeping electron beam, such as an Open-chamber Single-beam CNT Source.

A single-beam source can be configured with the specifications listed in Table 2. The x-ray source can have an open-chamber design with a flange that can be opened and re-sealed. This approach allows rapid modification of the x-ray source structure to accommodate any potential flaws unnoticed in the designing phase, and quick validation of any modified design as well.

Feasibility Analysis—The key points are as follows. (i) CNT cathode current: the targeted tube current is 100 mA at 0.5×5 mm2 effective focal spot size. After taking into account the anode takeoff angle, after taking into account the anode projection angle, the focusing power of the electrostatic lens, and the transmission rate, the required cathode current density is well within the previously demonstrated high-current density (0.4-1.4 A/cm2) and long-term stability. See Calderon-Colon, X., H. Geng, B. Gao, L. An, G. Cao, and O. Zhou, A Carbon Nanotube Field Emission Cathode with High Current Density and Long-Term Stability. Nanotechnology, 2009. 20(32): p. 325707 (325705pp). (ii) Stability under high anode voltage and high power operation: the CNT x-ray source was demonstrated to run stably at 160 kV anode voltage. See Zhou, O. and X. Calderon-Colon, Carbon Nanotube-Based Field Emission X-Ray Technology, in Carbon Nanotube and Related Field Emitters: Fundamentals and Applications, Y. Saito, Editor 2010, WILEY-VCH Verlag GmbH & Co. Thus, operating the CNT sources at a voltage of 120 kV does not present any issues. Additional heat load simulation may be useful in determining the maximum pulse length at the required power and focal spot size for a particular application.

Based on previous anode thermal analyses (see Grider, D. E., A. Wright, and P. K. Ausburn, Electron Beam Melting in Microfocus X-Ray Tubes. J. Phys. D, 1986. 19: p. 2281-2292; Flynn, M., S. Hames, D. Reimann, and S. Wilderman, Microfocus X-Ray Sources for 3d Microtomography. Nucl. Instrum. Methods Phys. Res. A, 1994. 353(1—3): p. 312-315), the targeted anode current is well within the anode thermal limit. (iii) X-ray anode heat load: With a fixed anode, the CNT source can tolerate >100 W tube power (50 kV and 2 mA) at 100 μm focal spot and 12° anode takeoff angle. See Cao, G., L. M. Burk, Y. Z. Lee, X. Calderon-Colon, S. Sultana, J. Lu, and O. Zhou, Prospective-Gated Cardiac Micro-Ct Imaging of Free-Breathing Mice Using Carbon Nanotube Field Emission X-Ray. Medical Physics, 2010. 37(10): p. 5306-5312; Cao, G., Y. Lee, R. Peng, Z. Liu, R. Rajaram, X. Calderon-Colon, L. An, P. Wang, T. Phan, S. Sultana, D. Lalush, J. Lu, and O. Zhou, A Dynamic Micro-Ct Scanner Based on a Carbon Nanotube Field Emission X-Ray Source. Physics in Medicine and Biology, 2009. 54(8): p. 2323-2340; Cao, G., X. Calderon-Colon, P. Wang, L. Burk, Y. Z. Lee, R. Rajaram, S. Sultana, D. Lalush, J. Lu, and O. Zhou. A Dynamic Micro-Ct Scanner with a Stationary Mouse Bed Using a Compact Carbon Nanotube Field Emission X-Ray Tube. 2009. 7258(1). SPIE. For animal studies, the focal spot size of CNT sources can be relaxed to ~500 μm. The anode voltage can be increased from 50 kV to 120 kV, given the involved larger chest diameter of ~50 cm. See Reid, J., J. Gamberoni, F. Dong, and W. Davros, Optimization of Kvp and Mas for Pediatric Low-Dose Simulated Abdominal Ct: Is It Best to Base Parameter Selection on Object Circumference? American Journal of Roentgenology. 195(4): p. 1015-1020. Assuming that the heat load of a fixed anode is proportional to its focal spot area, the tube power and current in the inventive systems can reach 2.5 kW and 31 mA according to an experimental anode thermal study. See Grider, D. E., A. Wright, and P. K. Ausburn, Electron Beam Melting in Microfocus X-Ray Tubes. J. Phys. D, 1986. 19: p. 2281-2292. To compensate the detector motion, the focal spot can be electromagnetically steered across a 5 mm focal track during the ~200 μs detector integration time, so that the focal spot is relatively fixed to the detector and interior collimator during data acquisition. By sweeping the electron beam across a ~5 mm focal track, the maximum tube load can be readily increased by a factor of ~10× (5 mm/0.5 mm=10) to reach 12 kW and ~100 mA, comparable to specifications of modern CT tubes. See Schardt, P., J. Deuringer, J. Freudenberger, E. Hell, W. Knupfer, D. Mattern, and M. Schild, New X-Ray Tube Performance in Computed Tomography by Introducing the Rotating Envelope Tube Technology. Med Phys, 2004. 31(9): p. 2699-2706.

Characterization of a Single-Beam CNT Source

Focal spot size. The x-ray source focal spot size can be measured following the industry standard. The electrical potentials applied to the focusing electrodes can be adjusted to optimize the electron focusing effect.

High-voltage stability. The x-ray tube current and the x-ray radiation can be measured as a function of time at different anode voltages. The insulation strength for the anode high voltage can be tested.

X-ray energy spectrum. The energy spectrum of the x-ray photons can be recorded by an x-ray spectrum analyzer (XR-100T-CdTe, Amptek, U.S.A.). The energy distribution of the x-ray photons can be compared with those from the commercial x-ray tubes.

Pulsed x-ray capability. To generate pulsed x-ray radiation with programmable pulse width and repetition rate, the gate voltage can be controlled by a programmable low-voltage source. The anode voltage can be kept at constant. The x-ray pulse thus generated can be recorded by the Amptek x-ray detector (with heavy metal filter in front of its window) and an oscilloscope.

Lifetime. The long-term stability of the source can be evaluated by continuously running the source in an x-ray shielding facility. The performance of the source can be automatically recorded at a fixed time interval using a data acquisition system developed under LabVIEW.

Performance Evaluation of the CNT Source in the STRICT Architecture.

The commercial CT tube in the test-bed platform can be replaced with this characterized single-beam CNT source, and experimental CT scans can be performed on CT phantoms to assess the performance of the single-beam CNT source, before moving to the eventual multi-beam STRICT system. In embodiments, the source and detector can be fixed, and the phantoms rotated.

Simulator—Early numerical simulation can be used to evaluate algorithmic aspects. Realistic numerical and experimental data can be generated to analyze practical aspects such as scattering from the other imaging chains, physiological and pathological defects. The simulator can consist of three parts: Projection (with Monte Carlo modeling routines), Reconstruction, and Analysis. The reconstruction part includes the interior reconstruction algorithms as well as the state-of-the-art algorithms such as prior image constrained compressed sensing (PICCS) (see Lauzier, P. T., J. Tang, and G. H. Chen, Time-Resolved Cardiac Interventional Cone-Beam Ct Reconstruction from Fully Truncated Projections Using the Prior Image Constrained Compressed Sensing (Piccs) Algorithm. Physics in Medicine and Biology, 2012. 57(9); Chen, G. H., P. Theriault-Lauzier, J. Tang, B. Nett, S. Leng, J. Zambelli, Z. H. Qi, N. Bevins, A. Raval, S. Reeder, and H. Rowley, Time-Resolved Interventional Cardiac C-Arm Cone-Beam Ct: An Application of the Piccs Algorithm. Ieee Transactions on Medical Imaging, 2012. 31(4): p. 907-923; Tang, J., J. Hsieh, and G. H. Chen, Temporal Resolution Improvement in Cardiac Ct Using Piccs (Tri-Piccs): Performance Studies. Medical Physics, 2010. 37(8): p. 4377-4388; Chen, G. H., J. Tang, B. Nett, Z. H. Qi, S. A. Leng, and T. Szczykutowicz, Prior Image Constrained Compressed Sensing (Piccs) and Applications in X-Ray Computed Tomography. Current Medical Imaging Reviews, 2010. 6(2): p. 119-134; Chen, G. H., J. Tang, and S. H. Leng, Prior Image Constrained Compressed Sensing (Piccs): A Method to Accurately Reconstruct Dynamic Ct Images from Highly Undersampled Projection Data Sets. Medical Physics, 2008. 35(2): p. 660-663. and cardiac motion compensation. See Kobayashi, Y., O. Tanaka, N. Imai, E. Itou, M. Hiraoka, and K. Taguchi, Efficacy of Ecg-Gated Scanning and Ecg-Gated Reconstruction in Multislice Helical Ct with Half-Second Scanning for Improving Image Quality of the Heart and Lung Parenchyma: Evaluation Using a Cardiac Motion Phantom. Radiology, 2000. 217: p. 162-162; Hiraoka, M., K. Taguchi, and H. Anno, Improvement of the Cardiac Volumetric Imaging Using the Modified High Temporal Reconstruction Algorithm with Multislice Helical Ct. Radiology, 1999. 213P: p. 401-402; Taguchi K, Segars W P, Fung G S K, and T. B M W, Toward Time Resolved 4d Cardiac Ct Imaging with Patient Dose Reduction: Estimating the Global Heart Motion, in SPIE Medical Imaging 2006: San Diego, Calif.

Datasets—The XCAT phantom can be used. See Segars, W. P., M. Mahesh, T. J. Beck, E. C. Frey, and B. M. W. Tsui, Realistic Ct Simulation Using the 4d Xcat Phantom. Medical Physics, 2008. 35(8): p. 3800-3808. This phantom has realistic features to provide anatomical backgrounds. In addition, phantom experiments and post-mortem measurements can be carried out.

Indices—Image quality can be measured in terms of classic indices that are either individual or composite such as resolution, noise, similarity (universal quality index (UQI) and mutual information (MI)), signal-/contrast-to-noise ratio, segmentation errors, dynamic physiological and pathological features. See Frey, E. C., K. L. Gilland, and B. M. W. Tsui, Application of Task-Based Measures of Image Quality to Optimization and Evaluation of Three-Dimensional Reconstruction-Based Compensation Methods in Myocardial Perfusion Spect. IEEE TRANSACTIONS ON MEDICAL IMAGING, 2002. 21(9): p. 1040-1050; Sankaran, S., E. C. Frey, K. L. Gilland, and B. M. W. Tsui, Optimum Compensation Method and Filter Cutoff Frequency in Myocardial Spect: A Human Observer Study. Journal Of Nuclear Medicine, 2002. 43(3): p. 432-438; Bian, J., J. H. Siewerdsen, X. Han, E. Y. Sidky, J. L. Prince, C. A. Pelizzari, and X. Pan, Evaluation of Sparse-View Reconstruction from Flat-Panel-Detector Cone-Beam Ct. Phys Med Biol, 2010. 55(22): p. 6575-6599. Spatial, contrast, temporal and spectral resolution can be evaluated and how these measurement hold up over a range of protocols. Also, limited human observer studies can also be used. See Gifford, H. C., M. A. King, D. J. de Vries, and E. J. Soares, Channelized Hotelling and Human Observer Correlation for Lesion Detection in Hepatic Spect Imaging. Journal Of Nuclear Medicine, 2000. 41(3):p. 514-521; Gilland, K. L., B. M. W. Tsui, Y. J. Qi, and G. T. Gullberg, Comparison of Channelized Hotelling and Human Observers in Determining Optimum Os-Em Reconstruction Parameters for Myocardial Spect. IEEE Transactions On Nuclear Science, 2006. 53(3): p. 1200-1204; Oldan, J., S. Kulkarni, Y. X. Xing, P. Khurd, and G. Gindi, Channelized Hotelling and Human Observer Study of Optimal Smoothing in Spect Map Reconstruction. IEEE Transactions On Nuclear Science, 2004. 51(3): p. 733-741. Finally, we will assess the statistical significance of the results. See Fryback, D. G. and J. R. Thornbury, The Efficacy of Diagnostic-Imaging. Medical Decision Making, 1991. 11(2): p. 88-94; Krupinski, E. A. and Y. L. Jiang, Anniversary Paper: Evaluation of Medical Imaging Systems. Medical Physics, 2008. 35(2): p. 645-659. The endpoint can be a list of what parameters are affected (with p<0.05) by interior tomography compared to the truth mathematically available or independently established, testing the null hypothesis (no difference).

Alternative Strategy—It is hypothesized that the inventors' proposed DL-based or DL-PRISM-based approach would be comparable or even superior (no scattering from non-local beams) in an ROI, relative to the global reconstruction. If data suggest that the DL approach does not cover all the constraints used by other algorithms, the relevant elements from other algorithms can be incorporated into the framework. Such elements can be possibly the prior image penalty term for PICCS (see Chen, G. H., P. Theriault-Lauzier, J. Tang, B. Nett, S. Leng, J. Zambelli, Z. H. Qi, N. Bevins, A. Raval, S. Reeder, and H. Rowley, Time-Resolved Interventional Cardiac C-Arm Cone-Beam Ct: An Application of the Piccs Algorithm. Ieee Transactions on Medical Imaging, 2012. 31(4): p. 907-923) or the cardiac motion estimator. See Taguchi K, Segars W P, Fung G S K, and T. B M W, Toward Time Resolved 4d Cardiac Ct Imaging with Patient Dose Reduction: Estimating the Global Heart Motion, in SPIE Medical Imaging 2006: San Diego, Calif.

Development and evaluation of a CNT source array in the STRICT architecture. Scaling up from Single-beam Source to Multi-beam Source Array can provide for a multi-beam source in a cost-effective linear geometry. The source array can be in an open vacuum chamber for easy modification. This test bed can help evaluate the following aspects.

Scanning Beam—The controlling electronics to scan the x-ray beams can be built and tested using a flat-panel digital x-ray detector (Hamamatsu CMOS x-ray detector). The balance between switching speed, duty load, and stability can be experimentally determined.

Beam-to-beam Non-uniformity—The effect of beam quality variability on the imaging performance can be simulated. The variation can be defined from actual measurement. The measured variation range can be doubled for a conservative margin. The primary parameters include (i) Focal spot size: Different focal spot sizes of the x-ray beams can be modeled to analyze their effect on spatial resolution in projection and image domains; (ii) Photon flux: Output flux variation across the beams can be simulated in various settings: perturbation of a single beam from the rest, half of the beams, and other portions; and (iii) Non-repeatability: The flux of a CNT beam may change in a consistent or random manner, but this effect can be compensated for.

STRICT System Integration and Phantom Characterization.

System Integration—The CNT source array can be integrated with other major components including rotation gantry, high-speed detector, interior collimator, slip ring, and the electronic driving and controlling units. The gantry contains a fixed ring of diameter 96 cm. The CNT source array has a length of ~80 cm, consisting of ~33 CNT x-ray beam assemblies. Source array can have an exit window of 1 mm Al as filter. The detector array can be mounted on the rotational gantry that can be spun at least 3 turns per second.

For the slip ring (see Letter of Support from Moog), the two key parameters are internal diameter of 76 cm and maximum data rate of 300 MB/s. A frequency-dependent quantum accounting diagram (QAD) and a detective quantum efficiency (DQE) model (see Cunningham, I. A., M. S. Westmore, and A. Fenster, A Spatial-Frequency Dependent Quantum Accounting Diagram and Detective Quantum Efficiency Model of Signal and Noise Propagation in Cascaded Imaging Systems. Medical Physics, 1994. 21(3): p. 417-427) can be used to avoid a secondary quantum sink. A model-based approach can be applied for scattering compensation See Cong, W. and G. Wang, X-Ray Scattering Tomography for Biological Applications. Journal of X-Ray Science and Technology, 2011. 19(2): p. 219-227. Cong, W., H. Shen, and G. Wang, Spectrally Resolving and Scattering-Compensated X-Ray Luminescence/Fluorescence Computed Tomography. J Biomed Opt, 2011. 16(6): p. 066014. System software with a user-friendly interface can be developed in C++/QT to control x-ray source on/off, slip ring rotation, detector translation, animal bed, data acquisition, and so on.

Feasibility Analysis—Previously, it has been shown that with a source-to-isocenter distance (SID) of 15 cm a CNT micro-focus x-ray source at 50 kVp and 2 mA provides a sufficient fluence for cardiac micro-CT of a live mouse with ~50 HU image noise and 15 ms exposure time and 76 µm sampling step at the isocenter. (See Cao, G., L. M. Burk, Y. Z. Lee, X. Calderon-Colon, S. Sultana, J. Lu, and O. Zhou, Prospective-Gated Cardiac Micro-Ct Imaging of Free-Breathing Mice Using Carbon Nanotube Field Emission X-Ray. Medical Physics, 2010. 37(10): p. 5306-5312). With the exemplary source parameters (120 kVp and 100 mA) and system geometry (~50 cm SID), the fluence at the isocenter with 0.2 ms exposure time will be a quarter of that of the micro-CT counterpart (100 mA*0.2 ms*120 kV2/50 cm2)/(2 mA*15 ms*50 kV2/15 cm2) 0.4). Now, the sampling step at the isocenter is downgraded from 76 µm for mice to 200 µm for medium-sized animals, the number of photons intercepted by a voxel at the isocenter in the imaging geometry becomes ~2× larger than that in the cardiac micro-CT study. Therefore, it can be expected that the projection data will have ~40% higher the signal-to-noise ratio (SNR). Coupled with the advanced low-dose few-view interior tomography approach, this configuration should be able to deliver <50 ms temporal resolution, 400 µm resolution, and <10 HU noise at sub-mSv radiation dose.

System Characterization—An iterative process is required in numerical simulation, phantom experiments for optimization of the prototype.

Phantom Experiments: Physical phantoms can be used to validate the STRICT system performance. A number of common CT performance phantoms including the two-bead phantom, water phantom, the wire phantom, and the contrast phantom can be used. The two-bead phantom is used for system calibration. The contrast phantom with 5 slots can be filled with different liquids or contrast agents to measure the contrast resolution. For human-sized animal imaging, necessary re-engineering can be performed. In addition, the commercial dynamic cardiac phantom and human torso phantom can be used to evaluate the system performance in cardiac imaging. Image quality can be assessed based on the clinical criteria. Contrast resolution, dose index (CTDI) and other indices can be determined using such phantoms.

Figure 19A:
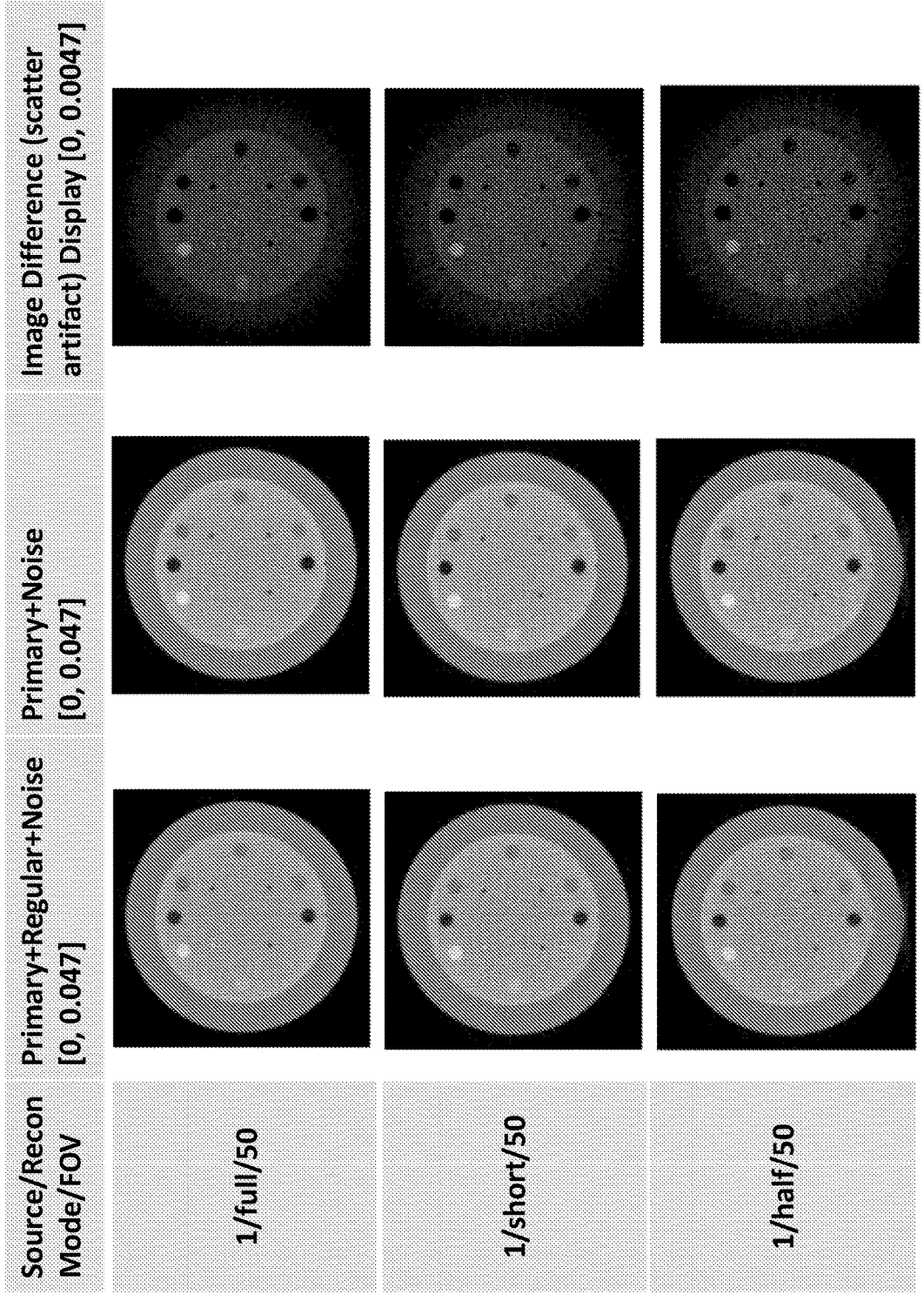
Figure 19B:
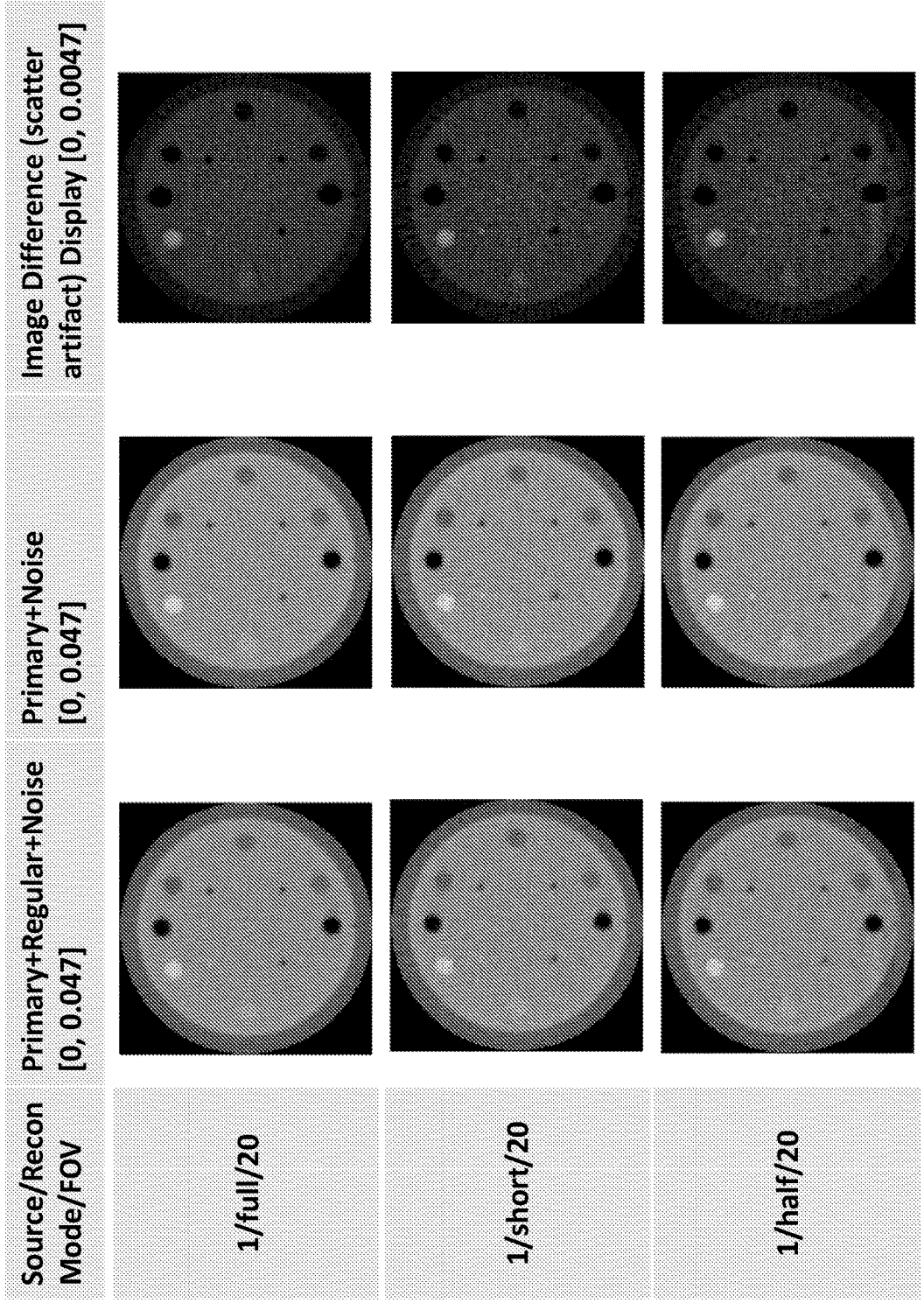
Figure 19D:
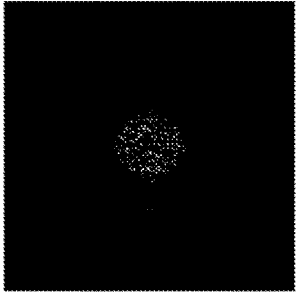

FIGS. 19A-G are images showing image artifacts induced by scatter (FIGS. 19A-D) and image artifacts induced by interior tomography (FIGS. 19E-G) of simulations of conventional scans and reduced FOV scans of the invention. More specifically, the image artifacts induced by scatter show (FIG. 19A) a FOV of 50 cm with 1 source, (FIG. 19B) a FOV of 20 cm with 1 source (no prior information), (FIG. 19C) a FOV of 20 cm with 3 sources (with prior information) including regular scatter and cross scatter, and (FIG. 19D) a FOV of 20 cm with 3 sources (with prior information) including cross scatter only. As can be seen in the figures, the cross scattering does induce worse artifacts and reduce the image quality (FIG. 19D).

Figure 19E:
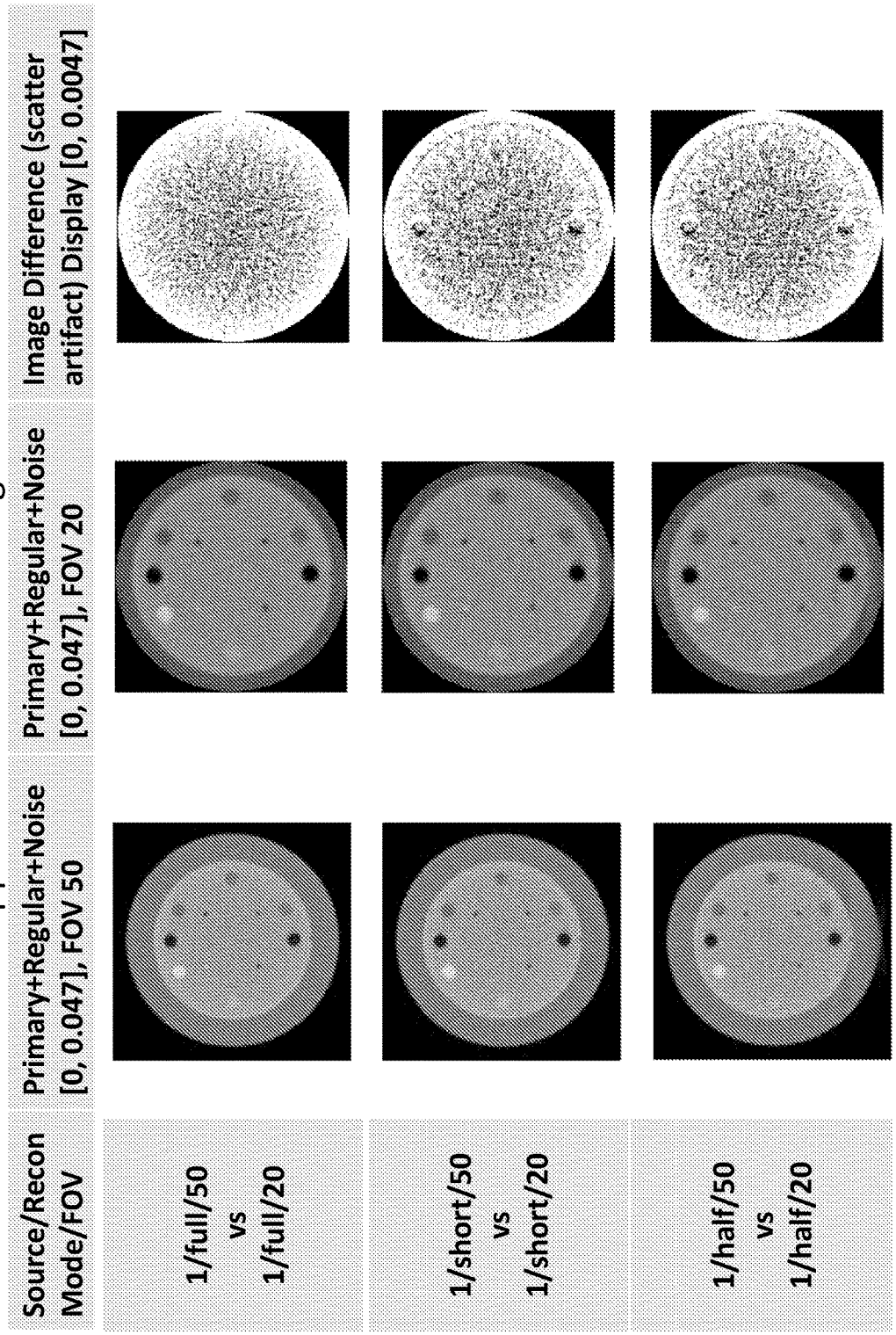
Figure 19F:
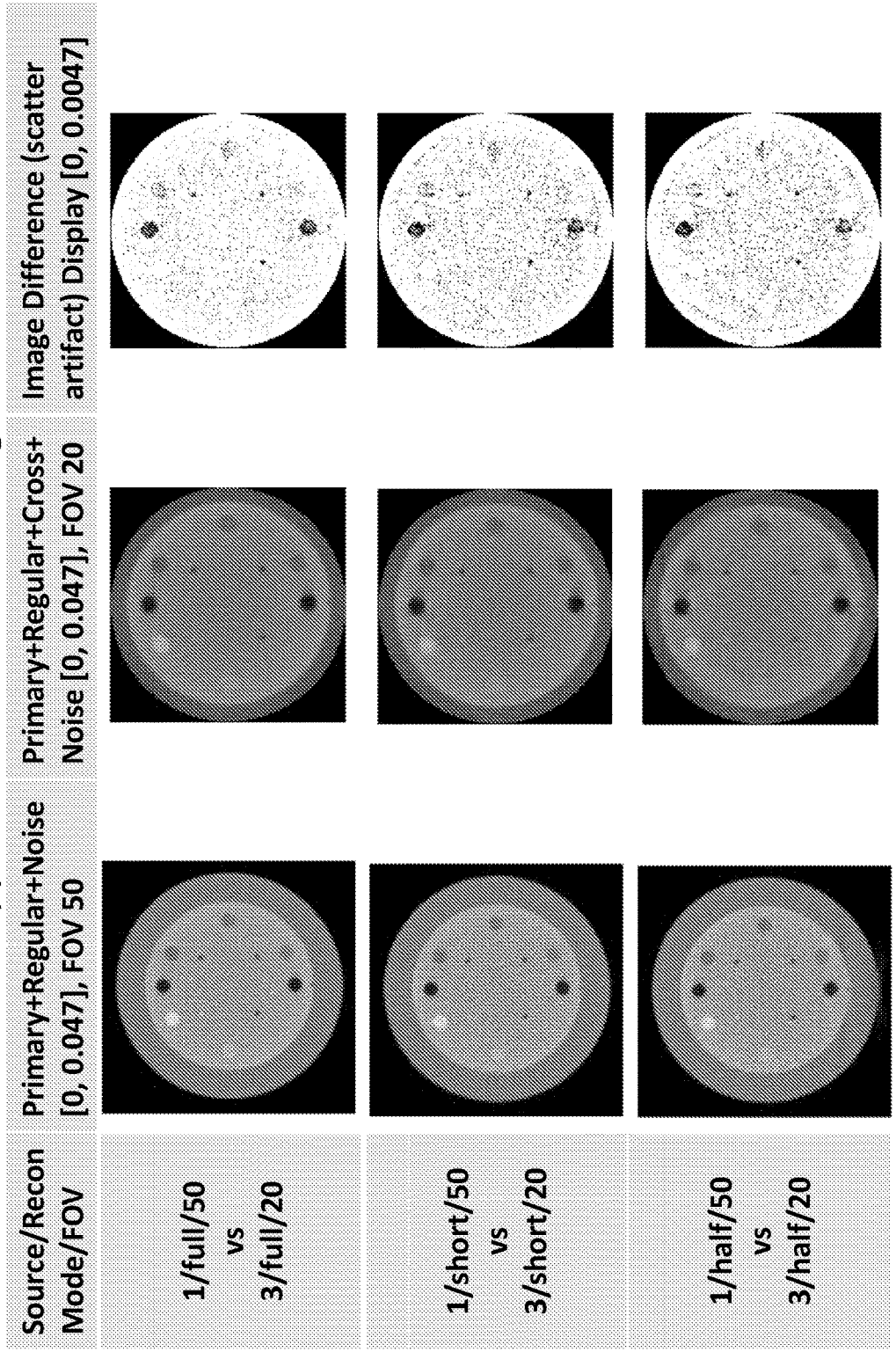
Figure 19G:
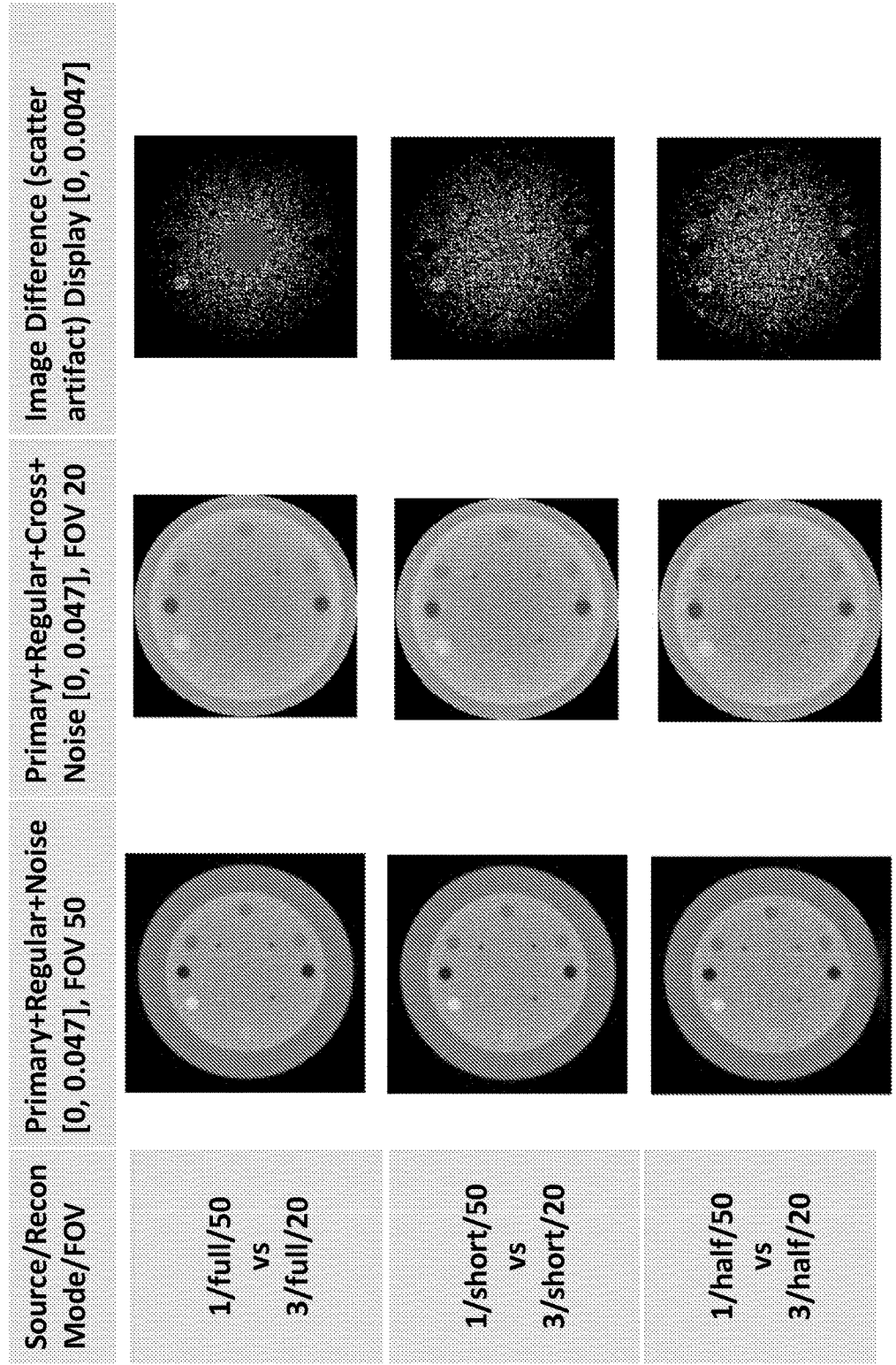
Figure 20A:
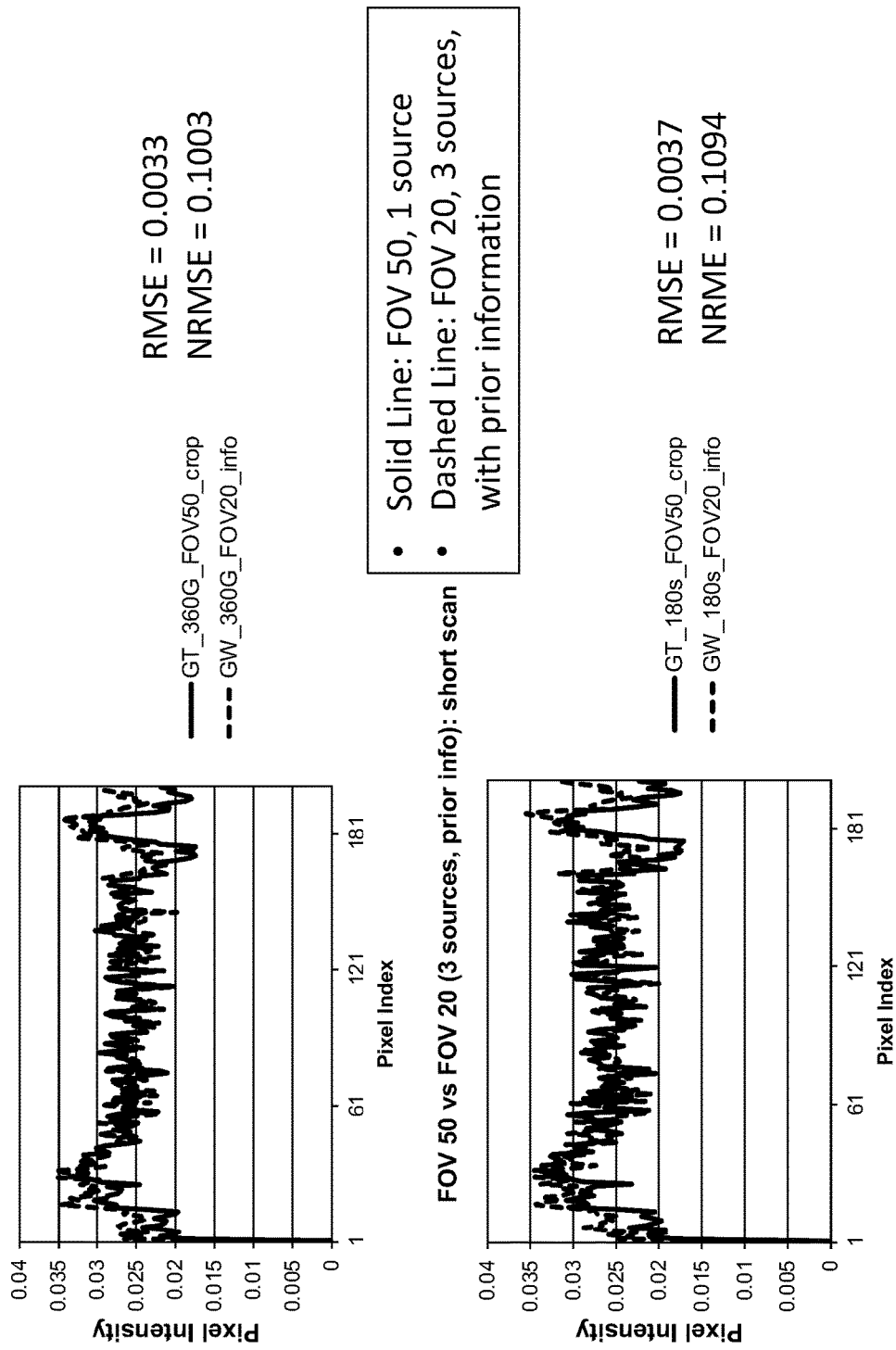
FIGS. 20A-B are graphs of line profiles of the data from FIGS. 19A-G.
Figure 20B:
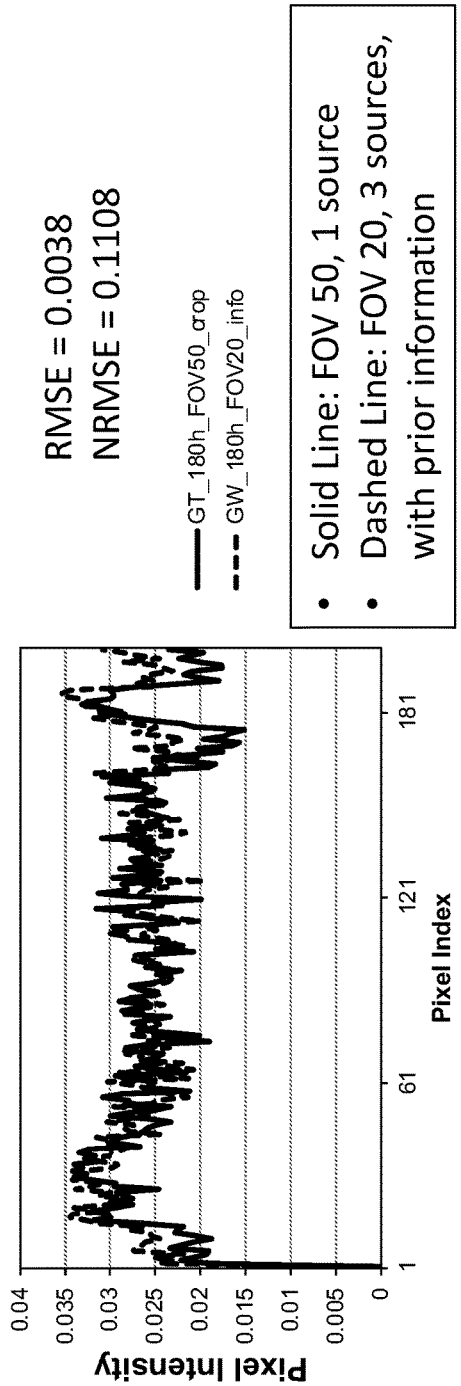

The image artifacts induced by interior tomography show (FIG. 19E) FOV 50 cm vs FOV 20 cm (1 source, no prior information) and (FIG. 19F) FOV 50 vs FOV 20 (3 source, no prior information). FIG. 19G shows FOV 50 vs FOV 20 (3 source, with prior information). FIGS. 20A-B are graphs of line profiles of the data from FIGS. 19A-G. Without prior information, the previously reconstructed images contain larger DC offset (FIGS. 19E and 19F). With prior information, the DC offset is largely ameliorated (FIGS. 19G and 20A-B). The line profiles demonstrate that the reconstructed central regions matches well with the standard ones (approximately corresponding to pixel index 30-150), with the discrepancy larger toward the edge.

Geometrical Calibration—In embodiments, the array is preferably in a precise geometrical arrangement. An analytic method for geometrical calibration, which is based on identification of elliptical trajectories of two point objects, can be used. See Noo, F., R. Clackdoyle, C. Mennessier, T. A. White, and T. J. Roney, Analytic Method Based on Identification of Ellipse Parameters for Scanner Calibration in Cone-Beam Tomography. Phys. Med. Biol., 2000. 45: p. 3489-3508. Previous micro-CT studies using this method demonstrate that the errors of the distance and angular parameters are <1 mm and <0.1°, respectively.

Dose Measurement—Radiation dose can be measured using a calibrated ion chamber. Dose per projection can be calculated, and the overall scan dose be compared with commercial CT values. For systems of the invention with three linear x-ray source arrays, the source-to-isocenter distance varies from beam to beam. The field emission x-ray sources offer the flexibility to modulate the tube current so that the fluence at an ROI does not differ much from beam to beam. The constant current and constant dose modes can be compared. The relationship can be established between tube current and radiation dose in an object. To provide for alternative configurations, the multi-beam x-ray source can have a vacuum envelope with a removable flange for easy exchange of the components. After initial testing, fully sealed x-ray source arrays can be built for use.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An omni-tomography system comprising:
a first imaging modality comprising a stationary source computed tomography (CT) architecture having:
at least one x-ray detector disposed or distributed on a rotatable gantry;
at least one stationary x-ray source disposed or distributed on a fixed structure;
wherein the at least one x-ray detector is disposed or distributed on the rotatable gantry in a manner such that the at least one x-ray detector is capable of rotating around a subject and receiving a signal from the at least one stationary x-ray source;
wherein the at least one stationary x-ray source comprises a plurality of stationary x-ray sources, each of the stationary x-ray sources with an angular range of between 60-120°, wherein the plurality of stationary x-ray sources is capable of performing a 180° scan without source rotation and without overlapping x-ray beams;
wherein the plurality of stationary x-ray sources are configured to provide non-continuous pulsed radiation; and
a second imaging modality comprising ultrasound, magnetic resonance imaging (MRI), positron emission tomography (PET), optical imaging, or single-photon emission computed tomography (SPECT), wherein the second imaging modality is disposed on a first static ring structure concentric to the rotatable gantry, which together provide for concentric ring structures.

2. The system of claim 1, further comprising at least one interior collimator disposed on the rotatable gantry opposite the at least one x-ray detector, wherein the system is capable of suppressing scattering artifacts through the at least one interior collimator and through synchronization between rotation of the rotatable gantry and activation of the at least one stationary x-ray source, such that the at least one x-ray detector, the at least one interior collimator, and the at least one activated stationary x-ray source will be aligned during use.

3. The system of claim 1, wherein the at least one stationary x-ray source comprises carbon nanotube cathodes or dispenser cathodes.

4. The system of claim 1, wherein the at least one x-ray detector comprises a plurality of x-ray detectors, and the system is capable of electronically activating or deactivating the plurality of stationary x-ray sources such that the activating or deactivating is synchronous with rotary movement of the plurality of x-ray detectors during use.

5. The system of claim 4, wherein the plurality of stationary x-ray sources comprise carbon nanotube cathodes or dispenser cathodes.

6. The system of claim 1, wherein the plurality of stationary x-ray sources are on-off programmable to emit a sweeping electron beam to simulate a rotary movement.

7. The system of claim 1, wherein the first and second imaging modalities are operably configured for concurrent signal acquisition for performing Region of Interest (ROI)-targeted reconstruction.

8. The system of claim 1, wherein the first imaging modality and the second imaging modality are configured as discrete subsystems of the omni-tomography system.

9. The system of claim 8, wherein the discrete subsystems are configured on or within the concentric ring structures.

10. The system of claim 9, wherein the first static ring structure of the concentric ring structures comprises the second imaging modality.

11. The system of claim 1, wherein the plurality of stationary x-ray sources are symmetrically disposed around a common center.

12. The system of claim 1, wherein the plurality of stationary x-ray sources are linear source arrays.

13. The system of claim 1, wherein the plurality of stationary x-ray sources are curved source arrays.

14. The system of claim 1, wherein the plurality of stationary x-ray sources are disposed such that they are co-planar to the at least one x-ray detector.

15. The system of claim 1, wherein the at least one x-ray detector is configured to rotate synchronously with switching of the at least one x-ray source.

16. The system of claim 1, wherein the first imaging modality further comprises at least one collimator mounted on the rotatable gantry such that each collimator of the at least one collimator is mounted opposite each x-ray detector of the at least one x-ray detector.

17. The system of claim 1, wherein the second imaging modality is MRI.

18. The system of claim 1, wherein the second imaging modality is PET.

19. The system of claim 1, wherein the second imaging modality is optical imaging.

20. The system of claim 1, wherein the second imaging modality is SPECT.

21. The system of claim 1, wherein the second imaging modality is ultrasound.

22. The system of claim 1, wherein the system comprises a second static ring structure concentrically disposed to the rotatable gantry, the first and second static ring structures each having a source and/or detector capable of one or more of the second imaging modality.

23. The system of claim 22, wherein the first and second imaging modalities are each configured as discrete subsystems.

* * * * *